United States Patent
Nishizawa et al.

(10) Patent No.: US 7,498,323 B2
(45) Date of Patent: Mar. 3, 2009

(54) SPIRO-PIPERIDINE COMPOUNDS AND MEDICINAL USE THEREOF

(75) Inventors: Rena Nishizawa, Mishima-gun (JP); Yoshikazu Takaoka, Mishima-gun (JP); Hiromu Habashita, Mishima-gun (JP); Shiro Shibayama, Tsukuba (JP); Masaya Kokubo, Mishima-gun (JP)

(73) Assignee: Ono Pharmaceuticals Co., Ltd., Osaka (JP)

( * ) Notice: Subject to any disclaimer, the term of this patent is extended or adjusted under 35 U.S.C. 154(b) by 13 days.

(21) Appl. No.: 10/553,596

(22) PCT Filed: Apr. 16, 2004

(86) PCT No.: PCT/JP2004/005493
§ 371 (c)(1), (2), (4) Date: Oct. 18, 2005

(87) PCT Pub. No.: WO2004/092169
PCT Pub. Date: Oct. 28, 2004

(65) Prior Publication Data
US 2006/0229301 A1 Oct. 12, 2006

(30) Foreign Application Priority Data
Apr. 18, 2003 (JP) ............................... 2003-114188

(51) Int. Cl.
| | |
|---|---|
| A01N 43/62 | (2006.01) |
| A01N 43/58 | (2006.01) |
| A01N 43/60 | (2006.01) |
| A01N 43/42 | (2006.01) |
| A61K 31/55 | (2006.01) |
| A61K 31/50 | (2006.01) |
| A61K 31/495 | (2006.01) |
| A61K 31/44 | (2006.01) |
| C07D 471/04 | (2006.01) |
| C07D 471/22 | (2006.01) |
| C07D 487/00 | (2006.01) |
| C07D 491/00 | (2006.01) |
| C07D 495/00 | (2006.01) |
| C07D 215/00 | (2006.01) |
| C07D 217/00 | (2006.01) |
| C07D 219/00 | (2006.01) |
| C07D 221/00 | (2006.01) |
| C07D 237/00 | (2006.01) |
| C07D 239/00 | (2006.01) |
| C07D 241/00 | (2006.01) |

(52) U.S. Cl. .................. 514/221; 514/249; 514/257; 514/278; 540/502; 546/16; 544/231

(58) Field of Classification Search .................. None
See application file for complete search history.

(56) References Cited

U.S. PATENT DOCUMENTS

| | | | | |
|---|---|---|---|---|
| 3,301,857 A | * | 1/1967 | Berger et al. .................. 546/18 |
| 6,291,469 B1 | | 9/2001 | Fisher et al. | |
| 2002/0189124 A1 | | 12/2002 | Nelson et al. | |
| 2003/0187023 A1 | | 10/2003 | Keiji | |

FOREIGN PATENT DOCUMENTS

| | | |
|---|---|---|
| JP | 49-13184 A | 2/1974 |
| JP | 49-72332 A | 7/1974 |
| JP | EP 70171 | 1/1983 |
| JP | 4-18092 A | 1/1992 |
| JP | 2002-348288 A | 12/2002 |
| WO | WO 95/01358 A1 | 1/1995 |
| WO | WO 97/11940 A1 | 4/1997 |
| WO | WO 98/25605 A1 | 6/1998 |
| WO | WO 01/13917 * | 3/2001 |
| WO | WO 02/074770 A1 | 9/2002 |
| WO | WO 03/020721 A1 | 3/2003 |
| WO | WO 03/057698 A2 | 7/2003 |

OTHER PUBLICATIONS

Lipinski, C.A.; Bioisosterism in Drug Design; Annual Reports in Medicinal Chemistry vol. 21, 1986; pp. 283-291.*
Mirzadegan et al.; Identification of the binding site for a novel class of CCR2b chemokine receptor antagonists; Journal of Biological Chemistry; vol. 275; Issue 33 (2000) p. 25562-25571.*

(Continued)

Primary Examiner—James O. Wilson
Assistant Examiner—Jeffrey H Murray
(74) Attorney, Agent, or Firm—Sughrue Mion, PLLC

(57) ABSTRACT

The present invention relates to a spiro-piperidine compound represented by formula (I):

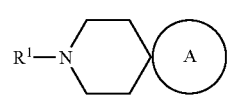

(I)

wherein $R^1$ represents hydrogen, an aliphatic hydrocarbon group which may have a substituent(s) or a cyclic group which may have a substituent(s); and ring A represents a 5- to 8-membered cyclic group which may have a substituent(s), a salt thereof, an N-oxide thereof, a quaternary ammonium salt thereof or a solvate thereof, or a prodrug thereof. The compounds represented by formula (I) have chemokine antagonistic action, so that they are useful for prevention and/or treatment of various inflammatory diseases, immune diseases such as autoimmune diseases or allergic diseases, or HIV infection.

6 Claims, No Drawings

OTHER PUBLICATIONS

CA 1983:470751. See CA registry # 85732-34-9 and CA registry # 85732-35-0.*

CA 1984:510946. See CA registry # 85732-35-0 and CA registry # 85732-42-9.*

CA 1989:407312. See CA registry # 85732-35-0 and CA registry # 121061-07-2.*

CA 2003:282402. See CA registry # 508240-62-8 and CA registry # 508240-61-7.*

CA 2003:991516. See CA registry # 635713-68-7 and CA registry # 635713-67-6.*

Vippagunta et. al. Advanced Drug Delivery Reviews 48 (2001) 3-26.*

International Search Report for PCT/JP04/005493.

* cited by examiner

SEQUENCE LISTING

```
<160> NUMBER OF SEQ ID NOS: 2

<210> SEQ ID NO 1
<211> LENGTH: 37
<212> TYPE: DNA
<213> ORGANISM: Artificial Sequence
<220> FEATURE:
<223> OTHER INFORMATION: Forward primer hCCR5XbaI

<400> SEQUENCE: 1
agctagtcta gatccgttcc cctacaagaa actctcc                              37

<210> SEQ ID NO 2
<211> LENGTH: 37
<212> TYPE: DNA
<213> ORGANISM: Artificial Sequence
<220> FEATURE:
<223> OTHER INFORMATION: Reverse primer hCCR5XbaI

<400> SEQUENCE: 2
agctagtcta gagtgcacaa ctctgactgg gtcacca                              37
```

SPIRO-PIPERIDINE COMPOUNDS AND MEDICINAL USE THEREOF

TECHNICAL FIELD

The present invention relates to spiro-piperidine compounds having chemokine receptor antagonism which are useful as medicines, drugs comprising them as the active ingredients, and production methods and use thereof.

BACKGROUND OF THE INVENTION

Chemokine is known as a basic protein having endogeneous leukocyte chemotactic and activating abilities and heparin-binding abilities. At present, it is considered that chemokine is related to not only the control of infiltration of specific leukocyte at the time of inflammations and immune responses but also the development and homing of lymphocyte under physiological conditions and migration of hemocyte precursor cells and somatic cells.

Differentiation, proliferation and cell death of hemocytes are controlled by various types of cytokine. In the living body, inflammations are found topically and differentiation, maturation and the like of lymphocytes are carried out at certain specified sites. That is, various necessary cells migrate into certain specified sites and accumulate therein to cause a series of inflammations and immune responses. Accordingly, migration of cells is also an indispensable phenomenon in addition to differentiation, proliferation and death of cells.

Migration of hemocytes in the living body starts firstly in the development stage by the shift of hematopoiesis started in the AGM (aorta gonad mesonephros) region into permanent hematopoiesis in bone marrow via fetal liver. Furthermore, precursor cells of T cells and thymus dendritic cells migrate from the fetal liver into the bone marrow and then into the thymus gland and cytodifferentiate under thymus environment. The T cell which received clone selection migrates into secondary lymphoid tissues and takes part in an immune response in the periphery. The Langerhans' cell of the skin activated and differentiated by capturing an antigen migrates into the T cell region of a topical lymph node and activates naive T cell therein as a dendritic cell. The memory T cell performs its homing again into the lymph node via lymphatic and blood vessels. Also, B cell, T cell in the intestinal epithelium, γδ T cell, NKT cell and dendritic cell migrate from bone marrow without passing through the thymus gland and differentiate to take part in an immune response.

Chemokine is deeply concerned in the migration of various cells. For example, in order to effect efficient encounter of an antibody-captured mature dendritic cell with a naïve T cell and a memory T cell, MIP 3β (macrophage inflammatory protein 3β), SLC (secondary lymphoid tissue chemokine) and CCR7 as a receptor thereof are taking an important role in the migration and homing of these cells to a topical lymphoid tissue. T cells and dendritic cells necessary for controlling antigen-specific immune response are hardly observed in the secondary lymph node of PLT mouse having defection in the SLC expression (*J. Exp. Med,* 189 (3), 451 (1999)).

MDC (macrophage-derived chemokine), TARC (thymus and activation-regulated chemokine) and CCR4 as a receptor thereof are taking an important role in the migration of Th2 cell into a topical region in immune and inflammatory responses in which the Th2 cell is concerned. In a rat fulminant hepatitis model (P. acnes+LPS), an anti-TARC antibody inhibited increase of the blood ALT level and increase of the expression quantity of TNFα and FasL in the liver, and improved rat lethality (*J. Clin. Invest.,* 102, 1933 (1998)).

Also, in a mouse OVA-induced airway hypersensitivity model, an anti-MDC antibody reduced the number of eosinophils accumulating in the lung interstitium and inhibited the airway hypersensitivity (*J. Immunology,* 163, 403 (1999)).

MCP-1 (monocyte chemoattractant protein-1) and its receptor CCR2 are concerned in the infiltration of macrophage into inflammatory regions. In a rat anti-Thy1.1 antibody glomerular nephritis model, an anti-MCP-1 antibody showed an effect to inhibit infiltration of monocyte and macrophage into the uterine body (*Kidney Int.,* 51, 770 (1997)).

Thus, chemokine receptors are greatly concerned in the control of inflammatory and immune responses through a mechanism in which they are expressed in various specific cells at a specified period, and the effector cells are accumulated into a region where the chemokine is produced.

Acquired immunodeficiency syndrome (called AIDS) which is induced by human immunodeficiency virus (hereinafter referred to as "HIV") is one of the diseases of which their therapeutic methods are most earnestly desired in recent years. Once infection with HIV is completed in a CD4-positive cell which is a principal target cell, HIV repeats its proliferation in the body of the patient and, sooner or later, completely destroys T cell which takes charge of the immunological function. During this process, the immunological function is gradually reduced to cause fever, diarrhea, lymph node enlargement and the like various immunodeficiency conditions which are apt to cause complications with pneumocystis carinii pneumonia and the like various opportunistic infections. Such conditions are the onset of AIDS, and it is well known that they induce and worsen Kaposi sarcoma and the like malignant tumors.

As the recent preventive and therapeutic methods for AIDS, attempts have been made to, e.g., (1) inhibit growth of HIV by the administration of a reverse transcriptase inhibitor or a protease inhibitor and (2) prevent or alleviate opportunistic infections by the administration of a drug having immunopotentiation activity.

Helper T cells which take charge of the central of immune system are mainly infected with HIV. It is known since 1985 that HIV uses the membrane protein CD4 expressing on the membrane of T cells in the infection (*Cell,* 52, 631 (1985)). The CD4 molecule is composed of 433 amino acid residues, and its expression can be found in macrophages, some B cells, vascular endothelial cells, Langerhans' cells in skin tissues, dendritic cells in lymphoid tissues, glia cells of the central nervous system and the like, in addition to the mature helper T cells. However, since it has been revealed that the infection with HIV is not completed by the CD4 molecule alone, a possibility has been suggested on the presence of factors other than the CD4 molecule, which are related to the infection of cells with HIV.

In 1996, a cell membrane protein called Fusin was identified as a factor concerned in the HIV infection of other than CD4 molecule (*Science,* 272, 872 (1996)). It was shown that this Fusin molecule is a receptor of a stromal cell-derived factor-1 (Stromal Derived Factor-1: to be referred to as SDF-1) (that is, CXCR4). In addition, it was shown also that SDF-1 specifically inhibits T cell-directional (X4) HIV infection (*Nature,* 382, 829 (1996), *Nature,* 382, 833 (1996)). That is, it is considered that the HIV infection was inhibited through the deprivation of a foothold for HIV to infect upon cells, effected by the binding of SDF-1 to CXCR4 prior to that of HIV.

In addition, it was discovered during the same period that CCR5 as another chemokine receptor which is the receptor of RANTES, MIP-1α and MIP-1β is also utilized in infecting macrophage-directional (R5) HIV (*Science*, 272, 1955 (1996)).

Accordingly, a substance which can scramble for HIV and CXCR4 or CCR5, or which can bind to HIV virus to provide such a state that said virus cannot bind to CXCR4 or CCR5, may become an HIV infection inhibitor. In addition, there is a case in which a low molecular compound discovered in the beginning as an HIV infection inhibitor was found to be a CXCR4 antagonist in reality (*Nature Medicine*, 4 72 (1998)).

Based on the above, it is considered that chemokine receptors are deeply related to various inflammatory diseases, immune diseases such as autoimmune diseases or allergic diseases, or HIV infection. For example, it is considered that they are related to asthma, nephritis, nephropathy, hepatitis, arthritis, rheumatoid arthritis, rhinitis, conjunctivitis, ulcerative colitis, and the like, rejection in organ transplantation, immunosuppression, psoriasis, multiple sclerosis, infection with human immunodeficiency virus (acquired immunodeficiency syndrome and the like), atopic dermatitis, uticaria, allergic bronchopulmonary aspergillosis, allergic eosinophilic gastroenteritis, ischemic reperfusion injury, acute respiratory distress syndrome, shock accompanying bacterial infection, diabetes mellitus, cancer metastasis, arteriosclerosis and the like.

On the other hand, there is a description that a compound represented by formula (Z) is useful for the inhibition of platelet agglutination:

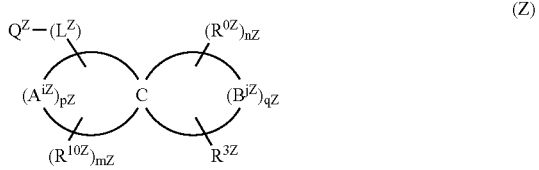

(Z)

wherein $A^{iz}$ and $B^{jz}$ are each independently selected from carbon, nitrogen, oxygen or sulfur (however, at least one atom of $A^{iz}$ is carbon, and at least one of $B^{jz}$ is carbon);

each of the spiro-bicycles formed by $A^{iz}$ and $B^{jz}$ may be partially unsaturated in some cases, pZ and qZ are each independently a number of from 2 to 6, mZ is a number of from 0 to pZ, $R^{10z}$ may be the same or different from one another and are incoherent substituents each independently selected from hydrogen, alkyl, halo-substituted alkyl, alkenyl, alkynyl, cycloalkyl, =O, =S and the like, nZ is a number of from 0 to qZ, $R^{0z}$ may be the same or different from one another and are incoherent substituents each independently selected from hydrogen, alkyl, halo-substituted alkyl, alkenyl, alkynyl, cycloalkyl, =O, =S and the like, -($L^z$)- is a bond, or a substituted or unsubstituted divalent chain consisting of from 1 to 10 atoms selected from carbon, nitrogen, sulfur and oxygen, $Q^z$ is a basic group comprising one or two or more of basic radicals, and $R^{3z}$ is an acidic group comprising one or two or more of acidic radicals (e.g., see WO 97/11940).

Also, there is a description that a compound represented by formula (Y) is 10 useful as a chemokine receptor modulator:

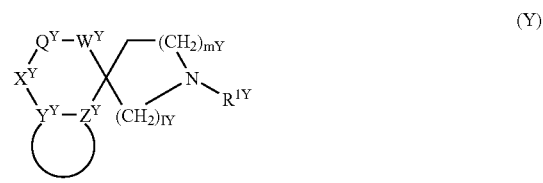

(Y)

wherein mY or lY each independently represents 0, 1, 2, 3, 4 or 5, $R^{1Y}$ represents hydrogen, C1-8 alkyl, C2-8 alkenyl, C2-8 alkynyl or the like, $W^Y$ represents a single bond, C1-3 alkyl, C1-3 alkyl substituted with oxo, etc., or the like, $Q^Y$ represents —$NR^2$—, —O—, —S—, —S(O)— or —$SO_2$—, $X^Y$ represents a single bond, C1-3 alkyl, C1-3 alkyl substituted with oxo, etc., or the like, and $Y^Y$-$Z^Y$ ring represents phenyl, naphthyl or heteroaryl. However, definition of each symbol is a partial extract (e.g., see WO 98/25605).

In addition, there is a description that a triazaspiro[5.5] undecane derivative compound represented by formula (X) is useful for inhibiting asthma, atopic dermatitis, nettle rash, allergic bronchopulmonary aspergillosis, allergic eosinophilic gastroenteritis, glomerulonephritis, nephropathy, hepatitis, arthritis, rheumatoid arthritis, psoriasis, rhinitis, conjunctivitis or ischemia-reperfusion injury, for treating multiple sclerosis, ulcerative colitis, acute respiratory distress syndrome, shock accompanied by bacterial infection, diabetes mellitus or autoimmune disease, for preventing transplanted organ rejection reaction, immunosuppression or metastasis, or as a preventive and/or therapeutic agent for acquired immunodeficiency syndrome, by controlling chemokine/chemokine receptor interaction:

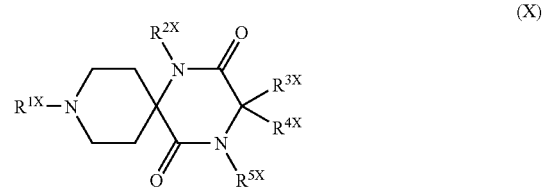

(X)

wherein $R^{1x}$ is a formula (X-2)

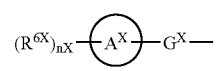

(X-2)

or a formula (X-3):

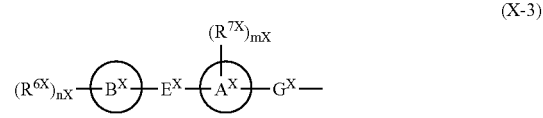

(X-3)

$R^{2x}$ represents alkyl, alkynyl or the like; each of $R^{3x}$ and $R^{4x}$ represents H, (substituted) alkyl or the like, or $R^{3x}$ and $R^{4x}$ together represent a formula (X-4):

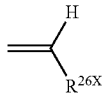

(X-4)

and $R^{5x}$ represents H or alkyl (e.g., WO 02/74770).

DISCLOSURE OF THE INVENTION

An object of the present invention is to develop a CCR5 antagonist which is a safe medicament having excellent oral absorbability and is useful as a preventive and/or therapeutic agent for human immunodeficiency virus (HIV) infection, acquired immunodeficiency syndrome (AIDS) and the like.

In order to obtain a compound having CCR5 antagonism, the present inventors have conducted intensive studies and found as a result that a compound represented by formula (I) can achieve the object of the present invention, thereby accomplishing the present invention.

That is, the present invention relates to 1. a spiro-piperidine compound represented by formula (I):

(I)

wherein $R^1$ represents hydrogen, an aliphatic hydrocarbon group which may have a substituent(s) or a cyclic group which may have a substituent(s); and ring A represents a 5- to 8-membered cyclic group which may have a substituent(s), in which 2,5-diketopiperazine having a spiro bond at the 3-position is excluded, ring A may be further condensed with ring B, and ring B represents a 3- to 8-membered monocyclic carbon ring or hetero ring which may have a substituent(s), a salt thereof, an N-oxide thereof, a quaternary ammonium salt thereof or a solvate thereof, or a prodrug thereof, 2. the spiro-piperidine compound according to the above-described 1, wherein the ring A is a 5- to 8-membered hetero ring which may have a substituent(s), a salt thereof, an N-oxide thereof, a quaternary ammonium salt thereof or a solvate thereof, or a prodrug thereof, 3. the spiro-piperidine compound according to the above-described 2, wherein the ring A is a 5- to 8-membered nitrogen-containing hetero ring which may have a substituent(s), a salt thereof, an N-oxide thereof, a quaternary ammonium salt thereof or a solvate thereof, or a prodrug thereof, 4. the spiro-piperidine compound according to the above-described 3, wherein the ring A is represented by

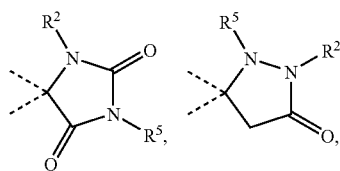

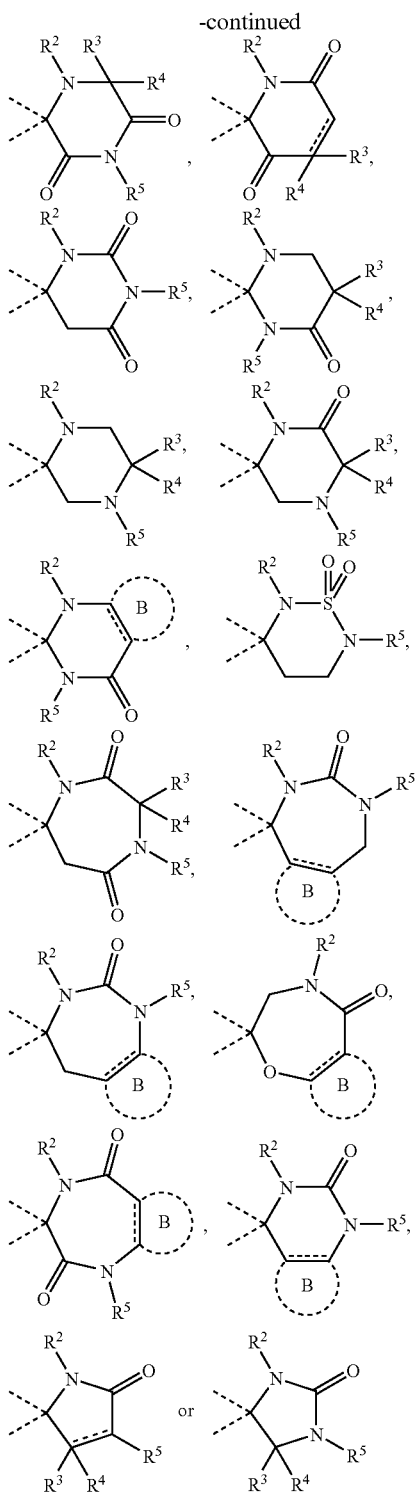

wherein ----- represents a single bond or a double bond; and $R^2$, $R^3$, $R^4$ and $R^5$ each independently represents hydrogen, an aliphatic hydrocarbon group which may have a substituent(s), hydroxyl which may be protected, carboxy which may be protected, carbamoyl which may be protected, or a cyclic group which may have a substituent(s), or $R^3$ and $R^4$ are taken together to represent

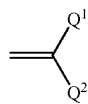

wherein $Q^1$ and $Q^2$ each independently represents hydrogen, an aliphatic hydrocarbon group which may have a substituent(s), hydroxyl which may be protected, carboxy which may be protected, carbamoyl which may be protected, or a cyclic group which may have a substituent(s); and ring B represents a 3- to 8-membered monocyclic carbon ring or hetero ring which may have a substituent(s), and wherein when ring A represents

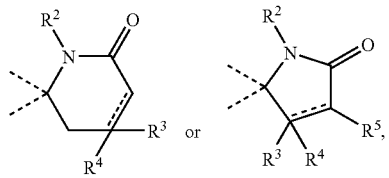

$R^4$ is present so long as ----- represents a single bond, a salt thereof, an N-oxide thereof, a quaternary ammonium salt thereof or a solvate thereof, or a prodrug thereof, 5. the spiro-piperidine compound according to the above-described 4, wherein the ring A is represented by

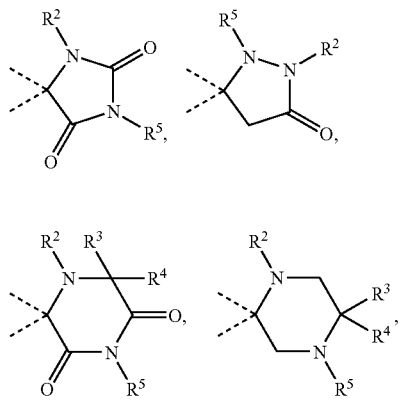

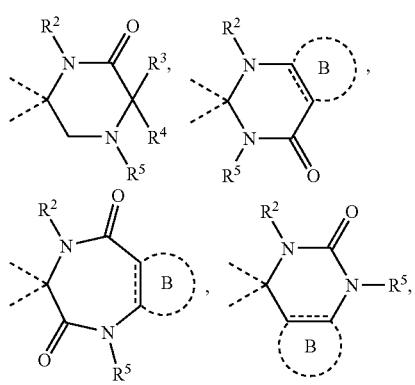

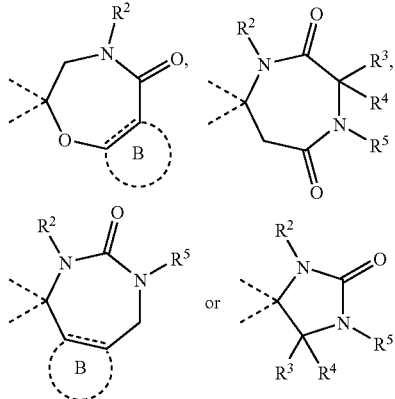

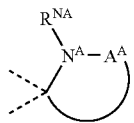

wherein all symbols have the same meanings as those defined in the above-described 4, a salt thereof, an N-oxide thereof, a quaternary ammonium salt thereof or a solvate thereof, or a prodrug thereof, 6. the spiro-piperidine compound according to the above-described 3, wherein the ring A is represented by

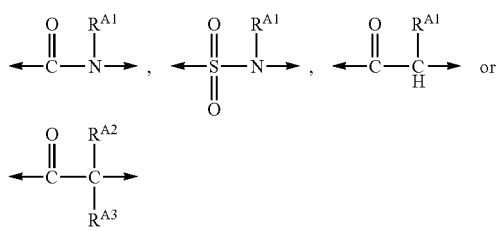

wherein $N^A$ represents nitrogen;

$R^{NA}$ represents an aliphatic hydrocarbon group which may have a substituent(s), hydroxyl which may be protected, carboxy which may be protected, carbamoyl which may be protected, or a cyclic group which may have a substituent(s); and $A^A$ represents

wherein arrow represents a position capable of binding to $N^A$;

$R^{A1}$, $R^{A2}$ and $R^{A3}$ each independently represents an aliphatic hydrocarbon group which may have a substituent(s), hydroxyl which may be protected, carboxy which may be protected, carbamoyl which may be protected, or a cyclic group which may have a substituent(s), or $R^{A2}$ and $R^{A3}$ are taken together to represent wherein $Q^{41}$ and $Q^{42}$ each independently represents hydrogen, an aliphatic hydrocarbon group which may have a substituent(s), hydroxyl which may be protected, carboxy which may be protected, carbamoyl which may be protected, or a cyclic group which may have a substituent(s), and wherein at least one of $Q^{41}$ and $Q^{42}$ does not represent hydrogen, a salt thereof, an N-oxide thereof, a quaternary ammonium salt thereof or a solvate thereof, or a prodrug thereof, 7. the spiro-piperidine compound according to the above-described 1, wherein $R^1$ is a C1-10 aliphatic hydrocarbon group which may have a substituent(s), a salt thereof, an N-oxide thereof, a quaternary ammonium salt thereof or a solvate thereof, or a prodrug thereof, 8. the spiro-piperidine compound according to the above-described 1, wherein $R^1$ is a 5- to 10-membered monocyclic or bicyclic cyclic group which may have a substituent(s), a salt thereof, an N-oxide thereof, a quaternary ammonium salt thereof or a solvate thereof, or a prodrug thereof, 9. the spiro-piperidine compound according to the above-described 1, wherein $R^1$ is alkyl having from 1 to 6 carbon atoms substituted with a 3- to 10-membered monocyclic or bicyclic cyclic group which may have a substituent(s), a salt thereof, an N-oxide thereof, a quaternary ammonium salt thereof or a solvate thereof, or a prodrug thereof, 10. a pharmaceutical composition which comprises the spiro-piperidine compound according to the above-described 1, 11. the pharmaceutical composition according to the above-described 10, which is a chemokine receptor antagonist, 12. the pharmaceutical composition according to the above-described 11, wherein the chemokine receptor is CCR5, 13. the pharmaceutical composition according to the above-described 10, which is a preventive and/or therapeutic agent for human immunodeficiency virus infection, 14. the pharmaceutical composition according to the above-described 10, which is a preventive and/or therapeutic agent for acquired immunodeficiency syndrome, 15. the pharmaceutical composition according to the above-described 10, which is a morbid state progress inhibitor for acquired immunodeficiency syndrome, 16. the pharmaceutical composition according to the above-described 11, wherein the chemokine receptor is CCR2, 17. the pharmaceutical composition according to the above-described 10, which is a preventive and/or therapeutic agent for arteriosclerosis or nephropathy, 18. a medicament which comprises a combination of the spiro-piperidine compound according to the above-described 1, a salt thereof, an N-oxide thereof, a quaternary ammonium salt thereof or a solvate thereof, or a prodrug thereof with one or at least two of agents selected from protease inhibitors, reverse transcriptase inhibitors, integrase inhibitors, fusion inhibitors and/or chemokine inhibitors, 19. a method for preventing and/or treating diseases caused by CCR5 or CCR2 in a mammal, which comprises administering to a mammal an effective amount of the spiro-piperidine compound according to the above-described 1, a salt thereof, an N-oxide thereof, a quaternary ammonium salt thereof or a solvate thereof, or a prodrug thereof, and 20. use of the spiro-piperidine compound according to the above-described 1, a salt thereof, an N-oxide thereof, a quaternary ammonium salt thereof or a solvate thereof, or a prodrug thereof for the manufacture of a preventive and/or therapeutic agent for diseases caused by CCR5 or CCR2, and the like.

According to this specification, the "2,5-diketopiperazine having a Spiro bond at the 3-position" represents the structure of a compound described in WO 02/74770, that is,

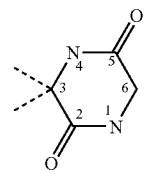

Nomenclature and numbering of the compounds of the present invention were carried out using a computer program, ACD/NAME (trade name, version 5.08/17) of Advanced Chemistry Development, which mechanically produces IUPAC names.

For example, a compound in which, in formula (I), $R^1$ represents hydrogen, ring A represents

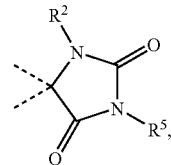

$R^2$ represents

H₃C~~~, and $R^5$ represents

<br>CH₃<br>~CH₃, that is, a compound represented by is named 1-butyl-3-isobutyl-1,3,8-triazaspiro[4.5]decane-2,4-dione.

As the "aliphatic hydrocarbon group" in the "aliphatic hydrocarbon group which may have a substituent(s)", for example, "straight chain or branched chain C1-18 hydrocarbon group" and the like can be cited. As the "straight chain or branched chain C1-18 hydrocarbon group", for example, C1-18 alkyl, C2-18 alkenyl, C2-18 alkynyl and the like can be cited. In this case, as the C1-18 alkyl, for example, methyl, ethyl, propyl, isopropyl, butyl, isobutyl, sec-butyl, tert-butyl, pentyl, hexyl, heptyl, octyl, nonyl, decyl, undecyl, dodecyl, tridecyl, tetradecyl, pentadecyl, hexadecyl, heptadecyl, octadecyl and isomer groups thereof and the like can be cited. As the C2-18 alkenyl, for example, vinyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, butadienyl, pentadienyl, hexadienyl, heptadienyl, octadienyl, nonadienyl, decadienyl, undecadienyl, dodecadienyl, tridecadienyl, tetradecadienyl, pentadecadienyl, hexadecadienyl, heptadecadienyl, octadecadienyl, hexatrienyl, heptatrienyl, octatrienyl, nonatrienyl, decatrienyl, undecatrienyl, dodecatrienyl, tridecatrienyl, tetradecatrienyl, pentadecatrienyl, hexadecatrienyl, heptadecatrienyl, octadecatrienyl and isomer groups thereof and the like can be cited. As the C2-18 alkynyl, for example, ethynyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, butadiynyl, pentadiynyl, hexadiynyl, heptadiynyl, octadiynyl, nonadiynyl, decadiynyl, undecadiynyl, dodecadiynyl, tridecadiynyl, tetradecadiynyl, pentadecadiynyl, hexadecadiynyl, heptadecadiynyl, octadecadiynyl, hexatriynyl, heptatriynyl, octatriynyl, nonatriynyl, decatriynyl, undecatriynyl, dodecatriynyl, tridecatriynyl, tetradecatriynyl, pentadecatriynyl, hexadecatriynyl, heptadecatriynyl, octadecatriynyl and isomer groups thereof and the like can be cited.

Preferred as the "aliphatic hydrocarbon group" in the "aliphatic hydrocarbon group which may have a substituent(s)" represented by $R^1$ are, for example, an aliphatic hydrocarbon group having from 1 to 10 carbon atoms, more preferred are, for example, an alkyl having from 1 to 6 carbon atoms, an alkenyl having from 2 to 6 carbon atoms and the like, and particularly preferred are, for example, an alkyl having from 1 to 6 carbon atoms and the like. In particular, methyl and ethyl are desirable.

In the specification, the "substituent" in the "aliphatic hydrocarbon group which may have a substituent(s)" represented by $R^1$ is not particularly limited, so long as it is a substituent. As this "substituent", for example, (a) a substituent selected from the following first group, (b) a substituent selected from the following second group and (c) a cyclic group which may have a substituent(s), and the like can be cited, and from 1 to 5 of these optional substituents may be substituted at substitutable positions.

<First Group>

(1) halogen (e.g., chlorine, bromine, fluorine, iodine or the like), (2) nitro, (3) trifluoromethyl, (4) trifluoromethoxy, (5) cyano, (6) oxo, <Second Group>

(1) —$SR^{a1}$, (2) —$SO_2R^{a1}$, (3) —$SO_2NR^{b1}R^{b2}$, (4) —$S(O)R^{a1}$, (5) —$OR^{a1}$, (6) —$OCOR^{a1}$, (7) —$NR^{a1}SO_2R^{a2}$, (8) —$NR^{b1}R^{b2}$, (9) —$NR^{a1}COR^{a2}$, (10) —$NR^{a1}COOR^{a2}$ (11) —$NR^{a1}CONR^{b1}R^{b2}$ (12) —$N(SO_2R^{a1})_2$, (13) —$COR^{a1}$, (14) —$COOR^{a1}$, (15) —$CONR^{b1}R^{b2}$, (16) —$CONR^{a1}COR^{a2}$, (17) —$COCOOR^{a1}$, (18) —$B(OR^{a1})_2$, wherein $R^{a1}$, $R^{a2}$, $R^{b1}$ and $R^{b2}$ each independently represents hydrogen, a cyclic group (ring 1) which may have a substituent(s) or an aliphatic hydrocarbon group which may have a substituent(s), or together with the adjacent nitrogen, $R^{b1}$ and $R^{b2}$ represent (1) —C2-6 alkylene (e.g., methylene, ethylene, trimethylene, tetramethylene, pentamethylene, hexamethylene and isomer groups thereof and the like)-, (2) —(C2-6 alkylene)-O—(C2-6 alkylene)-, (3) —(C2-6 alkylene)-S—(C2-6 alkylene)-, (4) —(C2-6 alkylene)-$NR^{N1}$—(C2-6 alkylene)- (wherein $R^{N1}$ represents hydrogen, a cyclic group (ring 1) which may have a substituent(s) or a C1-8 alkyl may be susbtituted with the "cyclic group (ring 1) which may have a substituent(s)").

As the "aliphatic hydrocarbon group" in the "aliphatic hydrocarbon group which may have a substituent(s)" represented by $R^{a1}$, $R^{a2}$, $R^{b1}$ and $R^{b2}$, for example, a "straight chain or branched C1-8 hydrocarbon group" and the like can be cited. As the "straight chain or branched chain C1-8 hydrocarbon group", for example, C1-8 alkyl, C2-8 alkenyl, C2-8 alkynyl and the like can be cited. In this case, as the C1-8 alkyl, for example, methyl, ethyl, propyl, isopropyl, butyl, isobutyl, sec-butyl, tert-butyl, pentyl, hexyl, heptyl, octyl and isomer groups thereof and the like can be cited. As the C2-8 alkenyl, for example, vinyl, propenyl, butenyl, pentenyl, hexenyl, heptenyl, octenyl, butadienyl, pentadienyl, hexadienyl, heptadienyl, octadienyl, hexatrienyl, heptatrienyl, octatrienyl and isomer groups thereof and the like can be cited. As the C2-8 alkynyl, for example, ethynyl, propynyl, butynyl, pentynyl, hexynyl, heptynyl, octynyl, butadiynyl, pentadiynyl, hexadiynyl, heptadiynyl, octadiynyl, hexatriynyl, heptatriynyl, octatriynyl and isomer groups thereof and the like can be cited.

The "substituent" in the "aliphatic hydrocarbon group which may have a substituent(s)" represented by $R^{a1}$, $R^{a2}$, $R^{b1}$ and $R^{b2}$ is not particularly limited, so long as it is a substituent.

As this "substituent", for example, (a) a cyclic group (ring 1) which may have a substituent(s) and (b) a substituent selected from the following third group can be cited, and from 1 to 5 of these optional substituents may be substituted at substitutable positions.

<Third Group>

(1) halogen, (2) —$OR^{c1}$, (3) —$SR^{c1}$, (4) —$NR^{d1}R^{d2}$, (5) —$COOR^{c1}$, (6) —$CONR^{d1}R^{d2}$, (7) —$NR^{c1}COR^{c2}$, (8) —$NR^{c1}SO_2R^{c2}$, (9) —$N(SO_2R^{c1})_2$, wherein $R^{c1}$, $R^{c2}$, $R^{d1}$ and $R^{d2}$ have the same meanings as the above-described $R^{a1}$, $R^{a2}$, $R^{b1}$ and $R^{b2}$, respectively; however, each of the $R^{c1}$, $R^{c2}$, $R^{d1}$ and $R^{d2}$ does not represent an aliphatic hydrocarbon group susbtituted with a substituent selected from this group (third group).

In the specification, for example, a carbon ring, a hetero ring and the like can be cited as the "cyclic group" in the "cyclic group (ring 1) which may have a substituent(s)".

As the carbon ring, for example, a C3-15 monocyclic, bicyclic or tricyclic carbon ring aryl and the like which may be partially or entirely saturated can be cited. In this case, as the "C3-15 monocyclic, bicyclic or tricyclic carbon ring aryl which may be partially or entirely saturated", for example, cyclopropane, cyclobutane, cyclopentane, cyclohexane, cycloheptane, cyclooctane, cyclononane, cyclodecane, cycloundecane, cyclododecane, cyclotridecane, cyclotetradecane, cyclopentadecane, cyclopentene, cyclohexene, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indane, naphthalene, dihydronaphthalene, tetrahydronaphthalene, perhydronaphthalene, heptalene, perhydroheptalene, biphenylene, as-indacene, s-indacene, acenaphthylene, acenaphthene, fluorene, phenalene, phenanthrene, anthracene and the like can be cited. In addition, the "C3-15 monocyclic, bicyclic or tricyclic carbon ring aryl which may be partially or entirely saturated" also includes a spiro-bonded bicyclic carbon ring and crosslinked bicyclic carbon ring, and their examples include spiro[4.4]nonane, spiro[4.5]decane, spiro[5.5]undecane, bicyclo[2.2.1]heptane, bicyclo[2.2.1]hept-2-ene, bicyclo[3.1.1]heptane, bicyclo[3.1.1]hept-2-ene, bicyclo[2.2.2]octane, bicyclo[2.2.2]oct-2-ene, adamantane, noradamantane and the like.

On the other hand, as the hetero ring, for example, a 3- to 15-membered monocyclic, bicyclic or tricyclic hetero ring aryl which contains from 1 to 4 nitrogen atoms, from 1 to 3 oxygen atoms and/or from 1 to 3 sulfur atoms, a hetero ring which is partially or entirely saturated, a spiro-bonded tricyclic hetero ring, a crosslinked tricyclic hetero ring and the like can be cited. In this case, as the "3- to 15-membered monocyclic, bicyclic or tricyclic hetero ring aryl which contains from 1 to 4 nitrogen atoms, from 1 to 3 oxygen atoms and/or from 1 to 3 sulfur atoms", for example, pyrrole, imidazole, triazole, tetrazole, pyrazole, pyridine, pyrazine, pyrimidine, pyridazine, azepine, diazepine, furan, pyran, oxepin, thiophene, thiaine (thiopyran), thiepine, oxazole, isoxazole, thiazole, isothiazole, furazane, oxadiazole, oxazine, oxadiazine, oxazepine, oxadiazepine, thiadiazole, thiazine, thiadiazine, thiazepine, thiadiazepine, indole, isoindole, benzofuran, isobenzofuran, benzothiophene, isobenzothiophene, indazole, quinoline, isoquinoline, phthalazine, naphthyridine, quinoxaline, quinazoline, cinnoline, benzoxazole, benzothiazole, benzimidazole, benzoxepin, benzoxazepine, benzoxadiazepine, benzothiepine, benzothiazepine, benzothiadiazepine, benzoazepine, benzodiazepine, benzofurazan, benzothiadiazole, benzotriazole, carbazole, acridine, dibenzofuran, dibenzothiophene and the like can be cited. Also, as those which are partially or entirely saturated among the "3- to 15-membered monocyclic, bicyclic or tricyclic (condensed or spiro) hetero rings which contain from 1 to 4 nitrogen atoms, from 1 to 3 oxygen atoms and/or from 1 to 3 sulfur atoms", for example, pyrroline, pyrrolidine, imidazoline, imidazolidine, pyrazoline, pyrazolidine, triazoline, triazolidine, tetrazoline, tetrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrofuran, tetrahydrofuran, dihydropyran, tetrahydropyran, dihydrothiophene, tetrahydrothiophene, dihydrothiaine (dihydrothiopyran), tetrahydrothiaine (tetrahydrothiopyran), dihydrooxazole, tetrahydrooxazole, dihydroioxazole, tetrahydroisoxazole, dihydrothiazole, tetrahydrothiazole, dihydroisothiazole, tetrahydroisothiazole, dihydrooxadiazole, tetrahydrooxadiazole, dihydrothiodiazole, tetrahydrothiodiazole, tetrahydrooxadiazine, tetrahydrothiadiazine, tetrahydrooxazepine, tetrahydrooxadiazepine, pehydroxazepine, perhydrooxadiazepine, tetrahydrothiazepine, tetrahydrothiadiazepine, perhydrothiazepine, perhydrothiadiazepine, morpholine, thiomorpholine, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, dihydrobenzoxazole, perhydrobenzoxazole, dihydrobenzothiazole, perhydrobenzothiazole, dihydrobenzimidazole, perhydrobenzimidazole, dihydrocarbazole, tetrahydrocarbazole, perhydrocarbazole, dihydroacridine, tetrahydroacridine, perhydroacridine, dihydrodibenzofuran, dihydrodibenzothiophene, tetrahydrodibenzofuran, tetrahydrodibenzothiophene, perhydrodibenzofuran, perhydrodibenzothiophene, dioxolan, dioxane, dithiolan, dithian, benzodioxalan, benzodioxane, benzodithiolan, benzodithian, 2,4,6-trioxaspiro[bicyclo[3.3.0]octane-3,1'-cyclohexane], 1,3-dioxolano[4,5-b]chromene, 2-oxabicyclo[2.2.1]heptane and the like can be cited.

Preferred as the "cyclic group" in the "cyclic group (ring 1) which may have a substituent(s)" are, for example, 3- to 10-membered monocyclic or bicyclic cyclic groups and the like, more preferred are, for example, cyclopropane, benzene, cyclohexane, cyclohexene, thiophene, pyrazole, isothiazole, thiazole, imidazole, furan, dihydropyrazole, quinoline, benzodioxane, dioxaindane, benzofuran, pyridine, tetrahydropyran, triazole, pyrrole, oxazole, isoxazole, oxadiazole and the like, particularly preferred are, for example, benzene, pyridine and the like, and especially preferred is benzene.

The "substituent" in the "cyclic group (ring 1) which may have a substituent(s)" is not particularly limited, so long as it is a substituent. As this "substituent", for example, (a) an aliphatic hydrocarbon group which may have a substituent(s), (b) a cyclic group (ring 2) which may have a substituent(s), (c) a substituent selected from the above-described first group, and (d) a substituent selected from the following fourth group and the like, and from 1 to 5 of these optional substituents may be substituted at substitutable positions. In this case, the "aliphatic hydrocarbon group" as the "substituent" in the "aliphatic hydrocarbon group which may have a substituent(s)" has the same meaning as the above-described "straight chain or branched chain C1-8 hydrocarbon group". The "substituent" in the "aliphatic hydrocarbon group which may have a substituent(s)" is not particularly limited, so long as it is a substituent. As this "substituent", for example, substituents selected from (a) a cyclic group (ring 2) which may have a substituent(s), (b) a substituent selected from the above-described first group, and (c) a substituent selected from the following fourth group and the like can be cited, and from 1 to 5 of these optional substituents may be substituted at substitutable positions.

<Fourth Group>

(1) —$SR^{e1}$, (2) —$SO_2R^{e1}$, (3) —$SO_2NR^{f1}R^{f2}$, (4) —$S(O)R^{e1}$, (5) —$OR^{e1}$, (6) —$OCOR^{e1}$, (7) —$NR^{e1}SO_2R^{e2}$, (8) —$NR^{f1}R^{f2}$, (9) —$NR^{e1}COR^{e2}$, (10) —$NR^{e1}COOR^{e2}$ (11) —$NR^{e1}CONR^{f1}R^{f2}$, (12) —$N(SO_2R^{e1})_2$, (13) —$COR^{e1}$, (14) —$COOR^{e1}$, (15) —$CONR^{f1}R^{f2}$, (16) —$CONR^{e1}COR^{e2}$, (17) —$COCOOR^{e1}$, (18) —$B(OR^{e1})_2$, wherein $R^{e1}$, $R^{e2}$, $R^{f1}$ and $R^{f2}$ each independently represents hydrogen, a cyclic group (ring 2) which may have a substituent(s) or an aliphatic hydrocarbon group which may have a substituent(s), or together with the adjacent nitrogen, $R^{f1}$ and $R^{f2}$ represent (1) —C2-6 alkylene, (2) —(C2-6 alkylene)-O—(C2-6 alkylene)-, (3) —(C2-6 alkylene)-S—(C2-6 alkylene)-, (4) —(C2-6 alkylene)-$NR^{N2}$—(C2-6 alkylene)- (wherein $R^{N2}$ represents hydrogen, phenyl or a C1-8 alkyl may be susbtituted with phenyl).

In this case, the "aliphatic hydrocarbon group" in the "aliphatic hydrocarbon group which may have a substituent(s)" represented by $R^{e1}$, $R^{e2}$, $R^{f1}$ and $R^{f2}$ has the same meaning as the above-described "straight chain or branched chain C1-8 hydrocarbon group". The "substituent" in the "aliphatic hydrocarbon group which may have a substituent(s)" is not particularly limited; so long as it is a substituent. As this "substituent", for example, substituents selected from (a) a cyclic group (ring 2) which may have a substituent(s) and (b) a substituent selected from the following fifth group can be cited, and from 1 to 5 of these optional substituents may be substituted at substitutable positions.

<Fifth Group>

(1) halogen, (2) —OR$^{g1}$, (3) —SR$^{g1}$, (4) —NR$^{h1}$R$^{h2}$, (5) —COOR$^{g1}$, (6) —CONR$^{h1}$R$^{h2}$, (7) —NR$^{g1}$COR$^{g2}$, (8) —NR$^{g1}$SO$_2$R$^{g2}$, (9) —N(SO$_2$R$^{g1}$)$_2$, (10) —SO$_2$NR$^{h1}$R$^{h2}$ wherein R$^{g1}$, R$^{g2}$, R$^{h1}$ and R$^{h2}$ have the same meanings as the above-described R$^{e1}$, R$^{e2}$, R$^{f1}$ and R$^{f2}$, respectively; however, each of the R$^{g1}$, R$^{g2}$, R$^{h1}$ and R$^{h2}$ does not represent an aliphatic hydrocarbon group susbtituted with a substituent selected from this group (fifth group).

In the specification the "cyclic group" in the "cyclic group (ring 2) which may have a substituent(s)" has the same meaning as the above-described "cyclic group" in the "cyclic group (ring 1) which may have a substituent(s)".

The "substituent" in the "cyclic group (ring 2) which may have a substituent(s)" is not particularly limited, so long as it is a substituent. As this "substituent", for example, substituents selected from (a) an aliphatic hydrocarbon group which may have a substituent(s), (b) a 3- to 8-membered monocyclic carbon ring or hetero ring which may have a substituent(s), (c) a substituent selected from the above-described first group and (d) a substituent selected from the following sixth group can be cited, and from 1 to 5 of these optional substituents may be substituted at substitutable positions. In this case, the "aliphatic hydrocarbon group" as the "substituent " in the "aliphatic hydrocarbon group which may have a substituent(s)" has the same meaning as the above-described "straight chain or branched chain C1-8 hydrocarbon group". The "substituent" in the "aliphatic hydrocarbon group which may have a substituent(s)" is not particularly limited, so long as it is a substituent. As this "substituent", for example, substituents selected from (a) a 3- to 8-membered monocyclic carbon ring or hetero ring which may have a substituent(s), (b) a substituent selected from the above-described first group and (c) a substituent selected from the following sixth group can be cited, and from 1 to 5 of these optional substituents may be substituted at substitutable positions.

<Sixth Group>

(1) —SR$^{i1}$, (2) —SO$_2$R$^{i1}$, (3) —SO$_2$NR$^{j1}$R$^{j2}$, (4) —S(O)R$^{i1}$, (5) —OR$^{i1}$, (6) —OCOR$^{i1}$, (7) —NR$^{i1}$SO$_2$R$^{i2}$, (8) —NR$^{j1}$R$^{j2}$, (9) —NR$^{i1}$COR$^{i2}$, (10) —NR$^{i1}$COOR$^{i2}$ (11) —NR$^{i1}$CONR$^{j1}$R$^{j2}$, (12) —N(SO$_2$R$^{i1}$)$_2$, (13) —COR$^{i1}$, (14) —COOR$^{i1}$, (15) —CONR$^{j1}$R$^{j2}$, (16) —CONR$^{i1}$COR$^{i2}$, (17) —COCOOR$^{i1}$, (18) —B(OR$^{i1}$)$_2$, wherein R$^{i1}$, R$^{i2}$, R$^{j1}$ and R$^{j2}$ each independently represents hydrogen, a 3- to 8-membered monocyclic carbon ring or hetero ring which may have a substituent(s) or an aliphatic hydrocarbon group which may have a substituent(s), or together with the adjacent nitrogen, R$^{j1}$ and R$^{j2}$ represent (1) —C2-6 alkylene (e.g., methylene, ethylene, trimethylene, tetramethylene, pentamethylene, hexamethylene and isomer groups thereof and the like)-, (2) —(C2-6 alkylene)-O—(C2-6 alkylene)-, (3) —(C2-6 alkylene)-S—(C2-6 alkylene)-, (4) —(C2-6 alkylene)-NR$^{N2}$—(C2-6 alkylene)- (wherein R$^{N2}$ represents the same meaning as described above).

In this case, the "aliphatic hydrocarbon group" in the "aliphatic hydrocarbon group which may have a substituent(s)" represented by R$^{i1}$, R$^{i2}$, R$^{j1}$ and R$^{j2}$ has the same meaning as the above-described "straight chain or branched chain C1-8 hydrocarbon group". The "substituent" in the "aliphatic hydrocarbon group which may have a substituent(s)" represented by R$^{i1}$, R$^{i2}$, R$^{j1}$ and R$^{j2}$ is not particularly limited, so long as it is a substituent. As this "substituent", for example, substituents selected from (a) a 3- to 8-membered monocyclic carbon ring or hetero ring which may have a substituent(s) and (b) a substituent selected from the following seventh group can be cited, and from 1 to 5 of these optional substituents may be substituted at substitutable positions.

<Seventh Group>

(1) halogen, (2) —OR$^{k1}$, (3) —SR$^{k1}$, (4) —NR$^{m1}$R$^{m2}$, (5) —COOR$^{k1}$, (6) —CONR$^{m1}$R$^{m2}$, (7) —NR$^{k1}$COR$^{k2}$, (8) —NR$^{k1}$SO$_2$R$^{k2}$, (9) —N(SO$_2$R$^{k1}$)$_2$, wherein R$^{k1}$, R$^{k2}$, R$^{m1}$ and R$^{m2}$ have the same meanings as the above-described R$^{i1}$, R$^{i2}$, R$^{j1}$ and R$^{j2}$, respectively; however, each of the R$^{k1}$, R$^{k2}$, R$^{m1}$ and R$^{m2}$ does not represent an aliphatic hydrocarbon group susbtituted with a substituent selected from this group (seventh group).

In the specification, as the "3- to 8-membered monocyclic carbon ring or hetero ring" in the "3- to 8-membered monocyclic carbon ring or hetero ring which may have a substituent(s)", for example, a 3- to 8-membered monocyclic carbon ring aryl which may be partially or entirely saturated, a 3- to 8-membered monocyclic hetero ring aryl which contains from 1 to 4 nitrogen atoms, 1 or 2 oxygen atoms and/or from 1 or 2 sulfur atoms, a hetero ring which is partially or entirely saturated, and the like can be cited.

As the "3- to 8-membered monocyclic carbon ring aryl which may be partially or entirely saturated", for example, cyclopropane, cyclobutane, cyclopentane, cyclohexane, cycloheptane, cyclooctane, cyclopentene, cyclohexene, cycloheptene, cyclooctene, cyclopentadiene, cyclohexadiene, cycloheptadiene, cyclooctadiene, benzene and the like can be cited. As the "3- to 8-membered monocyclic hetero ring aryl which contains from 1 to 4 nitrogen atoms, 1 or 2 oxygen atoms and/or from 1 or 2 sulfur atoms", for example, pyrrole, imidazole, triazole, tetrazole, pyrazole, pyridine, pyrazine, pyrimidine, pyridazine, azepine, diazepine, furan, pyran, oxepin, thiophene, thiopyran, thiepine, oxazole, isoxazole, thiazole, isothiazole, furazane, oxadiazole, oxazine, oxadiazine, oxazepine, oxadiazepine, thiadiazole, thiazine, thiadiazine, thiazepine, thiadiazepine and the like can be cited. As the hetero ring which is partially or entirely saturated among the "3- to 8-membered monocyclic hetero ring aryl which contains from 1 to 4 nitrogen atoms, 1 or 2 oxygen atoms and/or from 1 or 2 sulfur atoms", for example, aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxirane, oxetane, dihydrofuran, tetrahydrofuran, dihydropyran, tetrahydropyran, dihydrooxepin, tetrahydrooxepin, perhydrooxepin, thiirane, thietane, dihydrothiophene, tetrahydrothiophene, dihydrothiopyran, tetrahydrothiopyran, dihydrothiepine, tetrahydrothiepine, perhydrothiepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazane, tetrahydrofurazane, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, pehydroxazepine, dihydrooxadiazepine, tetrahydrooxadizepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, dioxolan, dioxane, dithiolan, dithian and the like can be cited.

Preferred as the "3- to 8-membered monocyclic carbon ring or hetero ring" in the "3- to 8-membered monocyclic carbon ring or hetero ring which may have a substituent(s)" are 5 or 6-membered cyclic groups, more preferred are tetrahydropyran, tetrahydrothiopyran, piperidine, benzene, pyridine, pyrimidine, pyrazine, furan, oxazole, thiophene, pyrrole, thiazole and imidazole, and particularly preferred is benzene.

In the present specification, the "substituent" in the "3- to 8-membered monocyclic carbon ring or hetero ring which may have a substituent(s)" is not particularly limited, so long as it is a substituent. As this "substituent", for example, substituents selected from (a) a C1-8 alkyl, (b) a substituent selected from the above-described first group and (c) a substituent selected from the following eighth group and the like can be cited.

<Eighth Group>

(1) —OR$^{n1}$, (2) —NR$^{o1}$R$^{o2}$, (3) —COOR$^{n1}$, (4) —SR$^{n1}$, (5) —CONR$^{o1}$R$^{o2}$, wherein R$^{n1}$, R$^{o1}$ and R$^{o2}$ each independently represents hydrogen, phenyl or a C1-8 alkyl which may be susbtituted with phenyl, or together with the adjacent nitrogen, R$^{o1}$ and R$^{o2}$ represent (1) —C2-6 alkylene, (2) —(C2-6 alkylene)-O—(C2-6 alkylene)-, (3) —(C2-6 alkylene)-S—(C2-6 alkylene)-, (4) —(C2-6 alkylene)-NR$^{N2}$—(C2-6 alkylene)- (wherein R$^{N2}$ represents the same meaning as described above).

In the present specification, the "cyclic group which may have a substituent(s)" has the same meaning as the above-described "cyclic group (ring 1) which may have a substituent(s)".

In the present specification, the ring A represents a 5- to 8-membered cyclic group which may have a substituent(s), and this "substituent" is not particularly limited, so long as it is a substituent. Specifically, the groups represented by R$^2$, R$^3$, R$^4$ and R$^5$ which are described below, oxo and the like can be exemplified, and from 1 to 8 of these may be substituted an substitutable positions. In addition, the ring A may be further condensed with a ring B which is described later at a condensable position.

In the present specification, as the "5- to 8-membered cyclic group" in the "5- to 8-membered cyclic group which may have a substituent(s)" represented by the ring A, for example, a 5-8-membered carbon ring, a 5-8-membered hetero ring and the like can be cited.

As the 5- 8-membered carbon ring, for example, a partially or entirely saturated C5-8 monocyclic carbon ring aryl and the like can be cited. As the "partially or entirely saturated C5-8 monocyclic carbon ring aryl", cyclopentane, cyclohexane, cycloheptane, cyclooctane, cyclopentene, cyclohexene, cycloheptene, cyclooctene, cyclopentadiene, cyclohexadiene, cycloheptadiene, cyclooctadiene and the like can be cited. In addition, a crosslinked carbon ring is also included in the "partially or entirely saturated C5-8 monocyclic carbon ring aryl", and its examples include bicyclo[3.1.]heptane, bicyclo[2.2.]heptane, adamantane and the like.

Preferred as the 5- to 8-membered carbon ring is a partially or entirely saturated C5-6 monocyclic carbon ring aryl, and illustratively, for example,

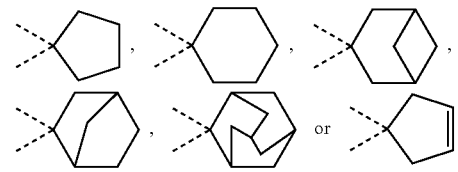

and the like can be cited.

On the other hand, as the 5- to 8-membered hetero ring, for example, a "5- to 8-membered nitrogen-containing hetero ring" which contains at least 1 nitrogen atom and a "5- to 8-membered nitrogen-un-containing hetero ring" which does not contain nitrogen atom can be cited.

As the "5- to 8-membered nitrogen-containing hetero ring", for example, among 5- to 8-membered monocyclic hetero ring aryl which contains at least 1 nitrogen atom and may further contain from 1 to 5 hetero atoms selected from nitrogen atom, oxygen atom and/or sulfur atom, a partially or entirely saturated hetero ring and the like can be cited. As the "partially or entirely saturated hetero ring among 5- to 8-membered monocyclic hetero ring aryl which contains at least 1 nitrogen atom and may further contain from 1 to 5 hetero atoms selected from nitrogen atom, oxygen atom and/or sulfur atom", for example, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazane, tetrahydrofurazane, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxazinan, thiazinan, dioxazine, oxazepan, tetrahydrooxazepin and the like can be cited. Preferred as the "5- to 8-membered nitrogen-containing hetero ring" are those which are partially or entirely saturated, among 5- to 7-membered monocyclic hetero ting aryl compounds which contain 1 or 2 nitrogen atoms and further contain 1 or 2 oxygen atoms and/or 1 or 2 sulfur atoms, and for example,

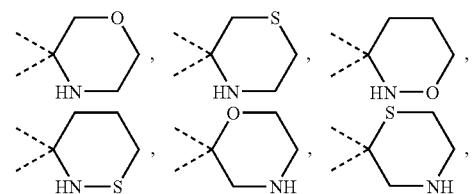

-continued

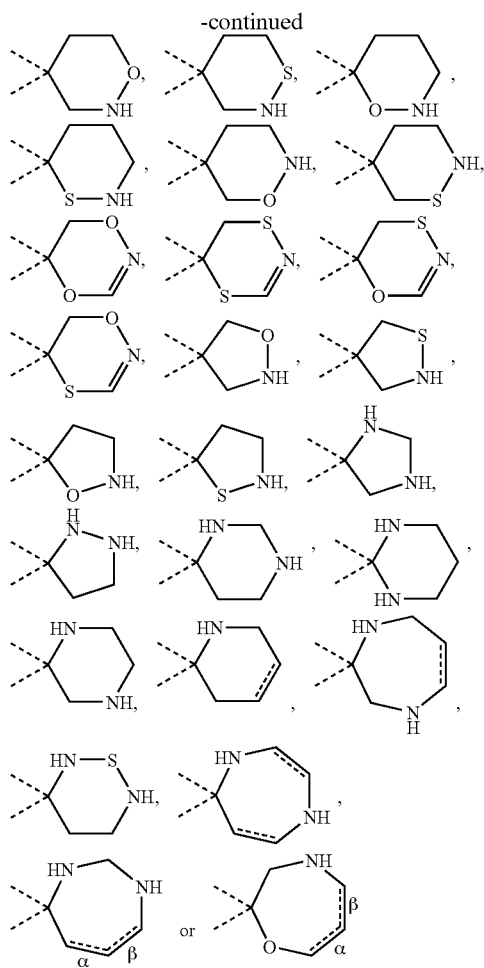

(however, α and β do not simultaneously represent a double bond) and the like can be cited.

On the other hand, as the "5- to 8-membered nitrogen-un-containing hetero ring", a for example, a partially or entirely saturated hetero ring among 5- to 8-membered monocyclic hetero ring aryl which contains 1 to 6 hetero atoms selected from oxygen atom and/or sulfur atom, and the like can be cited. As the "partially or entirely saturated hetero ring among 5- to 8-membered monocyclic hetero ring aryl which contains 1 to 6 hetero atoms selected from oxygen atom and/or sulfur atom", for example, dihydrofuran, tetrahydrofuran, dihydropyran, tetrahydropyran, dihydrooxepin, tetrahydrooxepin, perhydrooxepin, dihydrothiophene, tetrahydrothiophene, dihydrothiopyran, tetrahydrothiopyran, dihydrothiepine, tetrahydrothiepine, perhydrothiepine, oxathian, dioxolan, dioxane, dithiolan, dithian, oxathiolan and the like can be cited.

Preferred as the "5- to 8-membered nitrogen-un-containing hetero ring" are those which are partially or entirely saturated among 5- or 6-membered monocyclic hetero ring aryl which contains 1 or 2 oxygen atoms and/or 1 or 2 sulfur atoms, and illustratively, for example,

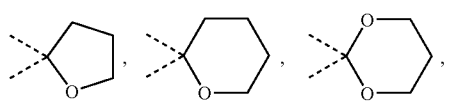

-continued

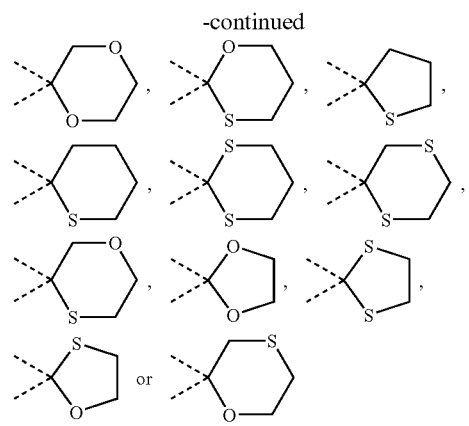

and the like can be cited.

Preferred as the ring A is a 5- to 8-membered hetero ring which may have a substituent(s), more preferred is a 5- to 8-membered nitrogen-containing hetero ring which may have a substituent(s), and particularly preferred is a 5- to 7-membered nitrogen-containing hetero ring which may have a substituent(s).

Preferred as the "5- to 7-membered nitrogen-containing hetero ring which may have a substituent(s)" are imidazolidine, pyrazolidine, piperazine, piperidine, tetrahydropyridine perhydropyrimidine, tetrahydropyrimidine, tetrahydrodiazepine, perhydrodiazepine, tetrahydropyrimidine condensed with ring B, perhydropyrimidine condensed with ring B, tetrahydrodiazepine condensed with ring B, perhydrodiazepine condensed with ring B, thiadiazinan, oxazepan, tetrahydrooxazepin and tetrahydrooxazepin condensed with ring B, which may have a substituent(s), more preferred are

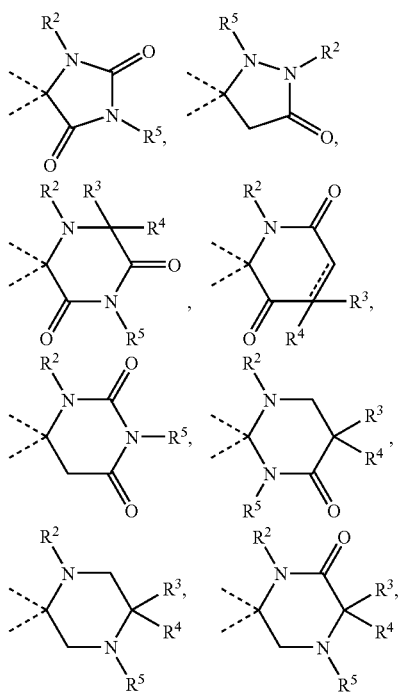

-continued

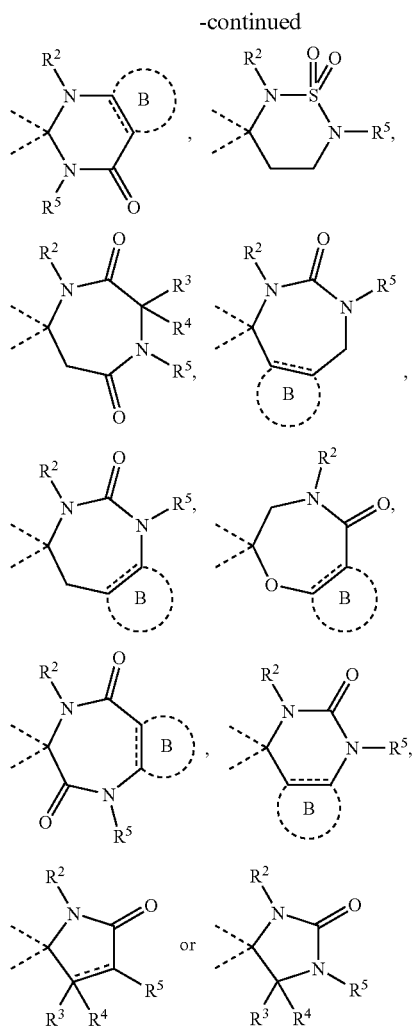

in the formulae, all symbols have the same meanings as those described below, and particularly preferred are

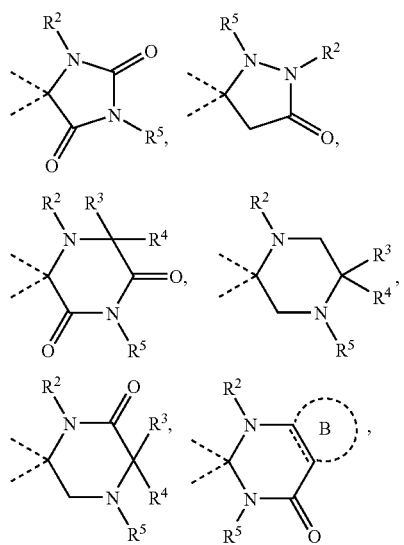

-continued

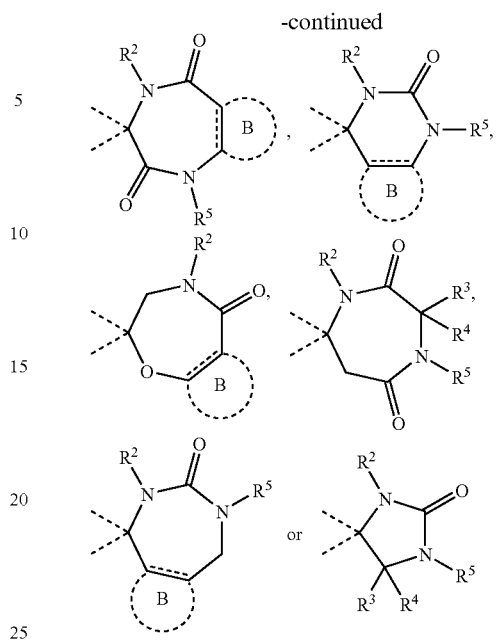

wherein all of the symbols have the same meanings which are described below.

In the present invention, those in which ring A is not condensed with ring B are desirable.

In the present specification, the "aliphatic hydrocarbon group" in the "aliphatic hydrocarbon group which may have a substituent(s)" represented by $R^2$, $R^3$, $R^4$ and $R^5$ has the same meaning as the above-described "straight chain or branched chain C1-8 hydrocarbon group". The "substituent" in the "aliphatic hydrocarbon group which may have a substituent(s)" is not particularly limited, so long as it is a substituent.

As this "substituent", for example, (a) a substituent selected from the above-described first group, (b) a substituent selected from the above-described second group and (c) a cyclic group which may have a substituent(s), and the like can be cited, and from 1 to 5 of these optional substituents may be substituted at substitutable positions. In this case, the "cyclic group which may have a substituent(s)" as the substituent has the same meaning as the above-described "cyclic group (ring 1) which may have a substituent(s)".

Preferred as the "aliphatic hydrocarbon group" in the "aliphatic hydrocarbon group which may have a substituent(s)" represented by $R^2$, $R^3$, $R^4$ and $R^5$ are aliphatic hydrocarbon group having from 1 to 5 carbon atoms, more preferred are methyl, ethyl, propyl, isopropyl, butyl, sec-butyl, tert-butyl, pentyl, 1-butenyl, 2-butenyl, 1-butynyl and 2-butynyl, and particularly preferred are isopropyl, butyl, sec-butyl and tert-butyl.

In the present specification, the hydroxyl which may be protected, carboxy which may be protected and carbamoyl which may be substituted, represented by $R^2$, $R^3$, $R^4$ and $R^5$ have the same meanings as $-OR^{a1}$, $-COOR^{a1}$ and $-CONR^{b1}R^{b2}$ (symbols in the groups represent the same meanings as described above), respectively, cited in the above-described second group.

In the present specification, the ring B represents "3- to 8-membered monocyclic carbon ring or hetero ring which may have a substituent(s)", and the "3- to 8-membered monocyclic carbon ring or hetero ring" has the same meaning as the "3- to 8-membered monocyclic carbon ring or hetero ring" in the above-described "3- to 8-membered monocyclic carbon ring or hetero ring which may have a substituent(s)" represented by $R^{i1}$, $R^{j2}$, $R^{j1}$ and $R^{j2}$. Also, the "substituent" in the "3- to 8-membered monocyclic carbon ring or hetero ring which may have a substituent(s)" has the same meaning as the "substituent" in the above-described "cyclic group which may have a substituent(s)" represented by $R^1$.

Preferred as the "3- to 8-membered monocyclic carbon ring or hetero ring" of the "3- to 8-membered monocyclic carbon ring or hetero ring which may have a substituent(s)" represented by ring B is a 5- or 6-membered cyclic group, more preferred is

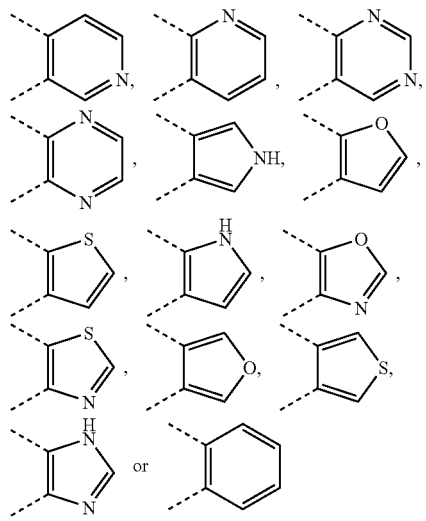

and particularly preferred is benzene.

In the present specification, the aliphatic hydrocarbon group which may have a substituent(s), hydroxyl which may be protected, carboxy which may be protected, carbamoyl which may be protected and cyclic group which may have a substituent(s), represented by $Q^1$ and $Q^2$ have the same meanings as the above-described aliphatic hydrocarbon group which may have a substituent(s), hydroxyl which may be protected, carboxy which may be protected, carbamoyl which may be protected and cyclic group which may have a substituent(s), represented by $R^2$ and $R^5$, respectively.

In the present specification, the aliphatic hydrocarbon group which may have a substituent(s), hydroxyl which may be protected, carboxy which may be protected, carbamoyl which may be protected and cyclic group which may have a substituent(s), represented by $R^{N4}$, $R^{41}$, $R^{42}$ and $R^{42}$ have the same meanings as the above-described aliphatic hydrocarbon group which may have a substituent(s), hydroxyl which may be protected, carboxy which may be protected, carbamoyl which may be protected and cyclic group which may have a substituent(s), represented by $R^2$, $R^3$, $R^4$ and $R^5$, respectively.

In the present specification, the aliphatic hydrocarbon group which may have a substituent(s), hydroxyl which may be protected, carboxy which may be protected, carbamoyl which may be protected and cyclic group which may have a substituent(s), represented by $Q^{41}$ and $Q^{42}$ have the same meanings as the above-described aliphatic hydrocarbon group which may have a substituent(s), hydroxyl which may be protected, carboxy which may be protected, carbamoyl which may be protected and cyclic group which may have a substituent(s), represented by $R^2$ and $R^5$, respectively.

In the present specification, the arrows described in the formula represented by $A^A$ show the bondable positions with $N^4$ and mean that either one of them directly binds with the nitrogen shown by $N^4$.

In the present invention, all of the respective groups represented by $R^1$, $R^2$, $R^3$, $R^4$, $R^5$ and ring A are desirable. Those which are described in Examples are particularly desirable.

In the present invention, preferred as $R^1$ is an aliphatic hydrocarbon group which may have a substituent(s), more preferred is an aliphatic hydrocarbon group which may have a "cyclic group which may have a substituent(s)" as the substituent. In this case, preferred as the "aliphatic hydrocarbon group" are, for example, an aliphatic hydrocarbon group having from 1 to 10 carbon atoms and the like, more preferred are, for example, an alkyl having from 1 to 6 carbon atoms, an alkenyl having from 2 to 6 carbon atoms and the like, and particularly preferred are, for example, an alkyl having from 1 to 6 carbon atoms and the like. Especially, an alkyl having from 1 to 4 carbon atoms is desirable, and methyl and ethyl are more desirable. In addition, preferred as the "cyclic group" in the "cyclic group which may have a substituent(s)" are, for example, 3- to 10-membered monocyclic or bicyclic cyclic group and the like, more preferred are, for example, C3-6 cycloalkyl, C4-6 cycloalkenyl, benzene, pyrazole, thiazole, furan, thiophene, quinoline, benzodioxane, dioxaindane, benzofuran, imidazole, isothiazole, dihydropyrazole, pyridine, tetrahydropyran, triazole, pyrrole, oxazole, isoxazole, oxadiazole and the like, and particularly preferred are, for example, benzene, pyridine and the like, of which benzene is especially desirable. Preferred as the "substituent" in the "cyclic group which may have a substituent(s)" are, for example, C1-6 alkyl which may have a substituent(s), cyano, halogen, benzene which may have a substituent(s), amino which may be substituted, dihydroxyboryl which may be substituted, —NHCO—(C1-4 alkyl which may have a substituent(s)) and —O—(C1-4 alkyl which may have a substituent(s)).

As more illustrative groups as $R^1$ of the present invention, for example, —(C1-6 alkyl)-(benzene which may have a substituent(s)), —(C1-6 alkyl)-(pyridine which may have a substituent(s)), —(C1-6 alkyl)-(pyrazole which may have a substituent(s)), —(C1-6 alkyl)-(C4-6 cycloalkyl which may have a substituent(s)), —(C1-6 alkyl)-(C4-6 cycloalkenyl which may have a substituent(s)), —(C1-6 alkyl)-(thiazole which may have a substituent(s)), —(C1-6 alkyl)-(furan which may have a substituent(s)), —(C1-6 alkyl)-(thiophene which may have a substituent(s)), —(C1-6 alkyl)-(quinoline which may have a substituent(s)), —(C1-6 alkyl)-(benzodioxane which may have a substituent(s)), —(C1-6 alkyl)-(dioxaindane which may have a substituent(s)), —(C1-6 alkyl)-(benzofuran which may have a substituent(s)), —(C1-6 alkyl)-(imidazole which may have a substituent(s)), —(C1-6 alkyl)-(isothiazole which may have a substituent(s)), —(C1-6 alkyl)-(dihydropyrazole which may have a substituent(s)) and the like can be cited, more preferably, for example, —(C1-4 alkyl)-(C4-6 cycloalkenyl)-(C1-6 alkyl which may have a substituent(s)), —(C1-4 alkyl)-(quinoline), —(C1-4 alkyl)-(dioxaindane), —(C1-4 alkyl)-(cyclopropane), —(C1-4 alkyl)-(thiazole), —(C1-4 alkyl)-(thiophene), —(C1-4 alkyl)-(benzene), —(C1-4 alkyl)-(pyridine), —(C1-4 alkyl)-(furan), —(C1-4 alkyl)-(benzodioxane), —(C1-4 alkyl)-(benzofuran), —(C1-4 alkyl)-(benzene which may be substituted with cyano), —(C1-4 alkyl)-(benzene which may be substituted with halogen)-(C1-4 alkyl)-(benzene)-(C1-4 alkyl which may have a substituent(s)), —(C1-4 alkyl)-(benzene)-(C1-4 alkoxy which may have a substituent(s)), —(C1-4 alkyl)-(benzene)-(benzene which may have a substituent(s)), —(C1-4 alkyl)-(benzene)-(amino which may have a substituent(s)), —(C1-4 alkyl)-(benzene)-(dihydroxyboryl which may have a substituent(s)), —(C1-4 alkyl)-(benzene)-NHCO—(C1-4 alkoxy which may have a substituent(s)), —(C1-4 alkyl)-(benzene)-O—(C1-4 alkyl which may have a substituent(s))-(benzene which may have a substituent(s)), —(C1-4 alkyl)-(benzene)-(C1-4 alkyl which may have a substituent(s))-(benzene which may have a substituent(s)), —(C1-4 alkyl)-(benzene)-CO-(benzene which may have a substituent(s)), —(C1-4 alkyl)-(benzene)-O—(C1-4 alkyl which may have a substituent(s))-(amino which may have a substituent(s)), —(C1-4 alkyl)-(benzene)-O—(benzene which may have a substituent(s)), —(C1-4 alkyl)-(pyridine)-O-(benzene which may have a substituent(s)), —(C1-4 alkyl)-(benzene)-O-(pyridine which may have a substituent(s)), —(C1-4 alkyl)-(pyridine)-O-(pyridine which may have a substituent(s)), —(C1-4 alkyl)-(imidazole)-(benzene which may have a substituent(s)), —(C1-4 alkyl)-(dihydropyrazole which may have a substituent(s))-(benzene which may have a substituent(s)), —(C1-4 alkyl)-(pyrazole which may have a substituent(s))-(benzene which may have a substituent(s)) and the like can be cited, and particularly preferably, 1,3-thiazol-2-ylmethyl, 1,5-dimethyl-3-oxo-2-phenyl-2,3-dihydro-1H-pyrazol-4-ylmethyl, 2-(4-isopropylbenzyl)-propyl, 2,4,6-trimethoxybenzyl, 2,4-dimethoxybenzyl, 2,6-dimethoxybenzyl, 2-phenylimidazol-5-ylmethyl, 2-phenylethyl, 2-benzyloxybenzyl, 2-methoxybenzyl, 3-(furan-2-yl)-2-propenyl, 3,5-dimethyl-1-phenyl-1H-pyrazol-4-ylmethyl, 3-cyanobenzyl, 3-phenylpyrazol-4-ylmethyl, 3-phenylpropyl, 3-phenoxybenzyl, 4-(3-(N,N-dimethylamino)propyloxy)benzyl, 4-(4-hydroxy-4-methylpentyl)cyclohex-3-ene-1-ylmethyl, 4-(4-methylsulfonylamino)-phenoxybenzyl, 4-(N,N-dimethylamino)benzyl, 4-(dihydroxyboryl)benzyl, 4-(methylcarbonylamino)benzyl, 4-chlorobenzyl, 4-phenylbenzyl, 4-phenoxybenzyl, 4-fluorobenzyl, 6-methyl-2,2-dimethylcyclohex-1-en-1-ylethyl, quinoline-2-ylmethyl, dioxaindan-4-ylmethyl, cyclopropane-1-ylmethyl, thiophen-2-ylmethyl, furan-2-ylmethyl, benzyl, benzodioxan-6-ylmethyl, benzofuran-2-ylmethyl and the like can be cited.

In addition, the groups exemplified as desirable $R^1$ in WO 01/40227 and WO 02/74770 can also be cited as desirable $R^1$ in the present invention. Among the compounds represented by formula (1) having such an $R^1$, more preferably, a compound which has, as $R^1$, an alkyl having from 1 to 6 carbon atoms substituted with a 3- to 10-membered monocyclic or bicyclic cyclic group which may have a substituent(s), and the like can be exemplified. Particularly preferred is a compound having an alkyl having from 1 to 6 carbon atoms as $R^1$ which may be substituted with benzene which may have a substituent(s), cyclohexane which may have a substituent(s), pyridine which may have a substituent(s), cyclopropane which may have a substituent(s), thiazole which may have a substituent(s), thiophene which may have a substituent(s), furan which may have a substituent(s), isoxazole which may have a substituent(s), oxadiazole which may have a substituent(s), pyrrole which may have a substituent(s), dihydrobenzodioxine which may have a substituent(s), pyrazole which may have a substituent(s), imidazole which may have a substituent(s) or the like.

In addition, according to the present invention, those which are represented by the following formula

wherein ring 1 represents the above-described "cyclic group (ring 1) which may have a substituent(s)", ring 2 represents the above-described "cyclic group (ring 2) which may have a substituent(s)", $Y^A$ represents a bond, —CH$_2$—, —CH$_2$CH$_2$—, —O—, —S—, —CO—, —S(O)—, —SO$_2$—, —CH(OH)—, —NR$^{f1}$—, —CONR$^{f1}$, —NR$^{e1}$CO—, —CH$_2$O—, —OCH$_2$—, —CH=CH—, —CONR$^{f1}$CH$_2$—, —CH$_2$CONR$^{h1}$, —CH$_2$NR$^{g1}$CO—, —NR$^{e1}$COCH$_2$—, —NR$^{e1}$SO$_2$—, —SO$_2$NR$^{f1}$—, —SO$_2$NR$^{f1}$CH$_2$—, —CH$_2$SO$_2$NR$^{h1}$, —CH$_2$NR$^{g1}$SO$_2$— or —NR$^{e1}$SO$_2$CH$_2$—, and all of $R^{f1}$, $R^{e1}$, $R^{h1}$ and $R^{g1}$ have the same meanings as those defined above, can also be exemplified as preferred $R^1$. In this case, the bond, —O—, —CH$_2$—, —CO— and the like can be cited as preferred $Y^A$. As ring 1 and ring 2, "5- to 10-membered carbon ring aryl or hetero ring aryl" and the like can be preferably cited. As the "5- to 10-membered carbon ring aryl or hetero ring aryl", for example, "5- or 6-membered carbon ring aryl or hetero ring aryl" and the like can be preferably cited, and particularly preferably, for example, rings such as benzene, pyrrole, imidazole, triazole, tetrazole, pyrazole, pyridine, pyrazine, pyrimidine, pyridazine, triazine, furan, thiophene, oxazole, isoxazole, thiazole, isothiazole, furazane, oxadiazole and thiadiazole can be cited. As described above, these cyclic groups may have a substituent(s), and particularly, those in which carboxy, amido or sulfonamido is substituted on the ring 2 are desirable. In addition, as the substituents of ring 1 and ring 2, for example, an aliphatic hydrocarbon group which may have a substituent(s), alkoxy, carboxy, alkanoylamido and the like can be cited, and as the more desirable substituents, for example, an aliphatic hydrocarbon group, alkoxy and the like can be cited. In the present invention, $R^1$ having a combination thereof is more desirable.

In the present invention, preferred as the $R^2$, $R^3$, $R^4$ and $R^5$ are hydrogen, a 4- to 6-membered carbon ring which may have a substituent(s) and a C1-6 aliphatic hydrocarbon group, more preferred are hydrogen, —(C1-6 alkyl which may have a substituent(s)), —(C2-6 alkenyl which may have a substituent(s)), —(C2-6 alkynyl which may have a substituent(s)), -(benzene which may have a substituent(s)), —(C1-6 alkyl)-(C4-6 cycloalkyl which may have a substituent(s)), —(C1-6 alkyl)-(benzene which may have a substituent(s)), and —(C1-6 alkyl)-NHCOO—(C1-6 alkyl which may have a substituent(s)) -(benzene which may have a substituent(s)), and particularly preferred are hydrogen, —(C1-6 alkyl), —(C2-6 alkenyl), —(C2-6 alkynyl), —(C1-4 alkyl)-COO—(C1-4 alkyl), —(C1-4 alkyl)-(C4-6 cycloalkyl), —(C1-4 alkyl)-(benzene) and —(C1-6 alkyl)-NHCOO—(C1-4 alkyl)-(benzene). In particular, hydrogen, propyl, butyl, sec-butyl, cyclohexylmethyl, benzyl and phenylethyl are desirable.

In the present invention, a compound of formula (I) which contains a combination of those which are enumerated in the foregoing as preferred groups and preferred rings is desirable.

In the present invention, all isomers are included therein unless otherwise noted. For example, straight chain and branched chain compounds are included in alkyl, alkoxy, alkylene and the like. In addition, isomers related to double bond, ring and condensed ring (E, Z, cis and trans forms), isomers due to the presence of asymmetric carbon (R and S forms, α and β forms, enantiomer, diastereomer), optically active substances having optical rotatory power (D, L, d and l forms), polar substances due to chromatographic separation (high polar substance, low polar substance), equilibrium compounds, mixtures thereof at optional ratio and racemic mixtures are also included therein.

In the present invention, prodrug of the compound represented by formula (I) means a compound which is converted into the compound represented by formula (I) in the living body through the reaction by enzyme, gastric acid or the like. As the prodrug of the compound represented by formula (I), for example, when the compound represented by formula (I) has amino, a compound in which the amino is acylated, alkylated or phosphorylated (e.g., a compound in which amino of the compound represented by formula (I) is converted into eicosanoyl, alanyl, pentylaminocarbonyl, (5-methyl-2-oxo-1,3-dioxolen-4-yl)methoxycarbonyl, tetrahydrofuranyl, pyrrolidylmethyl, pivaloyloxymethyl, acetoxymethyl, tert-butyl or the like); when the compound represented by formula (I) has hydroxyl, a compound in which the hydroxyl is acylated, alkylated, phosphorylated or borated (e.g., a compound in which carboxy of the compound represented by formula (I) is converted into acetyl, palmitoyl, propanoyl, pivaloyl, succinyl, fumaryl, alanyl, dimethylaminomethylcarbonyl or the like); when the compound represented by formula (I) has carboxy, a compound in which the carboxy is esterificated or amidated (e.g., a compound in which carboxy of the compound represented by formula (I) is converted into ethyl ester, phenyl ester, carboxymethyl ester, dimethylaminomethyl ester, pivaloyloxymethyl ester, ethoxycarbonyloxyethyl ester, phthalidyl ester, (5-methyl-2-oxo-1,3-dioxolen-4-yl) methyl ester, cyclohexyloxycarbonylethyl ester, a methylamidated compound or the like); and the like can be cited. These compounds can be produced by conventionally known methods. Also, prodrugs of the compound represented by formula (I) may be either hydrates or non-hydrates. Also, prodrugs of the compound represented by formula (I) may be those which change to the compound represented by formula (I) under physiological conditions described in *Iyakuhin no Kaihatsu* (*Development of Medicines*), volume 7, "Bunshi Sekkei (Molecular Engineering)" pp. 163-198, published by Hirokawa Shoten. In addition, the compound represented by formula (I) may be labeled with an isotope (e.g., $^3$H, $^{14}$C, $^{35}$S, $^{125}$I or the like) or the like.

Salts:

In the present invention, all of those which are pharmacologically acceptable are included in the salts of the compound represented by formula (I). It is desirable that the pharmacologically acceptable salts have no toxicity and are water-soluble. As appropriate salts, for example, salts of alkali metals (potassium, sodium, lithium and the like), salts of alkaline earth metals (calcium, magnesium and the like), ammonium salts (tetramethylammonium salt, tetrabutylammonium salt and the like), salts of organic amines (triethyl amine, methylamine, dimethylamine, cyclopentyl amine, benzylamine, phenethylamine, piperidine, monoethanolamine, diethanolamine, tris(hydroxymethyl)methylamine, lysine, arginine, N-methyl-D-glucamine and the like) and acid addition salts [inorganic acid salts (hydrochloride, hydrobromide, hydroiodide, sulfate, phosphate, nitrate and the like), organic acid salts (acetate, trifluoroacetate, lactate, tartarate, oxalate, fumarate, maleate, benzoate, citrate, methanesulfonate, ethanesulfonate, benzenesulfonate, toluenesulfonate, isethionate, glucuronate, gluconate and the like) and the like] can be cited.

In the present invention, the compound represented by formula (I) may be an N-oxide or quaternary ammonium salt, The N-oxide of the compound represented by formula (I) means that nitrogen atom of the compound represented by formula (I) is oxidized. Also, the N-oxide of the compound of the present invention may be in the form of the above-described alkali (alkaline earth) metal salt, ammonium salt, organic amine salt or acid addition salt. The quaternary ammonium salts of the compound represented by formula (I) represent those in which the nitrogen atom of the compound represented by formula (I) is quaternarized by $R^0$ ($R^0$ represents C1-8 alkyl or C1-8 alkyl substituted with phenyl). In addition, the quaternary ammonium salts of the compound of the present invention may be in the form of the above-described alkali (alkaline earth) metal salt, ammonium salt, organic amine salt, acid addition salt or N-oxide.

As the appropriate solvates of the compound represented by formula (I), for example, solvates with water, an alcohol solvent (ethanol or the like) and the like can be cited. it is desirable that the solvates are nontoxic and soluble in water. In addition, solvates of the above-described alkali (alkaline earth) metal salt, ammonium salt, organic amine salt, acid addition salt, N-oxide or quaternary salt of the compound of the present invention are also included in the solvates of the compound of the present invention.

The compound of the present invention can be converted into the above-described salts, the above-described N-oxides, the above-described quaternary ammonium salts or the above-described solvates by conventionally known methods.

Production Methods of the Compounds of the Present Invention:

The compounds of the present invention represented by formula (I) can be produced by the methods of (A) to (H), (J) and (K) shown above, corresponding methods thereof or the methods described in Examples. In addition, the compounds of the present invention represented by formula (I) can also be produced by a method similar to the method described in WO 01/40227, a method similar to the method described in WO 02/74770, conventionally known methods or optionally improved methods of these methods. In this connection, in the following respective production methods, the material compounds may be used as salts. As such salts, those which are described as the above-described salts of formula (I) can be used.

(A) Among the compounds of the present invention represented by formula (I), a compound in which $R^1$ does not represent hydrogen, namely a compound represented by formula (I-1):

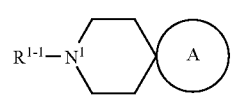

(I-1)

(wherein $R^{1-1}$ has the same meaning as $R^1$, with the proviso that $R^{1-1}$ does not represent hydrogen, and $N^1$ represents nitrogen) can be produced, for example, by the method described in the following reaction scheme (I) using, among the compounds of the present invention represented by formula (I), a compound in which $R^1$ represents hydrogen, namely a compound represented by formula (I-2):

 (I-2)

(wherein all symbols have the same meanings as those defined above). Also, in addition to this reaction, it can also be produced by the methods described in detail in WO 02/74770, conventionally known methods or methods in which these methods are optionally improved.

Reaction Scheme (1)

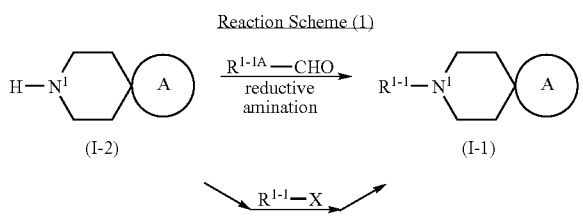

In the reaction scheme (I), $R^{1-1A}$ represents a C1-17 aliphatic hydrocarbon group which may have a substituent(s), X represents a leaving group (e.g., chlorine, bromine, iodine, p-toluenesulfonyloxy, methanesulfonyloxy, trifluoromethanesulfonyloxy,

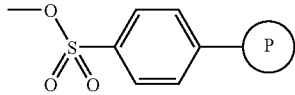

(wherein

represents a polystyrene resin (e.g., 1 to 10% divinylbenzene copolymer or the like) or the like), and other symbols have the same meanings as those defined above.

Among the compounds represented by formula (I-1), a compound in which $R^{1-1}$ represents a C1-18 aliphatic hydrocarbon group which may have a substituent(s), and when $R^{1-1}$ bonds with $N^1$, it bonds via —$CH_2$—, can be produced by subjecting the compound represented by formula (I-2) and a compound represented by formula (A-1)

$$R^{1-1A}\text{—CHO} \tag{A-1}$$

(wherein all symbols have the same meanings as those defined above) to a reductive amination reaction.

This reductive amination reaction is conventionally known and is carried out, for example, at a temperature of from 0 to 40° C. in an organic solvent (e.g., dichloroethane, dichloromethane, N,N-dimethylformamide, acetic acid, a mixture thereof or the like) in the presence of a reducing agent (e.g., sodium borohydride, sodium triacetoxyborohydride, sodium cyanoborohydride or the like).

In addition, this reductive amination reaction can also be carried out in the case of a compound in which nitrogen in $R^1$ represents N-oxide.

In addition, the compound represented by formula (I-1) can also be produced by subjecting the compound represented by formula (I-2) and a compound represented by formula (A-2)

$$R^{1-1}\text{—X} \tag{A-2}$$

(wherein all symbols have the same meanings as those defined above) to a reaction.

This reaction with the compound represented by formula (A-2) is conventionally known and can be produced by subjecting to, for example,
1) alkylation reaction when $R^{1-1}$ is an aliphatic hydrocarbon group,
2) amidation reaction when $R^{1-1}$ is a group containing carbonyl,
3) sulfoneamidation reaction when $R^{1-1}$ is a group containing sulfonyl.

Also, in addition to the above, the bond formation reaction of nitrogen with $R^{1-1}$ can be carried out, for example, by the method described in *Comprehensive Organic Transformations: A Guide to Functional Group Preparations*, 2nd Edition edited by Richard C. Larock, John Wiley & Sons Inc (1999).

Although it can be easily understood by those skilled in the art, the intended compound of the present invention can be easily produced by properly using each reaction on response to respective $R^{1-1}$.
1) The alkylation reaction is conventionally known, and can be carried out, for example, at a temperature of from −78 to 100° C. in an organic solvent (e.g., aromatic hydrocarbons such as benzene, toluene and xylene; halogenated hydrocarbons such as dichloromethane and chloroform; saturated hydrocarbons such as hexane, heptane and cyclohexane; ethers such as diethyl ether, tetrahydrofuran and dioxane; ketones such as acetone and methyl ethyl ketone; nitriles such as acetonitrile; sulfoxides such as dimethyl sulfoxide; amides such as N,N-dimethylformamide; esters such as ethyl acetate are used, wherein these solvents may be used alone or by mixing two or more of them, if necessary, at a ratio of, for example, from 1:1 to 1:10), by adding thereto an amine, a base (e.g., hydrides of alkali metals or alkaline earth metals such as sodium hydride and potassium hydride; alkyl lithiums such as butyl lithium, sec-butyl lithium and tert-butyl lithium; alkoxides of alkali metals such as sodium methoxide and sodium ethoxide; inorganic bases of alkali metals such as metallic sodium and metallic potassium; alkylamines such as triethylamine, tributylamine and diisopropylethylamine; aromatic amines such as N,N-dimethylaniline, pyridine, lutidine, collidine and 4-(dimethylamino)pyridine; organic bases such as DBU (1,8-diazabicyclo[5.4.0]undecane-7); metal amides such as lithium diisopropylamide, lithium hexamethyldisilazide, potassium hexamethyldisilazide and sodium hexamethyldisilazide; and the like) and a compound having a leaving group.
2) The amidation reaction is conventionally known, and for example,
(1) a method which uses an acid halide,
(2) a method which uses a mixed acid anhydride,
(3) a method which uses a condensing agent and the like can be cited.

In illustratively describing these methods,
(1) the method which uses an acid halide is carried out, for example, in an organic solvent (e.g., halogenated hydrocarbons such as chloroform and dichloromethane; ethers such as diethyl ether, tetrahydrofuran and dioxane; acid amids such as dimethylformamide; and the like are used, wherein these solvents may be used alone or by mixing two or more of them, if necessary, at a ratio of, for example, from 1:1 to 1:10), or without solvent, by allowing a carboxylic acid to react with an acid halide forming agent (e.g., oxalyl chloride, thionyl chloride, phosphorus pentachloride, phosphorus trichloride or the like) at from −20° C. to reflux temperature, and then allowing the thus obtained acid halide to react with an amine at from 0 to 40° C. in the presence of a base (e.g., alkylamines such as triethylamine, tributylamine and diisopropylethylamine; aromatic amines such as N,N-dimethylaniline, pyridine and 4-(dimethylamino)pyridine; and the like). In addition, this can also be carried out in an organic solvent (e.g., diethyl ether, dioxane, tetrahydrofuran and the like are used, wherein these solvents may be used alone or by mixing two or more of them, if necessary, at a ratio of, for example, from 1:1 to 1:10), by allowing the thus obtained acid halide to react with an amine at from 0 to 40° C. using an alkali aqueous solution (e.g., sodium bicarbonate aqueous solution, sodium hydroxide solution or the like).

(2) The method which uses a mixed acid anhydride is carried out, for example, in an organic solvent (e.g., halogenated hydrocarbons such as chloroform and dichloromethane; ethers such as diethyl ether, tetrahydrofuran and dioxane; acid amides such as dimethylformamide, and the like are used, wherein these solvents may be used alone or by mixing two or more of them, if necessary, at a ratio of, for example, from 1:1 to 1:10), or without solvent, by allowing a carboxylic acid to react with an acid halide (e.g., pivaloyl chloride, tosyl chloride, mesyl chloride or the like) or an acid derivative (e.g., ethyl chloroformate, isobutyl chloroformate or the like) at from 0 to 40° C. in the presence of a base (e.g., pyridine, triethylamine, dimethylaniline, dimethylaminopyridine, diisopropylethylamine or the like), and then allowing the thus obtained mixed acid halide to react with an amine at from 0 to 40° C. in an organic solvent (e.g., halogenated hydrocarbons such as chloroform and dichloromethane; ethers such as diethyl ether, tetrahydrofuran and dioxane; acid amides such as dimethylformamide; the like are used, wherein these solvents may be used alone or by mixing two or more of them, if necessary, at a ratio of, for example, from 1:1 to 1:10).

(3) The method which uses a condensing agent is carried out, for example, in an organic solvent (e.g., halogenated hydrocarbons such as chloroform and dichloromethane; ethers such as diethyl ether, tetrahydrofuran and dioxane; acid amides such as dimethylformamide; and the like are used, wherein these solvents may be used alone or by mixing two or more of them, if necessary, at a ratio of, for example, from 1:1 to 1:10), or without solvent, by allowing a carboxylic acid to react with an amine at from 0 to 40° C. in the presence or absence of a base (e.g., alkylamines such as triethylamine, tributylamine and diisopropylethylamine; aromatic amines such as N,N-dimethylaniline and pyridine, 4-(dimethylamino)pyridine; and the like), using a condensing agent (e.g., 1,3-dicyclohexylcarbodiimide (DCC), 1-ethyl-3-[3-(dimethylamino)propyl]carbodiimide (EDC), 1,1'-carbonyldiimidazole (CDI), 2-chloro-1-methylpyridinium iodine, 1-propyl phosphonate cyclic anhydride (1-propanephosphonic acid cyclic anhydride, PPA) or the like) and using or without using 1-hydroxybenzotriazole (HOBt).

It is desirable to carry out each of these reactions of (1), (2) and (3) in an inert gas (argon, nitrogen or the like) atmosphere under anhydrous condition.

3) The sulfone amidation reaction is conventionally known and can be carried out, for example, in an organic solvent (e.g., halogenated hydrocarbons such as chloroform and dichloromethane; ethers such as diethyl ether, tetrahydrofuran and dioxane; and the like are used, wherein these solvents may be used alone or by mixing two or more of them, if necessary, at a ratio of, for example, from 1:1 to 1:10), or without solvent, by allowing a sulfonic acid to react with an acid halide (e.g., oxalyl chloride, thionyl chloride, phosphorus pentachloride, phosphorus trichloride or the like) at from −20° C. to reflux temperature, and then allowing the thus obtained sulfonyl halide to react with an amine at from 0 to 40° C. in an organic solvent (e.g., halogenated hydrocarbons such as chloroform and dichloromethane; ethers such as diethyl ether, tetrahydrofuran and dioxane; and the like are used, wherein these solvents may be used alone or by mixing two or more of them, if necessary, at a ratio of, for example, from 1:1 to 1:10) in the presence of a base (e.g., alkylamines such as triethylamine, tributylamine and diisopropylethylamine; aromatic amines such as N,N-dimethylaniline, pyridine and 4-(dimethylamino)pyridine; and the like).

(B) Among the compounds of the present invention represented by formula (I-1), a compound in which $R^{1-1}$ represents an amino protecting group and ring A is represented by

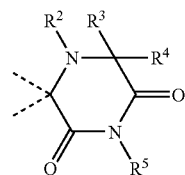

(wherein all symbols have the same meanings as those defined above), namely a compound represented by formula (I-1-A1):

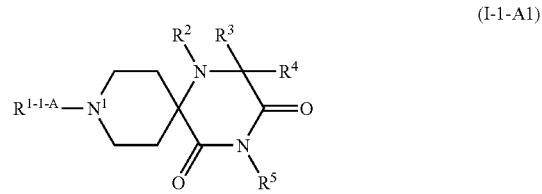

(I-1-A1)

(wherein $R^{1-1-A}$ represents an amino protecting group and other symbols have the same meanings as those defined above), can be produced by the method of the following reaction scheme (II).

As the protecting group of amino, for example, benzyl, benzyloxycarbonyl, allyloxycarbonyl, t-butoxycarbonyl, trifluoroacetyl and the like can be cited.

As the protecting group of amino, other groups than the above have no particular limitation with the proviso that they can be easily and selectively removed. For example, those which are described in T. W. Greene et al., *Protective Groups in Organic Synthesis*, Third Edition, Wiley-Interscience, New York, 1999, can be used.

Reaction Scheme (II)

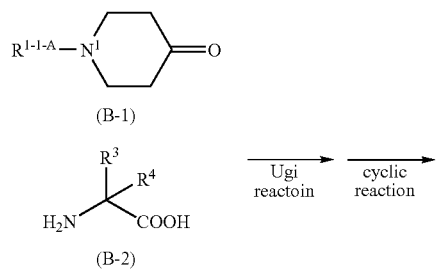

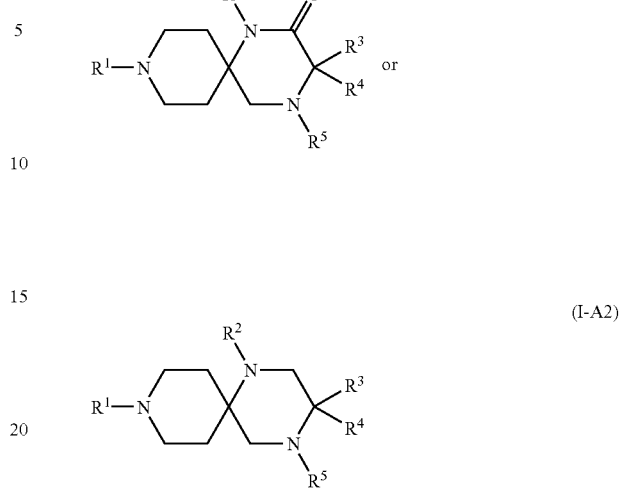

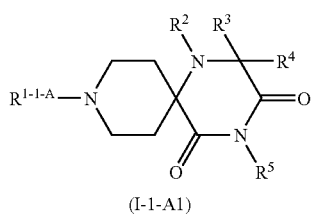

In the reaction scheme (II), all symbols have the same meanings as those defined above.

The Ugi reaction is conventionally known and carried out, for example, in an organic solvent (e.g., methanol or the like) at a temperature of from 0 to 80° C.

In addition, the cyclization reaction is conventionally known and carried out, for example, in an organic solvent (e.g., dichloroethane, toluene, ethyl acetate, a mixture thereof or the like) using or not using a tertiary amine (e.g., triethylamine, diisopropylethylamine or the like) or an acid (e.g., acetic acid, trifluoroacetic acid or the like), by heating at from 60 to 120° C.

(C) Among the compounds represented by formula (I), a compound in which ring A is represented by

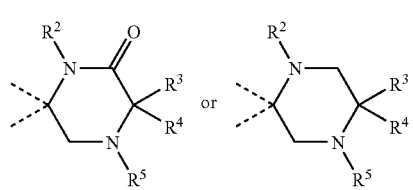

(wherein all symbols have the same meanings as those defined above), namely a compound represented by formula (I-A1) or (I-A2):

(wherein all symbols have the same meanings as those defined above), can be produced by carrying out a reduction reaction using a compound produced by the method described in WO 02/74770.

This reduction reaction is conventionally known and can be carried out, for example, in an organic solvent (e.g., dioxane, 1,2-dimethoxyethane, toluene, tetrahydrofuran, a mixture thereof or the like) in the presence or absence of an acid (e.g., acetic acid, trifluoroacetic acid, boron trifluoride ethyl ether complex or the like) using a reducing agent (e.g., sodium borohydride, lithium aluminum hydride, borane, borane-tetrahydrofuran complex or the like), at a temperature of from −78 to 40° C.

(D) Among the compounds of the present invention represented by formula (I-1), a compound in which $R^{1-1}$ represents an amino protecting group and ring A is represented by

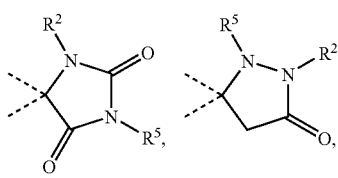

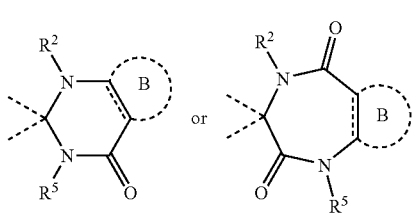

(wherein all symbols have the same meanings as those defined above), namely compounds represented by formulae (I-1-A2) to (I-1-A5):

(I-1-A2)
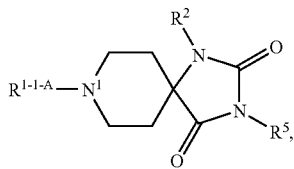

(I-1-A3)
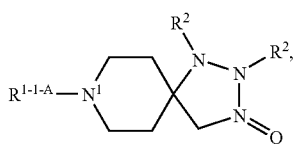

(I-1-A4)
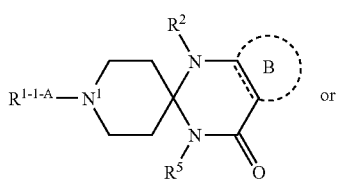
or (I-1-A5)
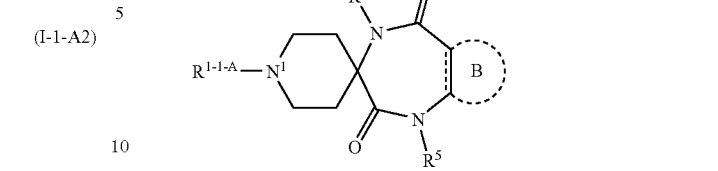

(wherein all symbols have the same meanings as those defined above), can be produced by subjecting a compound represented by formula (B-1):

(B-1)
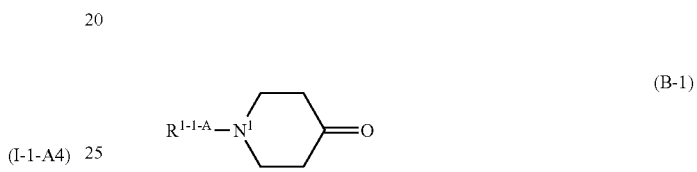

(wherein all symbols have the same meanings as those defined above) to the ring A forming reaction exemplified in the following reaction scheme (III) and/or subjecting it to a method in which a conventionally known method is optionally improved.

Reaction Scheme (III)

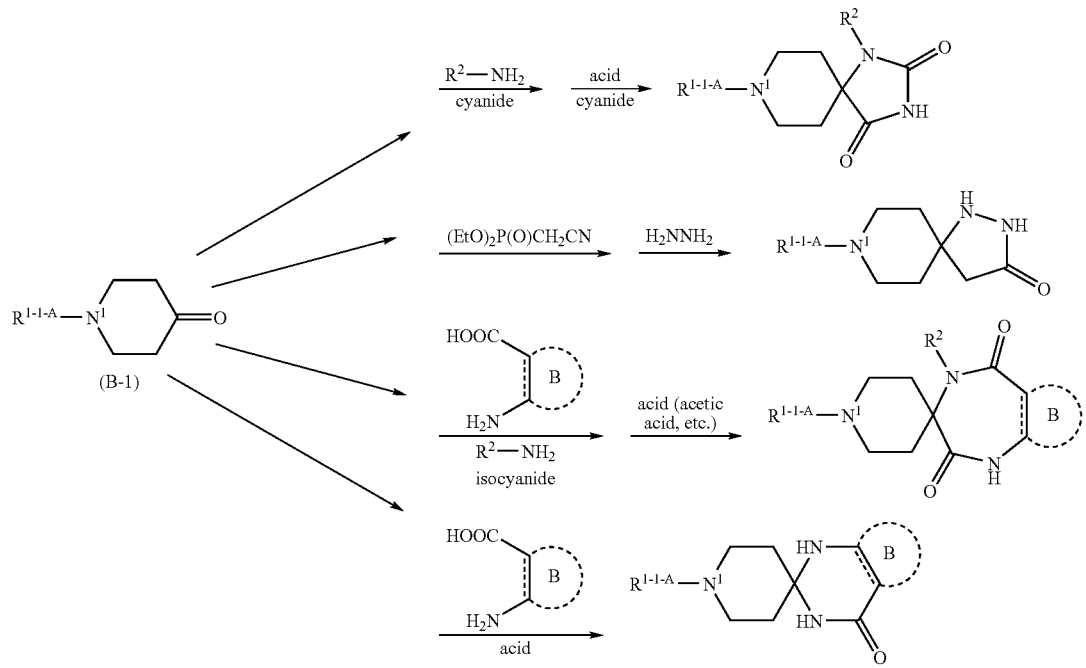

In the reaction scheme (III), all symbols have the same meanings as those defined above.

(E) Among the compounds of the present invention represented by formula (I-1), a compound in which $R^{1-1}$ represents an amino protecting group and ring A is represented by

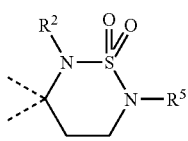

(wherein all symbols have the same meanings as those defined above), namely a compound represented by formula (I-1-A6):

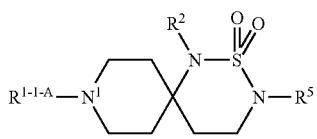
(I-1-A6)

(wherein all symbols have the same meanings as those defined above), can be produced by subjecting a compound represented by formula (E-1):

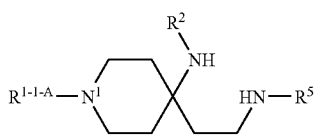
(E-1)

(wherein all symbols have the same meanings as those defined above) to a cyclization reaction.

This cyclization reaction is conventionally known and can be produced, for example, by carrying out the reaction at from −20° C. to reflux temperature in an organic solvent (e.g., ethyl acetate, chloroform, dichloroethane, diethyl ether, tetrahydrofuran, benzene, toluene or the like) or without solvent, in the presence or absence of a base (e.g., pyridine, triethylamine, dimethylaniline, dimethylaminopyridine, diisopropylethylamine or the like) and, for example, using sulfuryl chloride, sulfuryl fluoride or the like.

(F) Among the compounds of the present invention represented by formula (I-1), a compound in which $R^{1-1}$ represents an amino protecting group and ring A is represented by

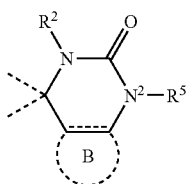

(wherein $N^2$ represents nitrogen, and other symbols have the same meanings as those defined above), namely a compound represented by formula (I-1-A7):

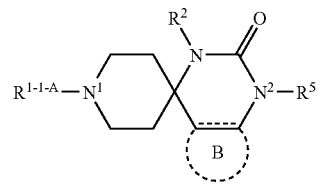
(I-1-A7)

(wherein all symbols have the same meanings as those defined above), can be produced by subjecting a compound represented by formula (F-1):

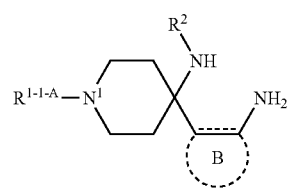
(F-1)

(wherein all symbols have the same meanings as those defined above) to a cyclization reaction, and further subjecting to a reaction with a compound represented by formula (F-2)

(F-2)

(wherein $X^1$ represents a leaving group (e.g., chlorine, bromine, iodine, p-toluenesulfonyloxy, methanesulfonyloxy, trifluoromethanesulfonyloxy or the like), and other symbols have the same meanings as those defined above), or subjecting a compound represented by formula (F-3):

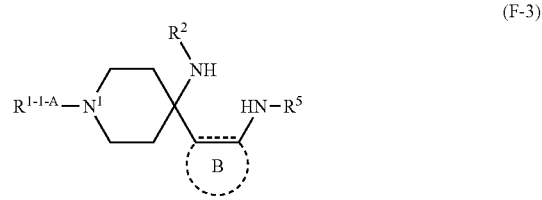
(F-3)

(wherein all symbols have the same meanings as those defined above) to a cyclization reaction.

This cyclization reaction is conventionally known and can be produced, for example, using a phosgene compound (phosgene, triphosgene(bis(trichloromethyl)carbonate or the like) or an imidazole compound (e.g., CDI (carbonyldiimidazole) or the like) and allowing to react at from −20° C. to reflux temperature, for example, in an organic solvent (e.g., ethyl acetate, chloroform, dichloroethane, diethyl ether, tetrahydrofuran, benzene, toluene or the like) or without solvent, and in the presence of a base (e.g., pyridine, triethylamine, dimethylaniline, dimethylaminopyridine, diisopropylethylamine or the like).

The reaction with this compound represented by formula (F-2) is conventionally known and can be carried out, for example, in the same manner as the alkylation reaction, amidation reaction or sulfone amidation reaction according to the above-described (A).

(G) Among the compounds of the present invention represented by formula (I-1), a compound in which $R^{1-1}$ represents an amino protecting group and ring A is represented by

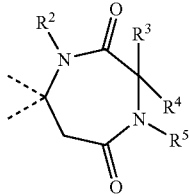

(wherein all symbols have the same meanings as those defined above), namely a compound represented by formula (I-1-A8):

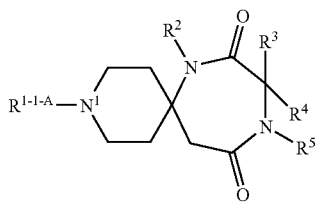
(I-1-A8)

(wherein all symbols have the same meanings as those defined above), can be produced by subjecting a compound represented by formula (G-1):

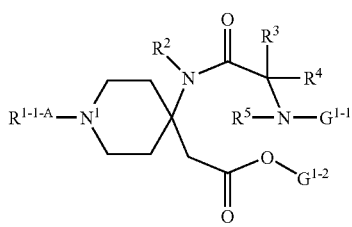
(G-1)

(wherein $G^{1-1}$ represents an amino protecting group (which has the same meaning as the amino protecting group according to the above-described (B)), $G^{1-2}$ represents alkyl, and other symbols have the same meanings as those defined above) to a deprotection reaction of amino group and further subjecting to a cyclization reaction.

This deprotection reaction of amino group is conventionally known and, for example,
(1) deprotection reaction by alkali hydrolysis,
(2) deprotection reaction under acidic condition,
(3) deprotection reaction by hydrolysis,
(4) deprotection reaction which uses a metal complex, and the like can be cited.

These methods are described below in detail.
(1) The deprotection reaction by alkali hydrolysis (e.g., trifluoroacetyl or the like) is carried out, for example, at a temperature of from 0 to 40° C. in an organic solvent (e.g., methanol, tetrahydrofuran, dioxane or the like), using hydroxide of an alkali metal (e.g., sodium hydroxide, potassium hydroxide, lithium hydroxide or the like), hydroxide of an alkaline earth metal (e.g., barium hydroxide, calcium hydroxide or the like) or a carbonate (e.g., sodium carbonate, potassium carbonate or the like), or an aqueous solution thereof or a mixture thereof.
(2) The deprotection reaction under acidic condition (e.g., t-butoxycarbonyl or the like) is carried out, for example, at a temperature of from 0 to 100° C. in an organic solvent (e.g., dichloromethane, chloroform, dioxane, ethyl acetate, anisole or the like), and in an organic acid (e.g., acetic acid, trifluoroacetic acid, methanesulfonic acid or the like), or an inorganic acid (e.g., hydrochloric acid, sulfuric acid or the like) or a mixture thereof (e.g., hydrogen bromide/acetic acid or the like).
(3) The deprotection reaction by hydrolysis (e.g., benzyl, benzyloxycarbonyl, allyloxycarbonyl or the like) is carried out, for example, at a temperature of from 0 to 200° C. in a solvent (e.g., an ether system (e.g., tetrahydrofuran, dioxane, dimethoxyethane, diethyl ether or the like), an alcohol system (e.g., methanol, ethanol or the like), a benzene system (e.g., benzene, toluene or the like), a ketone system (e.g., acetone, methyl ethyl ketone or the like), a nitrile system (e.g., acetonitrile or the like), an amide system (e.g., dimethylformamide or the like), water, ethyl acetate, acetic acid, a mixed solvent of 2 or more thereof or the like), in the presence of a catalyst (e.g., palladium-carbon, palladium black, palladium hydroxide, platinum oxide, Raney nickel or the like), and in an atmosphere of hydrogen under ordinary pressure or pressurization or in the presence of ammonium formate.
(4). The deprotection reaction which uses a metal complex is carried out, for example, at a temperature of from 0 to 40° C. in an organic solvent (e.g., dichloromethane, dimethylformamide, tetrahydrofuran or the like), in the presence of a trapping agent (e.g., tributyltin hydride, dimedone or the like) and/or an organic acid (acetic acid or the like), and using a metal complex (e.g., tetrakistriphenylphosphine palladium(O) complex or the like).

Although it can be easily understood by those skilled in the art, the intended compound of the present invention can be easily produced by properly using amino protecting groups of $R^{1-1}$ and $R^{1-1-A}$.

In addition, this cyclization reaction is conventionally known and can be carried out, for example, by carrying out an amidation reaction after hydrolysis, or can also be carried out by simply heating it.

This hydrolysis is conventionally known and can be carried out, for example, at a temperature of from 0 to 40° C. in an organic solvent (e.g., methanol, tetrahydrofuran, dioxane or the like), using hydroxide of an alkali metal (e.g., sodium hydroxide, potassium hydroxide, lithium hydroxide or the like), hydroxide of an alkaline earth metal (e.g., barium hydroxide, calcium hydroxide or the like) or a carbonate (e.g., sodium carbonate, potassium carbonate or the like), or an aqueous solution thereof or a mixture thereof.

Also, this amidation reaction is conventionally known and can be carried out, for example, in the same manner as the amidation reaction according to the above-described (A).

In addition, the cyclization reaction by heating is conventionally known and can be carried out, for example, by allowing to react at from room temperature to reflux temperature (from room temperature to 150° C. in the case of no solvent), in an organic solvent (e.g., methanol, ethanol, tetrahydrofuran, dioxane, benzene, toluene, xylene, acetonitrile, dimethylformamide, 1,2-dimethoxyethane, dimethylacetamide or the like) or without solvent, and in the presence or absence of a base (e.g., an inorganic base (e.g., sodium bicarbonate, sodium acetate or the like), an organic base (e.g., pyridine, triethylamine, dimethylaniline, dimethylaminopyridine, diisopropylethylamine, N-methylmorpholine or the like), an alkoxide (e.g., sodium methoxide, sodium ethoxide or the like) or the like).

(H) Among the compounds of the present invention represented by formula (I-1), a compound in which $R^{1-1}$ represents an amino protecting group and ring A is represented by

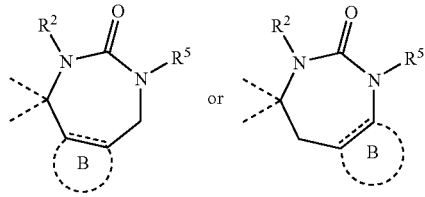

(wherein all symbols have the same meanings as those defined above), namely a compound represented by formula (I-1-A9) or (I-1-A10):

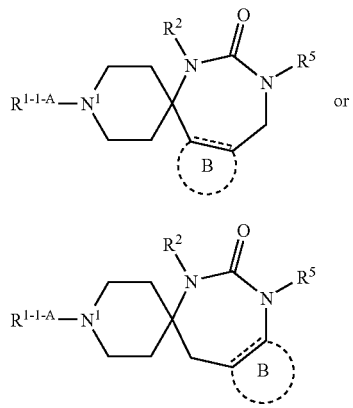
(I-1-A9)

(I-1-A10)

(wherein all symbols have the same meanings as those defined above), can be produced by subjecting a compound represented by formula (H-1) or (H-2):

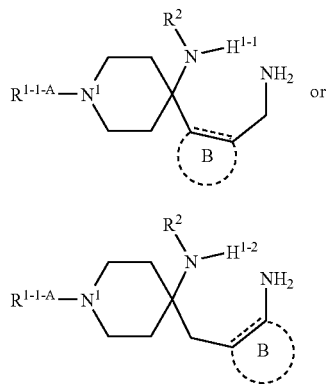
(H-1)

(H-2)

(wherein $H^{1-1}$ and $H^{1-2}$ represent amino protecting groups (represent the same amino protecting groups according to the above-described (B)), and other symbols have the same meanings as those defined above) to the same amino group deprotection reaction of the method according to the above-described (B) and further subjecting it to the same cyclization reaction of the method according to the above-described (F).

Also, among the compounds of the present invention represented by formulae (I-1-A9) and (I-1-A10), a compound in which ring A is represented by

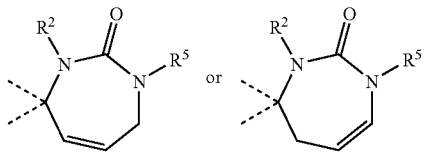

(wherein all symbols have the same meanings as those defined above), namely a compound represented by formula (I-1-A9-1) or (I-1-A10-1):

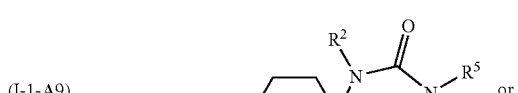
(I-1-A9-1)

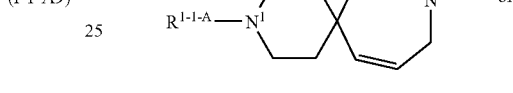

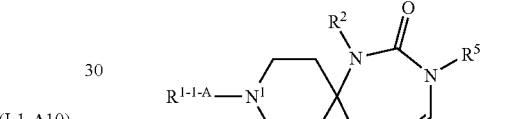
(I-1-A10-1)

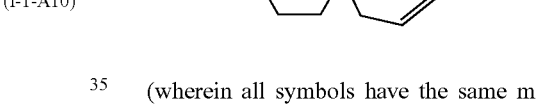

(wherein all symbols have the same meanings as those defined above), can also be produced by subjecting a compound represented by formula (H-3) or formula (H-4):

(H-3)

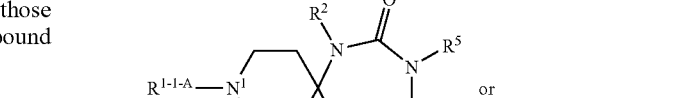

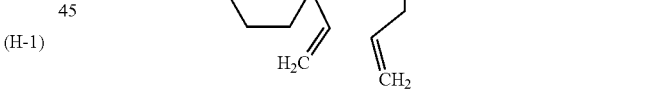
(H-4)

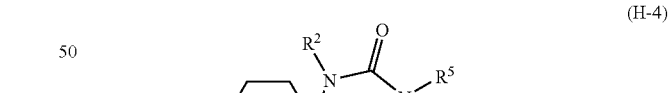

(wherein all symbols have the same meanings as those defined above) to the same cyclization reaction (metathesis).

This cyclization reaction is conventionally known and can be carried out, for example, by allowing to react at from room temperature to 100° C. in an organic solvent (e.g., dichloromethane, toluene, a mixture thereof or the like) in the presence of a Grubbs' catalyst (e.g., benzylidene[1,3-bis(mesitylene)-2-imidazolidinylidene]tricyclohexylphosphine ruthenium(IV) dichloride or the like).

(J) Among the compounds of the present invention represented by formula (I-1), a compound in which $R^{1-1}$ represents an amino protecting group and ring A is represented by

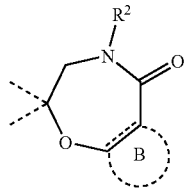

(wherein all symbols have the same meanings as those defined above), namely a compound represented by formula (I-1-A11):

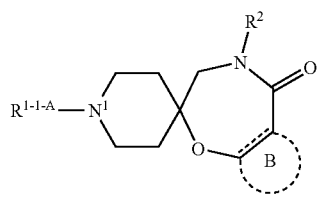

(I-1-A11)

(wherein all symbols have the same meanings as those defined above), can be produced by subjecting a compound represented by formula (J-1):

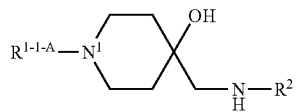

(J-1)

(wherein all symbols have the same meanings as those defined above) and a compound represented by formula (J-2):

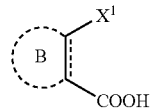

(J-2)

(wherein $X^1$ represents a halogen (e.g., chlorine, bromine, iodine or the like), and other symbols have the same meanings as those defined above) to the same amidation reaction of the method according to the above-described (A) and further subjecting it to a cyclization reaction.

This cyclization reaction is conventionally known and can be carried out, for example, by allowing to react at from −78 to 200° C. in an organic solvent (e.g., tetrahydrofuran, diethyl ether, N,N-dimethylformamide, a mixture thereof or the like) in the presence of a base (e.g., lithium diisopropylamine (carried out in the presence of an amine (e.g., N,N,N',N",N"-pentamethyldiethylenetriamine, N,N,N',N'-tetramethylethylenediamine or the like), if necessary,), sodium hydride, potassium carbonate, cesium carbonate or the like).

(K) Among the compounds of the present invention represented by formula (I-1), a compound in which $R^{1-1}$ is an amino protecting group and ring A is represented by

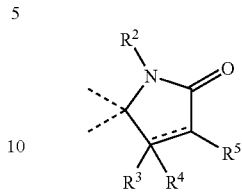

(wherein all symbols have the same meanings as those defined above), namely a compound represented by formula (I-1-A12) or (I-1-A13):

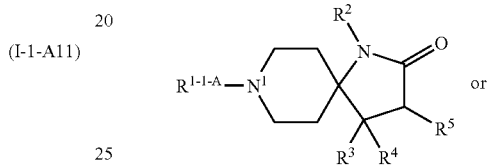

(I-1-A12)

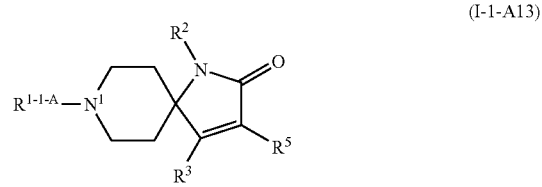

(I-1-A13)

(wherein all symbols have the same meanings as those defined above), can be produced by subjecting a compound represented by formula (K-1):

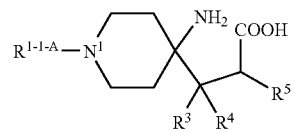

(K-1)

(wherein all symbols have the same meanings as those defined above) to a cyclization reaction and further subjecting to its reaction with a compound represented by formula (K-2)

$R^2$—$X^1$ (K-2)

or by subjecting a compound represented by formula (K-3):

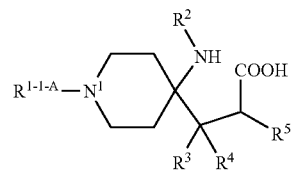

(K-3)

(wherein all symbols have the same meanings as those defined above) to a cyclization reaction, or by subjecting a compound represented by formula (K-4):

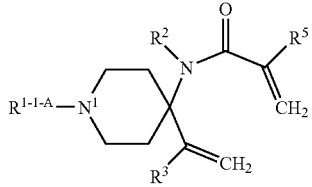

(K-4)

(wherein all symbols have the same meanings as those defined above) to a cyclization reaction (metathesis).

The cyclization reaction of the compounds represented by formulae (K-1) and (K-3) is conventionally known and can be carried out, for example, by the same amidation reaction of the method according to the above-described (A).

Also, this reaction with the compound represented by formula (K-2) is conventionally known and can be carried out, for example, in the same manner as the alkylation reaction, amidation reaction and sulfone amidation reaction according to the above-described (A).

The cyclization reaction of the compound represented by formula (K-4) is conventionally known and can be carried out, for example, by subjecting it to the same cyclization reaction of the method according to the above-described (H).

The compounds of the present invention represented by formula (I-2) can also be produced by subjecting the compounds obtained by the above-described reactions of (B), (D), (E), (F), (G), (H), (J) and (K) to the above-described deprotection reaction of amino protecting group.

The compounds represented by formula (B-1) to be used as the starting materials in the reaction schemes (II) and (III) are conventionally known, or can be easily produced by conventionally known methods. In addition, the compounds represented by formulae (E-1), (F-1), (F-3), (G-1), (H-1), (H-2), (H-3), (H-4), (J-1), (J-2), (K-1), (K-3) and (K-4) to be used as the starting materials in the above-described (E) to (H), (J) and (K) are conventionally known, or can be easily produced by using the compound represented by formula (B-1) as the material and combining conventionally known methods.

In the respective reactions in this specification, the reaction products can be purified by general purification means, such as distillation under ordinary pressure or a reduced pressure, high performance liquid chromatography, thin layer chromatography or column chromatography which uses silica gel or magnesium silicate, washing, recrystallization and the like methods. The purification may be carried out for each reaction or carried out after completion of some reactions.

In the reactions in the specification, a reaction which requires heating can be carried out using a water bath, an oil bath, a sand bath or a microwave as is evident to those skilled in the art.

Pharmacological Activities of the Compounds of the Present Invention:

As pharmacological tests other than those described in Examples, for example, there are methods shown above. The chemokine receptor antagonism of the compounds of the present invention can be proved by the methods shown above.

For the purpose of carrying out screening of a compound which inhibits binding of HIV to CXCR4 or CCR5 as the receptor on the CD4-positive cell, a more direct technique is to carry it out by an assay system that uses HIV virus. However, use of HIV virus in a large scale screening is not practical in view of the difficulty in its handling. On the other hand, since macrophage-directional (R5) HIV-1 and RANTES, MIP-1α and MIP-1β together bind to CCR5, it can be considered that there are certain common characteristics between the CCR5 binding sites of the HIV side and the RANTES, MIP-1α and MIP-1β side and the CCR5 side RANTES, MIP-1α, MIP-1β and HIV binding sites. Accordingly, in order to discover a compound capable of inhibiting adsorption of HIV virus to cells which is an action mechanism different from the already existing anti-AIDS drugs (reverse transcription inhibitor and protease inhibition), an assay system that uses RANTES, MIP-1α and MIP-1β as endogenous ligands of CCR5, instead of HIV, is applicable.

Specifically, as a system for screening a compound capable of inhibiting binding of RANTES and CCR5, for example, since CCR5 is a G protein-coupling 7 times transmembrane type receptor, it is possible to carry out a system which measures the effect of transient increase of calcium (Ca) ion induced by RANTES via CCR5. Since T cell-directional (X4) HIV and SDF-1 together bind to CXCR4, similar viewpoint is possible.

Toxicity:

The toxicity of the compounds of the present invention is very low and therefore the compounds may be considered safe for pharmaceutical use.

Application to Pharmaceuticals:

The compounds of the present invention represented by formula (I) regulate the effect of CCR5 receptor in animal included human, especially human, so they are used for prevention and/or treatment of various inflammatory diseases, immune diseases such as autoimmune diseases or allergic diseases, or HIV infection. For example, they are useful for prevention and/or treatment of asthma, nephritis, nephropathy, hepatitis, arthritis, rheumatoid arthritis, rhinitis, conjunctivitis, ulcerative colitis, and the like, rejection in organ transplantation, immunosuppression, psoriasis, multiple sclerosis, infection with human immunodeficiency virus (acquired immunodeficiency syndrome and the like), atopic dermatitis, uticaria, allergic bronchopulmonary aspergillosis, allergic eosinophilic gastroenteritis, ischemic reperfusion injury, acute respiratory distress syndrome, shock accompanying bacterial infection, diabetes mellitus, cancer metastasis, arteriosclerosis and the like.

The compounds of the present invention by formula (I), salts thereof, N-oxides thereof, quaternary ammonium salts thereof or solvates salts, or prodrugs thereof may be normally administered systemically or locally, usually by oral or parenteral administration.

Since the compounds of the present invention by formula (I), salts thereof, N-oxides thereof, quaternary ammonium salts thereof or solvates salts, or prodrugs thereof are safe and low-toxic, they may be administered to a human or a mammal (e.g., rat, mouse, rabbit, sheep, pig, cow, cat, dog, monkey, etc.).

The doses to be administered are determined depending upon, for example, age, body weight, symptom, the desired therapeutic effect, the route of administration, and the duration of the treatment. In the human adult, the doses per person are generally from 1 mg to 1000 mg, by oral administration, up to several times per day, and from 1 mg to 100 mg, by parenteral administration (preferably intravenous administration), up to several times per day, or continuous administration from 1 to 24 hours per day from vein.

As mentioned above, the doses to be used depend upon various conditions. Therefore, there are cases in which doses lower than or greater than the ranges specified above may be used.

The compounds of the present invention, salts thereof, N-oxides thereof, quaternary ammonium salts thereof or solvates salts, or prodrugs thereof may be administered for example, in the form of solid for oral administration, liquid forms for oral administration, injections, liniments or suppositories for parenteral administration.

Solid forms for oral administration include compressed tablets, pills, capsules, dispersible powders, and granules. Capsules include hard capsules and soft capsules.

In such solid forms, one or more of the active compound(s) may be admixed with vehicles (such as lactose, mannitol, glucose, microcrystalline cellulose or starch), binders (such as hydroxypropyl cellulose, polyvinylpyrrolidone or magnesium metasilicate aluminate), disintegrants (such as cellulose calcium glycolate), lubricants (such as magnesium stearate), stabilizing agents, and solution adjuvants (such as glutamic acid or aspartic acid) and prepared according to methods well known in normal pharmaceutical practice. The solid forms may, if desired, be coated with coating agents (such as sugar, gelatin, hydroxypropyl cellulose or hydroxypropylmethyl cellulose phthalate), or be coated with two or more films. And further, coating may include containment within capsules of absorbable materials such as gelatin.

Liquid forms for oral administration include pharmaceutically acceptable solutions, suspensions, emulsions, syrups and elixirs. In such forms, one or more of the active compound(s) may be dissolved, suspended or emulsified into diluent(s) commonly used in the art (such as purified water, ethanol or a mixture thereof). Besides such liquid forms may also comprise some additives, such as wetting agents, suspending agents, emulsifying agents, sweetening agents, flavoring agents, aroma, preservative or buffering agent.

Injections for parenteral administration include all injections and also include drips. Examples include intramuscular injections, subcutaneous injections, intradermal injections, arterial injections, intravenous rejections, intraperitoneal injections, spinal injections, and intravenous drips.

Injections for parenteral administration include sterile aqueous, suspensions, emulsions and solid forms which are dissolved or suspended into solvent(s) for injection immediately before use. In injections, one or more of the active compound(s) may be dissolved, suspended or emulsified into solvent(s). The solvents may include distilled water for injection, saline, vegetable oil, propylene glycol, polyethylene glycol, alcohol such as ethanol, or a mixture thereof Injections may comprise some additives, such as stabilizing agents, solution adjuvants (such as glutamic acid, aspartic acid or POLYSORBATE80 (registered trade mark)), suspending agents, emulsifying agents, soothing agent, buffering agents, preservative. They may be sterilized at a final step, or may be prepared according to sterile methods. They may also be manufactured in the form of sterile solid forms such as freeze-dried products, which may be dissolved in sterile water or some other sterile diluent(s) for injection immediately before use.

Other forms for parenteral administration include liquids for external use, ointments and endermic liniments, inhalations, sprays, suppositories and pessaries for vaginal administration which comprise one or more of the active compound(s) and may be prepared by methods known per se.

Sprays may comprise additional substances other than diluents, such as stabilizing agents, such as sodium sulfate, isotonic buffers, such as sodium chloride, sodium citrate or citric acid. For preparation of such sprays, for example, the method described in the U.S. Pat. Nos. 2,868,691 or 3,095,355 may be used.

The compounds of the present invention represented by formula (I), salts thereof, N-oxides thereof, quaternary ammonium salts thereof or solvates salts, or prodrugs thereof may be used together with other drugs, for example, preventive and/or treating agent(s) for HIV infection (particularly agents for prevention and/or treatment for AIDS). In that case, the drug as such may be mixed with pharmacologically acceptable excipient, binder, disintegrating agent, lubricant, stabilizer, solubilizer, diluent, etc. either separately or simultaneously to make into a pharmaceutical preparation and that can be administered either orally or parenterally as a pharmaceutical composition for prevention and/or treatment of HIV infection.

The compounds of the present invention represented by formula (I), salts thereof, N-oxides thereof, quaternary ammonium salts thereof or solvates salts, or prodrugs thereof have an infection inhibiting activity to HIV-I which acquired resistance to other agents for preventive and/or treating HIV infection (particularly agents for prevention and/or treatment for AIDS). Therefore, it is also able to be used for HIV-infected patients to whom other agents for preventive and/or treating HIV infection are no longer effective. In that case, although the compound of the present invention may be used solely, it may be also used together with agents for preventive and/or treating HIV infection where infected HIV-1 strain acquired resistance or with other drugs.

A combination drug obtained by combining the compounds of the present invention represented by formula (I), salts thereof, N-oxides thereof, quaternary ammonium salts thereof or solvates salts, or prodrugs thereof with other medicaments may be administered to accomplish the following purposes:

1) to supplement and/or enhance the preventive and/or therapeutic effect of the compounds of the present invention;
2) to improve the kinetics and/or absorption and reduce the dose of the compounds of the present invention; and/or
3) to eliminate the side effects of the compounds of the present invention.

Also, (1) to supplement and/or enhance the preventive and/or therapeutic effect, (2) to improve the kinetics and/or absorption and reduce the dose, and/or (3) to eliminate the side effects of the other medicaments used in combination, the compounds of the present invention may be combined and administered as a combination drug.

A combination of the compounds of the present invention represented by formula (I), salts thereof, N-oxides thereof, quaternary ammonium salts thereof or solvates salts, or prodrugs thereof with other medicaments may be administered in the form of the formulations having these components incorporated in one preparation, or may be administered in separate preparations. In the case where these medicaments are administered in separate preparations, they may be administered simultaneously or at different times. In the latter case, the compounds of the present invention represented by formula (I), salts thereof, N-oxides thereof, quaternary ammonium salts thereof or solvates salts, or prodrugs thereof may be administered before the other medicaments. Alternatively, the other medicaments may be administered before the compounds of the present invention represented by formula (I), salts thereof, N-oxides thereof, quaternary ammonium salts thereof or solvates salts, or prodrugs thereof The method for the administration of these medicaments are the same or different.

The present invention covers the case where the compounds represented by formula (I), salts thereof, N-oxides thereof, quaternary ammonium salts thereof or solvates salts, or prodrugs thereof is combined with drugs which do not inhibit the HIV infection whereby preventive and/or treating effect for HIV infection is enhanced as compared with a single preparation.

Examples of other agent for preventive and/or treating HIV infection used for a combination with the compounds of the present invention represented by formula (I), salts thereof, N-oxides thereof, quaternary ammonium salts thereof or solvates salts, or prodrugs thereof are reverse transcriptase inhibitor, protease inhibitor, chemokine antagonist (such as CCR2 antagonist, CCR3 antagonist, integrase inhibitors, CCR4 antagonist, CCR5 antagonist and CXCR4 antagonist), fusion inhibitor, antibody to surface antigen of HIV-1 and vaccine of HIV-1.

Integrase inhibitors are concretely S-1360, 1838, V-165, L-708906 analogue, NSC-618929, equisetin, temacrazine, PL-2500, L-870810 etc.

Reverse transcriptase inhibitors are concretely (1) nucleoside/nucleotide reverse transcriptase inhibitors: zidovudine (brand name: Retrovir), didanosine (brand name: Videx), zalcitabine (brand name: HIVID), stavudine (brand name: Zerit), lamivudine (brand name: Epivir), abacavir (brand name: Ziagen), adefovir, adefovir dipivoxil, emtricitabine (brand name: Coviracil) or PMPA (brand name: Tenofovir) etc. and (2) nonnucleoside reverse transcriptase inhibitors: nevirapine (brand name: Viramune), delavirdine (brand name: Rescriptor), efavirenz (brand name: Sustiva, Stocklin) or capravirine (AG1549) etc.

Protease inhibitors are concretely indinavir (brand name: Crixivan), ritonavir (brand name: Norvir), nelfinavir (brand name: Viracept), saquinavir (brand name: Invirase, Fortovase), amprenavir (brand name: Agenerase), lopinavir (brand name: Kaletra) or tipranavir etc.

As chemokine antagonists, internal ligand of chemokine receptor, its derivatives, its non-peptide low molecular compound or antibody of chemokine receptor are included.

The examples of internal ligand of chemokine receptor are concretely, MIP-1α, MIP-1β, RANTES, SDF-1α, SDF-1β, MCP-1, MCP-2, MCP-4, Eotaxin and MDC etc.

The derivatives of internal ligand are concretely, AOP-RANTES, Met-SDF-1α, Met-SDF-1β etc.

Antibodies of chemokine receptor are concretely, Pro-140 etc.

CCR2 antagonists are concretely written in specification of WO99/07351, WO99/40913, WO00/46195, WO00/46196, WO00/46197, WO00/46198, WO00/46199, WO00/69432 or WO00/69815 or in *Bioorg. Med. Chem. Lett.*, 10, 1803 (2000) etc.

CCR3 antagonists are concretely written in specification of DE19837386, WO99/55324, WO99/55330, WO00/04003, WO00/27800, WO00/27835, WO00/27843, WO00/29377, WO00/31032, WO00/31033, WO00/34278, WO00/35449, WO00/35451, WO00/35452, WO00/35453, WO00/35454, WO00/35876, WO00/35877, WO00/41685, WO00/51607, WO00/51608, WO00/51609, WO00/51610, WO00/53172, WO00/53600, WO00/58305, WO00/59497, WO00/59498, WO00/59502, WO00/59503, WO00/62814, WO00/73327 or WO01/09088 etc.

CCR5 antagonists are concretely written in specification of WO99/17773, WO99/32100, WO00/06085, WO00/06146, WO00/10965, WO00/06153, WO00/21916, WO00/37455, EP1013276, WO00/38680, WO00/39125, WO00/40239, WO00/42045, WO00/53175, WO00/42852, WO00/66551, WO00/66558, WO00/66559, WO00/66141, WO00/68203, JP2000309598, WO00/51607, WO00/51608, WO00/51609, WO00/51610, WO00/56729, WO00/59497, WO00/59498, WO00/59502, WO00/59503, WO00/76933, WO98/25605 or WO99/04794, WO99/38514 or in *Bioorg. Med. Chem. Lett.*, 10, 1803 (2000) etc.

CXCR4 antagonists are concretely AMD-3100, T-22, KRH-1120, or the compounds written in specification of WO00/66112 etc.

Fusion Inhibitors are concretely, T-20 (Pentafuside) and T-1249 etc.

The examples of combination drugs written above are intended to illustrate the present invention, but do not limit them.

The typical examples of the usual the dosage level in clinical trials of reverse transcriptase inhibitors or protease inhibitors written below are intended to illustrate the present invention, but do not limit them.

Zidovudine: 100 mg capsule, 200 mg per dose, 3 times per day;

300 mg tablet, 300 mg per dose, twice per day;

didanosine: 25-200 mg tablet, 125-200 mg per dose, twice per day;

zalcitabine: 0.375-0.75 mg tablet, 0.75 mg per dose, 3 times per day;

stavudine: 15-40 mg capsule, 30-40 mg per dose, twice per day;

lamivudine: 150 mg tablet, 150 mg per dose, twice per day;

abacavir: 300 mg tablet, 300 mg per dose, twice per day;

nevirapine: 200 mg tablet, 200 mg per dose, once per day for 14 days and then twice per day;

delavirdine: 100 mg tablet, 400 mg per dose, 3 times per day;

efavirenz: 50-200 mg capsule, 600 mg per dose, once per day;

indinavir: 200-400 mg capsule, 800 mg per dose, 3 times per day;

ritonavir: 100 mg capsule, 600 mg per dose, twice per day;

nelfinavir: 250 mg tablet, 750 mg per dose, 3 times per day;

saquinavir: 200 mg capsule, 1,200 mg per dose, 3 times per day;

amprenavir: 50-150 mg tablet, 1,200 mg per dose, twice per day.

EFFECT OF THE PRESENT INVENTION

The compounds of the present invention represented by formula (I), salts thereof, N-oxides thereof, quaternary ammonium salts thereof or solvates salts, or prodrugs thereof have CCR5 or CCR2 antagonistic action, and safe and low-toxic, so that they are useful for prevention and/or treatment of various inflammatory diseases, immune diseases such as autoimmune diseases or allergic diseases, or HIV infection. For example, they are useful for prevention and/or treatment of asthma, nephritis, nephropathy, hepatitis, arthritis, rheumatoid arthritis, rhinitis, conjunctivitis, ulcerative colitis, and the like, rejection in organ transplantation, immunosuppression, psoriasis, multiple sclerosis, infection with human immunodeficiency virus (acquired immunodeficiency syndrome and the like), atopic dermatitis, uticaria, allergic bronchopulmonary aspergillosis, allergic eosinophilic gastroenteritis, ischemic reperfusion injury, acute respiratory distress syndrome, shock accompanying bacterial infection, diabetes mellitus, cancer metastasis, arteriosclerosis and the like.

BEST MODE FOR CARRYING OUT THE INVENTION

The following reference examples and examples illustrate the present invention, but they do not limit the present invention.

The solvents in the parentheses show the developing solvents or eluting solvents and the ratios of the solvents used are by volume in chromatographic separations or TLC. The solvents in the parentheses in NMR show the solvents for measurement.

In addition, about result of NMR there is the case which a selected value to express structural character is shown.

HPLC condition is outlined below as far as there is not description in particular.
Column: Xterra® MS $C_{18}$, 4.6×50 mm I.D., 5 µm, 100 Å
Flow rate: 3 ml/min
Solvent:
  Liquid A: 0.1% trifluoroacetic acid aqueous solution
  Liquid B: 0.1% trifluoroacetic acid—acetonitrile solution
  Mix proportion of liquid A and B during 0.5 minutes from a beginning of measurement was held 95/5. Then the proportion was gradually changed to 0/100 for 2.5 minutes and held 0/100 for 0.5 minutes. Finally the proportion was gradually changed to 95/5 for 0.01 minutes.

REFERENCE EXAMPLE 1

N-benzyloxycarbonyl-4-piperidone

A 4-piperidone hydrochloride monohydrate (15.3 g) was dissolved in 2N aqueous solution of sodium hydroxide (100 mL). To the solution was added a benzyloxycarbonyl chloride (20.4 g) at 0° C. The mixture was stirred for 1 hour. The reaction mixture was neutralized with 2N hydrochloric acid, and the aqueous solution was extracted three times with ethyl acetate. The organic layer was washed with a saturated aqueous solution of sodium bicarbonate and a saturated aqueous solution of sodium chloride subsequently, dried over anhydrous magnesium sulfate and concentrated to give the title compound (23.3 g) having the following physical data.
  TLC: Rf 0.29 (n-hexane:ethyl acetate=2:1); NMR $(CDCl_3)$:δ 2.46(t, J=6.3 Hz, 4H), 5.18(s, 2H).

REFERENCE EXAMPLE 2

N-benzyloxycarbonyl-4-cyano-4-(1-butylamino) piperidine hydrochloride

A solution of the compound prepared in Reference Example 1 (5.0 g) and butylamine hydrochloride (2.34 g) in 50% aqueous methanol (10 mL) was stirred for 15 minutes at 0° C. To the solution was added a solution of potassium cyanide (1.40 g) in water (4 mL). The reaction mixture was stirred for 24 hours at room temperature. To the mixture was added diethyl ether (20 mL) and water (15 mL) and the mixture was separated. The aqueous layer was extracted three times with diethyl ether. The combined organic layer was dried over anhydrous magnesium sulfate and concentrated. To the residue was added 4N hydrogen chloride in ethyl acetate and then the solution was concentrated. The residue was washed with diethyl ether to give the title compound (6.07 g) having the following physical data.
  TLC: Rf 0.71 (n-hexane:ethyl acetate=1:1); NMR $(CD_3OD)$:δ 1.01 (t, J=7.4 Hz, 3H), 5.14(s, 2H).

REFERENCE EXAMPLE 3

1-butyl-8-benzyloxycarbonyl-1,3,8-triazaspiro[4.5]decane-2,4-dione

To a solution of the compound prepared in Reference Example 2 (2.0 g) in acetic acid (5 mL) was added a solution of potassium cyanate (922 mg) in water (2 mL) at room temperature. The solution was stirred for 1 hour at 50° C. The mixture was poured into an ice-water (10 mL). The aqueous layer was extracted three times with ethyl acetate. The combined organic layer was washed with a saturated aqueous solution of sodium chloride, dried over an anhydrous magnesium sulfate and then concentrated. To the residue was added 3N hydrochloric acid (5 mL) and the mixture was stirred for 20 minutes at 50° C. The reaction mixture was extracted three times with ethyl acetate. The combined organic layer was dried over an anhydrous magnesium sulfate and concentrated. The residue was purified by column chromatography on silica gel (chloroform:methanol=1:0→20:1) to give the title compound (1.6 g) having the following physical data.
  TLC: Rf 0.42 (chloroform:methanol=10:1); Mass: FAB (Pos.) m/z 360 (M+H)$^+$, 316, 254, 224, 91; NMR $(CDCl_3)$:δ 3.79(t, J=6.2 Hz, 2H), 5.15(s, 2H).

REFERENCE EXAMPLE 4

1-butyl-3-isobutyl-8-benzyloxycarbonyl-1,3,8-triazaspiro[4.5]decane-2,4-dione

To a solution of the compound prepared in Reference Example 3 (600 mg) in N,N-dimethylformamide (4 mL) were added potassium carbonate (531 mg) and 1-bromo-2-methylpropane (686 mg) and the mixture was stirred for 15 hours at room temperature. The reaction mixture was neutralized with 2N aqueous solution of citric acid. The aqueous layer was extracted with a mixed solvent of ethyl acetate:n-hexane=4:1. The combined organic layer was washed with water and a saturated aqueous solution of sodium chloride subsequently, dried over an anhydrous magnesium sulfate and then concentrated. The residue was purified by column chromatography on silica gel (n-hexane:ethyl acetate=10:1→1:1) to give the title compound (658 mg) having the following physical data.
  TLC: Rf 0.62 (n-hexane:ethyl acetate=1:1); Mass: APCI (Pos.) m/z 416 (M+H)$^+$, 372, 282; NMR $(CDCl_3)$:δ 0.89(d, J=6.9 Hz, 6H), 3.14(t, J=7.5 Hz, 2H).

EXAMPLE 1

1-butyl-3-isobutyl-1,3,8-triazaspiro[4.5]decane-2,4-dione

To a solution of the compound prepared in Reference Example 4 (650 mg) in methanol (3 mL) was added 10% palladium-carbon (65 mg) under an atmosphere of argon. The reaction mixture was stirred for 2 hours under an atmosphere of hydrogen, filtered and then concentrated to give the compound of the present invention (429 mg) having the following physical data.
  TLC: Rf 0.71 (chloroform:methanol:28% ammonia water=80:20:1); Mass: APCI (Pos.) m/z 282 (M+H)$^+$; NMR $(CDCl_3)$:δ 0.88(d, J=6.6 Hz, 6H), 0.94(t, J=7.5 Hz, 3H), 1.34(dq, J=7.5, 7.2 Hz, 2H), 1.62(m, 4H), 1.91(m, 2H), 2.07 (sept., J=7.2 Hz, 1H), 3.06(m, 2H), 3.22(t, J=8.1 Hz, 2H), 3.29(d, J=7.5 Hz, 2H), 3.42(m, 2H).

EXAMPLE 2

1-butyl-3-isobutyl-8-(4-phenoxybenzyl)-1,3,8-triazaspiro[4.5]decane-2,4-dione hydrochloride To a solution of the compound prepared in Example 1 (28.1 mg) in 1% acetic acid in N,N-dimethylformamide (0.5 mL)

were added 4-phenoxybenzaldehyde (21.8 mg) and sodium triacetoxy borohydride (25.4 mg) subsequently, and the mixture was stirred for 8 hours. To the mixture was added 10% acetic acid in methanol (2 mL). The reaction mixture was added to a sulfonic acid resin (Bondesil SCX 40 μm, Valian, product number 1221-3029, 0.6 mmol/g) (1.2 g) which was previously washed with methanol (2 mL, twice), water (2 mL, twice) and (2 mL, twice) subsequently. The resin was washed with methanol (2 mL, three times). The reaction mixture was eluted with 10% triethylamine in methanol (2 mL, three times) and then concentrated. The residue was purified by column chromatography on silica gel (chloroform:methanol=100:1→25:1), dissolved in 4N hydrochloric acid in ethyl acetate and concentrated to give the compound of the present invention (16 mg) having the following physical data.

TLC: Rf 0.77 (chloroform:methanol=10:1); NMR (CD$_3$OD):δ 7.52(m, 2H), 7.39(m, 2H), 7.15(m, 1H), 7.04(m, 4H), 4.37(s, 2H), 3.70(dt, J=3.0, 12.6 Hz, 2H), 3.41(m, 2H), 3.25(m, 2H), 2.40(dt, J=5.1, 13.5 Hz, 2H), 2.03(m, 4H), 1.62 (m, 2H), 1.35(m, 3H), 0.96(t, J=7.2Hz, 3H), 0.88(d, J=6.9 Hz, 6H).

EXAMPLE 2(1) TO 2(3)

Using corresponding aldehyde derivatives instead of 4-phenoxybenzaldehyde, the compounds of the present invention having the following physical data were obtained by the same procedure of Example 2.

EXAMPLE 2(1)

1-butyl-8-[(3,5-dimethyl-1-phenyl-1H-pyrazol-4-yl) methyl]-3-isobutyl-1,3,8-triazaspiro[4.5]decane-2,4-dione hydrochloride TLC: Rf 0.57 (chloroform:methanol=10:1); NMR (CD$_3$OD):δ 7.58-7.44(m, 5H), 2.39(s, 3H).

EXAMPLE 2(2)

1-butyl-8-(2,3-dihydro-1,4-benzodioxin-6-ylmethyl)-3-isobutyl-1,3,8-triazaspiro[4.5]decane-2,4-dione hydrochloride TLC: Rf 0.49 (chloroform:methanol=20:1); NMR (CD$_3$OD):δ 4.27(s, 2H), 4.26(s, 4H).

EXAMPLE 2(3)

1-butyl-3-isobutyl-8-[(2-phenyl-1H-imidazol-5-yl) methyl]-1,3,8-triazaspiro[4.5]decane-2,4-dione dihydrochloride TLC: Rf 0.16 (chloroform:methanol=20:1); NMR (CD$_3$OD):δ 8.00(m, 3H) 4.62(s, 2H).

EXAMPLE 3

1-butyl-3-(cyclohexylmethyl)-8-(4-phenoxybenzyl)-1,3,8-triazaspiro[4.5]decane-2,4-dione hydrochloride Using corresponding bromomethylcyclohexane instead of 1-bromo-2-methylpropane, the compound of the present invention having the following data was obtained by the same procedures as a series of reactions of Reference Example 4→Example 1→Example 2.

TLC: Rf 0.69 (chloroform:methanol=20:1); NMR (CD$_3$OD):δ 7.54(m, 2H), 7.39(m, 2H), 7.18(m, 1H), 7.05(m, 4H), 4.37(s, 2H), 3.69(m, 2H), 3.51(m, 2H), 3.25(m, 4H), 2.39(dt, J=3.9, 14.4 Hz, 2H), 1.98(m, 2H), 1.74-1.58(m, 8H), 1.33(m, 2H), 1.21(m, 3H), 0.96(m, 5H).

EXAMPLE 3(1)

1-butyl-3-(cyclohexylmethyl)-8-[(3,5-dimethyl-1-phenyl-1H-pyrazol-4-yl)methyl]-1,3,8-triazaspiro [4.5]decane-2,4-dione hydrochloride Using 3,5-dimethyl-1-phenyl-1H-pyrazole-4-carbaldehyde instead of 4-phenoxybenzaldehyde, the compound of the present invention having the following physical data was obtained by the same procedure of Example 3.

TLC: Rf 0.56 (chloroform:methanol=20:1); NMR (CD$_3$OD):δ 2.42(s, 3H), 2.01(m, 2H).

EXAMPLE 4

1,3,8-tribenzyl-1,3,8-triazaspiro[4.5]decane-2,4-dione hydrochloride

Using benzylamine hydrochloride instead of butylamine hydrochloride, using bromomethylbenzene instead of 1-bromo-2-methylpropane and using benzaldehyde instead of 4-phenoxybenzaldehyde, the compound of the present invention having the following physical data was obtained by the same procedures as a series of reactions of Reference Example 2→Reference Example 3→Reference Example 4→Example 1→Example 2.

TLC: Rf 0.63 (chloroform:methanol=20:1); NMR (CD$_3$OD):δ 7.48(m, 5H), 4.71(s, 2H).

EXAMPLE 4(1) TO 4(5)

Using benzylamine hydrochloride or 1-phenyl-2-aminoethane hydrochloride instead of it, using bromomethylbenzene or corresponding halogen compounds instead of it, and using aldehyde derivatives instead of benzaldehyde, the compounds of the present invention having the following physical data were obtained by the same procedure of Example 4.

EXAMPLE 4(1)

1,3-dibenzyl-8-[3-(methylthio)propyl]-1,3,8-triazaspiro[4. 5]decane-2,4-dione hydrochloride TLC: Rf 0.19 (chloroform:methanol=20:1); NMR (CD$_3$OD):δ 2.57(t, J=7.2 Hz, 2H), 2.10(s, 3H).

EXAMPLE 4(2)

3-benzyl-8-{4-[3-(dimethylamino)propoxy]benzyl}-1-(2-phenylethyl)-1,3,8-triazaspiro[4.5]decane-2, 4-dione dihydrochloride TLC: Rf 0.55 (chloroform:methanol:triethylamine=9:1: 0.5); NMR (CD$_3$OD):δ 4.14(t, J=5.7 Hz, 2H), 2.94(s, 6H).

EXAMPLE 4(3)

3-(cyclohexylmethyl)-1-(2-phenylethyl)-8-(2,4,6-trimethoxybenzyl)-1,3,8-triazaspiro[4.5]decane-2,4-dione hydrochloride TLC: Rf 0.38 (chloroform:methanol=10:1); NMR (CD$_3$OD): δ 6.31(s, 2H), 3.89(s, 6H).

EXAMPLE 4(4)

3-(cyclobutylmethyl)-1-(2-phenylethyl)-8-(2,4,6-trimethoxybenzyl)-1,3,8-triazaspiro[4.5]decane-2,4-dione hydrochloride TLC: Rf 0.57 (chloroform:methanol=10:1); NMR (CD$_3$OD): δ 3.89(s, 6H), 2.98(t, J=7.2 Hz, 2H).

EXAMPLE 4(5)

3-isobutyl-1-(2-phenylethyl)-8-(2,4,6-trimethoxybenzyl)-1,3,8-triazaspiro[4.5]decane-2,4-dione hydrochloride TLC: Rf 0.54 (chloroform:methanol=10:1); NMR (CD$_3$OD): δ 3.89(s, 6H), 0.91(d, J=6.6 Hz, 6H).

EXAMPLE 5

1-butyl-1,3,8-triazaspiro[4.5]decane-2,4-dione

Using the compound prepared in Reference Example 3 instead of the compound prepared in Reference Example 4, the compound of the present invention having the following data was obtained by the same procedure of Example 1.

TLC: Rf 0.52 (chloroform:methanol:28% ammonia water=80:20:1); NMR (CD$_3$OD): δ 0.94(t, J=7.4 Hz, 3H), 1.23-1.48(m, 4H), 1.65-2.01(m, 4H), 3.13(m, 2H), 3.45(m, 2H), 4.10(m, 2H), 8.06(m, 1H).

EXAMPLE 6

1-butyl-8-(4-phenoxybenzyl)-1,3,8-triazaspiro[4.5]decane-2,4-dione hydrochloride Using the compound prepared in Example 5 instead of the compound prepared in Example 1, the compound of the present invention having the following data was obtained by the same procedure of Example 2.

TLC: Rf 0.59 (chloroform:methanol=10:1); NMR (CD$_3$OD): δ 7.56-7.37(m, 4H), 7.18(m, 1H), 7.04(m, 4H), 4.38(s, 2H), 3.70(m, 1H), 3.34(m, 1H), 3.21(m, 4H), 2.37(dt, J=4.5, 13.8 Hz, 2H), 2.08(d, J=15.0 Hz, 2H), 1.60(m, 2H), 1.35(m, 2H), 0.95(t, J=7.5 Hz, 3H).

EXAMPLE 6(1)

1-butyl-8-[(3,5-dimethyl-1-phenyl-1H-pyrazol-4-yl)methyl]-1,3,8-triazaspiro[4.5]decane-2,4-dione hydrochloride Using 3,5-dimethyl-1-phenyl-1H-pyrazole-4-carbaldehyde instead of 4-phenoxybenzaldehyde, the compound of the present invention having the following data was obtained by the same procedure of Example 6.

TLC: Rf 0.58 (chloroform:methanol=10:1); NMR (CD$_3$OD): δ 4.38(s, 2H), 2.45(s, 3H).

EXAMPLE 7 benzyl4-[3-(4-{[(benzyloxy)carbonyl]amino}butyl)-1-butyl-2,4-dioxo-1,3,8-triazaspiro[4.5]deca-8-yl]butylcarbamate hydrochloride To a solution of the compound prepared in Example 5 (150 mg) in acetone (3 mL) were added potassium carbonate (142 mg) and 4-benzyloxycarbonylaminobutanol methanesulfonate (595 mg) subsequently. The reaction mixture was stirred for 5 hours at 60° C. The reaction mixture was cooled. To the reaction mixture was added water (5 mL) and dichloromethane (5 mL) and then it was separated. The aqueous layer was extracted three times with dichloromethane. The combined organic layer was washed with water and a saturated aqueous solution of sodium chloride subsequently, dried over an anhydrous magnesium sulfate and concentrated. The residue was purified by column chromatography on silica gel (chloroform:methanol=1:0→10:1), dissolved in 4N hydrogen chloride in ethyl acetate (5 mL) and concentrated to give the title compound (229 mg) having the following physical data.

TLC: Rf 0.53 (chloroform:methanol=10:1); NMR (CD$_3$OD): δ 7.33(m, 10H), 5.07(s, 2H), 5.05(s, 2H), 3.68-3.48(m, 6H), 3.29-3.10(m, 8H), 2.38(dt, J=4.5, 14.1 Hz, 2H), 2.00(m, 2H), 1.78(m, 2H), 1.63-1.25(m, 10H), 0.96(t, J=7.2 Hz, 3H).

EXAMPLE 8

1-butyl-3-isobutyl-8-(6-phenylhexyl)-1,3,8-triazaspiro[4.5]decane-2,4-dione hydrochloride To a solution of the compound prepared in Example 1 (28 mg) and N,N-diisopropylethylamine (155 mg) in acetonitrile (3 mL) were added benzenesulfonylchloride resin (Argonaut, product name PS-TsCl, product number 800276, 1.22 mmol/g, 0.20 mmol) (164 mg) and sulfonyl resin (175 mg) which is prepared from 6-phenylhexanol (345 mg). The mixture was stirred for 18 hours at 70° C. and then filtrated. The resin was washed with acetonitrile (3 mL, three times). The filtrate and rinsed solution were combined and concentrated. The residue was purified by column chromatography on silica gel (chloroform:methanol=25:1), added 4N hydrochloric acid in ethyl acetate and concentrated to give the title compound (28 mg) having the following physical data.

TLC: Rf 0.51 (chloroform:methanol=10:1); NMR (CD$_3$OD): δ 7.17(m, 5H), 3.61(m, 4H), 3.25(m, 4H), 3.16(m, 2H), 2.62(t, J=7.2 Hz, 2H), 2.44(m, 2H), 2.02(m, 3H), 1.77(m, 2H), 1.66(m, 4H), 1.39(m, 6H), 0.97(t, J=7.5 Hz, 3H), 0.88(d, J=6.9 Hz, 6H).

REFERENCE EXAMPLE 5

1-butyl-8-(t-butoxycarbonyl)-1,3,8-triazaspiro-[4.5]decane-2,4-dione

To a solution of the compound prepared in Example 5 (326 mg) in water (3 mL) were added potassium carbonate and t-butyl dicarbonate (348 mg) subsequently, and the mixture was stirred for 1 hour at room temperature. The reaction mixture was neutralized with 1N hydrochloric acid. The aqueous layer was extracted three times with ethyl acetate.

The combined organic layer was washed with a saturated aqueous solution of sodium chloride, dried over an anhydrous magnesium sulfate and then concentrated. The residue was purified by column chromatography on silica gel (n-hexane: ethyl acetate=5:1→1:2) to give the title compound (419 mg) having the following physical data.

TLC: Rf 0.32 (n-hexane:ethyl acetate=1:1); NMR (CDCl$_3$):δ 0.94(t, J=7.4 Hz, 3H), 1.48(s, 9H).

REFERENCE EXAMPLE 6

1-butyl-3-(4-benzyloxycarbonylaminobutyl)-8-(t-butoxycarbonyl)-1,3,8-triazaspiro[4.5]decane-2,4-dione Using the compound prepared in Reference Example 5 instead of the compound prepared in Example 5, the title compound having the following data was obtained by the same procedure of Example 7.

TLC: Rf 0.45 (n-hexane:ethyl acetate=1:1); NMR (CDCl$_3$):δ 1.48(s, 9H), 5.10(s, 2H).

EXAMPLE 9 benzyl 3-[1-butyl-2,4-dioxo-8-(2-phenylethyl)-1,3,8-triazaspiro[4.5]deca-3-yl]propylcarbamate hydrochloride The compound prepared in Reference Example 6 was dissolved in 25% trifluoroacetic acid in dichloromethane. The mixture was stirred for 30 minutes at room temperature. The reaction mixture was concentrated. Using the residue instead of the compound prepared in Example 1, the compound of the present invention having the following physical data was obtained by the same procedure of Example 8.

TLC: Rf 0.39 (chloroform:methanol=20:1); NMR (CD$_3$OD):δ 7.34(m, 10H), 5.06(s, 2H), 3.69(m, 4H), 3.54(t, J=6.6 Hz, 2H), 3.38(m, 2H), 3.26(m, 2H), 3.11(m, 2H), 2.40 (dt, J=4.8, 12.6 Hz, 2H), 2.10(m, 2H), 1.81(t, J=6.6 Hz, 2H), 1.64(m, 2H), 1.39(m, 4H), 0.97(t, J=7.5 Hz, 3H).

EXAMPLE 10 methyl [(2S)-9-benzyl-2-isobutyl-3,5-dioxo-1,4,9-triazaspiro[5.5]undeca-4-yl]acetate To a solution of N-benzyl-4-piperidone (189 mg) in methanol (11 mL) were added (2S)-2-amino-4-methylpentanoic acid (157 mg), methyl isocyanoacetate (0.11 mL) and triethylamine (0.14 mL) under an atmosphere of argon, the mixture was stirred overnight at room temperature. The reaction mixture was concentrated and the residue was purified by column chromatography on silica gel (dichloromethane:methanol=50:1→30:1) to give the compound of the present invention (195 mg) having the following physical data.

TLC: Rf 0.38 (chloroform:methanol=10:1); NMR (CDCl$_3$):δ 7.35-7.20(m, 5H), 4.52(d, J=16.5 Hz, 1H), 4.46(d, J=16.5 Hz, 1H), 3.72(s, 3H), 3.64(m, 1H), 3.54(s, 2H), 2.60-2.40(m, 5H), 2.05-1.85(m, 4H), 1.55-1.45(m, 2H), 1.14(d, J=10.8 Hz, 1H), 0.99(d, J=6.3 Hz, 3H), 0.95(d, J=6.3 Hz, 3H).

EXAMPLE 10(1) TO 10(4)

Using N-benzyl-4-piperidone or corresponding piperidone derivatives instead of it, using (2S)-2-amino-4-methylpentanoic acid or corresponding amino acid derivatives instead of it, and using methyl isocyanoacetate or corresponding isonitrile derivatives instead of it, the following compounds were obtained by the same procedure of Example 10.

EXAMPLE 10(1)

(2S)-9-benzyl-4-butyl-2-isobutyl-1,4,9-triazaspiro[5.5]undecane-3,5-dione

TLC: Rf 0.72 (chloroform:methanol=10:1); NMR (d$_6$-DMSO):δ 3.58(m, 1H), 1.00-0.75(m, 9H).

EXAMPLE 10(2)

(2S)-4,9-dibenzyl-2-isobutyl-1,4,9-triazaspiro[5.5]undecane-3,5-dione

TLC: Rf 0.86 (chloroform:methanol=10:1); NMR (CDCl$_3$):δ 4.95(d, J=14.1 Hz, 1H), 4.87(d, J=14.1 Hz, 1H), 3.58(m, 1H).

EXAMPLE 10(3)

(2S)-4,9-dibenzyl-2-(cyclohexylmethyl)-1,4,9-triazaspiro[5.5]undecane-3,5-dione

TLC: Rf 0.7 (chloroform:methanol=10:1); NMR (CDCl$_3$):δ 4.95(d, J=13.8 Hz, 1H), 4.87(d, J=13.8 Hz, 1H), 3.62(m, 1H).

EXAMPLE 10(4)

N-[4-(4-{[(2S)-4-butyl-2-(cyclohexylmethyl)-3,5-dioxo-1,4,9-triazaspiro[5.5]undeca-9-yl]methyl}phenoxy)phenyl]methanesulfonamide hydrochloride TLC: Rf 0.61 (chloroform:methanol=9:1); NMR (CD$_3$OD):δ 4.35(s, 2H), 0.91(t, J=8.4 Hz, 3H).

EXAMPLE 11

(3 S)-1-butyl-3-(cyclohexylmethyl)-9-(4-phenoxybenzyl)-1,4,9-triazaspiro[5.5]undecane-2-one dihydrochloride To a solution of (3S)-1-butyl-2,5-dioxo-3-cyclohexylmethyl-9-(4-phenyloxyphenylmethyl)-1,4,9-triazaspiro[5.5] undecane (the compound is described in Example 40(90) of WO01/40227) (216 mg) in dioxane (10 mL) was added sodium borohydride (77 mg). To the mixture was added acetic acid (0.12 mL) under ice-cooling and then the mixture was stirred at room temperature. The reaction mixture was refluxed for 7 hours. After cooling, the mixture was poured into water. The reaction mixture was extracted with dichloromethane, dried over an anhydrous magnesium sulfate and then concentrated. The residue was purified by preparative thin layer chromatography. Using 4N hydrochloric acid in ethyl acetate, the compound of the present invention (86 mg) having the following physical data was obtained as hydrochloride.

TLC: Rf 0.37 (chloroform:methanol=19:1); NMR (CD$_3$OD):δ 7.57(dt, J=8.7, 2.1 Hz, 2H), 7.39(ddt, J=8.7, 7.5, 2.1 Hz, 2H), 7.18(tt, J=7.5, 1.2 Hz, 1H), 7.05(dt, J=8.7, 2.1 Hz, 2H), 7.03(dq, J=8.7, 1.2 Hz, 2H), 4.37(s, 2H), 4.15(d, J=13.8 Hz, 1H), 4.08(dd, J=8.7, 5.1 Hz, 1H), 3.55(d, J=13.8 Hz, 1H), 3.56-3.33(m, 4H), 2.74-2.46(m, 2H), 2.21(m, 1H), 2.12-1.99(m, 2H), 1.87(m, 1H), 1.84-1.14(m, 15H), 1.10-0.88(m, 2H), 0.94(t, J=7.2 Hz, 3H).

EXAMPLE 12

(3S)-1-butyl-3-(cyclohexylmethyl)-9-(4-phenoxybenzyl)-1,4,9-triazaspiro[5.5]undecane trihydrochloride A suspension of lithium aluminum hydride (73 mg) in tetrahydrofuran (4 mL) was cooled with ice. To the suspension was added (3S)-1-butyl-2,5-dioxo-3-cyclohexylmethyl-9-(4-phenyloxyphenylmethyl)-1,4,9-triazaspiro[5.5]undecane (the compound is described in Example 40(90) of WO01/40227) (211 mg) and the mixture was refluxed overnight. After cooling, to the mixture was added triethanolamine (0.3 mL) and the mixture was stirred for 1 hour at room temperature. To the mixture was added water (0.085 mL) and the mixture was stirred for 4 hours. The reaction mixture was filtered through Celite (trademark). The filtrate was concentrated and purified by column chromatography on silica gel (chloroform:methanol=99:1→19:1). The purified material was dissolved in ethyl acetate. Using 4N hydrochloric acid in ethyl acetate, the compound of the present invention (141 mg) having the following physical data was obtained as hydrochloride.

TLC: Rf 0.19 (chloroform:methanol=9:1); NMR ($d_6$-DMSO):δ 11.90(brs, 1H), 11.27(brs, 1H), 10.47(brs, 1H), 10.31(brs, 1H), 7.57(d, J=8.7 Hz, 2H), 7.42(dd, J=8.7, 7.5 Hz, 2H), 7.18(t, J=7.5 Hz, 1H), 7.09-7.01(m, 4H), 4.39-4.20(m, 3H), 3.76(t, J=5.4 Hz, 1H), 3.63-3.14(m, 11H), 2.84(brs, 2H), 1.86-1.40(m, 10H), 1.38-1.06(m, 5H), 0.95-0.79(m, 2H), 0.90(t, J=7.2 Hz, 3H).

REFERENCE EXAMPLE 7 ethyl (1-benzylpiperidin-4-ylidene)acetate

To a suspension of 60% sodium hydride (1.50 g) in N,N-dimethylformamide (100 mL) was added triethyl phosphonoacetate (5.9 mL) under ice-cooling and the mixture was stirred for 15 minutes. To the mixture was added a solution of N-benzyl-4-piperidone (5.00 g) in N,N-dimethylformamide (100 mL) and the mixture was stirred for 1 hour. To the mixture was added water and the mixture was extracted with ethyl acetate. The organic layer was washed with a saturated aqueous solution of sodium chloride, dried over an anhydrous magnesium sulfate and concentrated. The residue was purified by column chromatography on silica gel (n-hexane:ethyl acetate=2:1) to give the title compound having the following physical data.

TLC: Rf 0.47 (n-hexane:ethyl acetate=2:1); NMR ($CDCl_3$):δ 4.14(q, J=7.0 Hz, 2H), 5.63(s, 1H).

EXAMPLE 13

8-benzyl-1,2,8-triazaspiro[4.5]decan-3-one

To a solution of the compound prepared in Reference Example 7 (1.00 g) in ethanol (5 mL) was added hydrazine monohydrate (0.5 mL) and the mixture was stirred for 2 hours at 80° C. To the reaction mixture was added water and the mixture was extracted with ethyl acetate. The organic layer was washed with a saturated aqueous solution of sodium chloride, dried over an anhydrous magnesium sulfate and concentrated. The residue was washed with t-butyl methyl ether to give the compound of the present invention (0.59 g) having the following physical data.

TLC: Rf 0.14 (chloroform:methanol=10:1); NMR ($CD_3OD$):δ 1.68-1.82(m, 4H), 2.32(s, 2H), 2.32-2.44(m, 2H), 2.55-2.66(m, 2H), 3.53(s, 2H), 7.22-7.34(m, 5H).

EXAMPLE 14

1-butyl-8-benzyl-1,2,8-triazaspiro[4.5]decan-3-one dihydrochloride

Using the compound prepared in Example 13 instead of the compound prepared in Example 1, using butylaldehyde instead of 4-phenoxybenzaldehyde, the compound of the present invention having the following data was obtained by the same procedure of Example 2.

Mass: APCI (Pos.) m/z 302 (M+H)$^+$; TLC: Rf 0.62 (chloroform:methanol=5:1).

EXAMPLE 15

1-butyl-1,2,8-triazaspiro[4.5]decan-3-one dihydrochloride

Using the compound prepared in Example 14 instead of the compound prepared in Reference Example 4, the compound of the present invention having the following data was obtained by the same procedure of Example 1.

TLC: Rf 0.19 (chloroform:methanol=1:1); NMR ($CD_3OD$):δ 0.98(t, J=7.5 Hz, 3H), 1.38-1.50(m, 2H), 1.58-1.68(m, 2H), 2.03-2.11(m, 2H), 2.20-2.29(m, 2H), 2.72(s, 2H), 2.93-2.99(m, 2H), 3.15-3.24(m, 2H), 3.34-3.46(m, 2H).

EXAMPLE 16

N-(4-{4-[(1-butyl-3-oxo-1,2,8-triazaspiro[4.5]deca-8-yl)methyl]phenoxy}phenyl)methanesulfonamide dihydrochloride Using the compound prepared in Example 15 instead of the compound prepared in Example 1, using N-[4-(4-formyl-phenoxy)-phenyl]-methanesulfonamide instead of 4-phenoxybenzaldehyde, the compound of the present invention having the following data was obtained by the same procedure of Example 2.

TLC: Rf 0.23 (chloroform:methanol=10:1); NMR ($CD_3OD$):δ 0.93-0.99(m, 3H), 1.33-1.65(m, 4H), 1.88(m, 1H), 2.20-2.32(m, 4H), 2.69(m, 1H), 2.83(s, 1H), 2.95(s, 3H), 2.97(m, 1H), 3.10-3.24(m, 2H), 3.39(m, 1H), 3.55(m, 1H4), 4.33(s, 2H), 7.03(d, J=9.0 Hz, 2H), 7.06(d, J=9.0 Hz, 2H), 7.29(d, J=9.0 Hz, 2H), 7.52(dd, J=9.0, 2.5 Hz, 2H).

REFERENCE EXAMPLE 8

1-benzyl-4-morpholinoethylaminocarbonyl-4-(N-butyl-N-(2-aminobenzoyl))aminopiperidine Using 2-aminobenzoic acid instead of (2S)-2-amino-4-methylpentanoic acid, using 4-(2-isocyanoethyl)-morpholine instead of benzyl isonitrile, the title compound having the following data was obtained by the same procedure of Example 10.

TLC: Rf 0.24 (chloroform:methanol=10:1); NMR (CD$_3$OD):δ 0.69(t, J=7.0 Hz, 3H), 3.67(t, J=4.5 Hz, 4H).

EXAMPLE 17

1'-benzyl-4-butylspiro[1,4-benzodiazepine-3,4'-piperidine]-2,5(1H,4H)-dione hydrochloride To a solution of the compound prepared in Reference Example 8 (1.77 g) in toluene (40 mL) was added acetic acid (5 mL) and the mixture was stirred for 48 hours at 170° C. To the reaction mixture was added 1N aqueous solution of sodium hydroxide and the mixture was extracted with ethyl acetate. The organic layer was washed with a saturated aqueous solution of sodium chloride, dried over an anhydrous magnesium sulfate and concentrated. The residue was purified by column chromatography on silica gel (methylene chloride:methanol=15:1). Using 4N hydrochloric acid in ethyl acetate, the compound of the present invention (0.1 g) having the following physical data was obtained as hydrochloride.

TLC: Rf 0.45 (chloroform:methanol=10:1); NMR (CD$_3$OD):δ 0.93(t, J=7.0 Hz, 3H), 1.26-1.87(m, 6H), 2.26-2.42(m, 2H), 2.78-2.98(m, 2H), 3.47-3.70(m, 3H), 3.90(m, 1H), 4.27(s, 2H), 7.08(d, J=9.0 Hz, 1H), 7.26(m, 1H), 7.44-7.50(m, 5H), 7.54(m, 1H), 7.81(dd, J=8.0, 1.5 Hz, 1H).

EXAMPLE 18

4-butylspiro[1,4-benzodiazepine-3,4'-piperidine]-2,5(1H,4H)-dione hydrochloride

Using the compound prepared in Example 17 instead of the compound prepared in Reference Example 4, the compound of the present invention having the following data was obtained by the same procedure of Example 1.

TLC: Rf 0.12 (chloroform:methanol=4:1); NMR (CD$_3$OD):δ 0.94(t, J=7.0 Hz, 3H), 1.27-1.39(m, 2H), 1.47-1.67(m, 2H), 1.80(m, 1H), 2.18-2.33(m, 2H), 2.69-2.86(m, 2H), 3.13(m, 1H), 3.44-3.56(m, 3H), 4.05(m, 1H), 7.07(d, J=8.0 Hz, 1H), 7.26(m, 1H), 7.53(m, 1H), 7.83(dd, J=8.0, 1.5 Hz, 1H).

EXAMPLE 19

N-(4-{4-[(4-butyl-2,5-dioxo-1,2,4,5-tetrahydro-1'H-spiro[1,4-benzodiazepine-3,4'-piperidine]-1'-yl)methyl]phenoxy}phenyl)methanesulfonamide hydrochloride Using the compound prepared in Example 18 instead of the compound prepared in Example 1, using N-[4-(4-formylphenoxy)-phenyl]-methanesulfonamide instead of 4-phenoxybenzaldehyde, the compound of the present invention having the following data was obtained by the same procedure of Example 2.

TLC: Rf 0.41 (chloroform:methanol=10:1); NMR (CD$_3$OD):δ 0.94(t, J=7.0 Hz, 3H), 1.27-1.89(m, 6H), 2.24-2.44(m, 2H), 2.74-3.27(m, 2H), 2.95(s, 3H), 3.46-3.72(m, 3H), 3.91(m, 1H), 4.24-4.32(m, 2H), 6.98-7.09(m, 5H), 7.24-7.29(m, 3H), 7.43(d, J=8.5 Hz, 2H), 7.54(m, 1H), 7.82(dd, J=8.0, 1.5 Hz, 1H).

EXAMPLE 20(1) TO 20(81)

Using butylamine hydrochloride or corresponding amine derivatives instead of it, using 1-bromo-2-methylpropane or corresponding halogen compounds instead of it, and using 4-phenoxybenzaldehyde or corresponding aldehyde derivatives instead of it, the compounds of the present invention having the following data were obtained by the same procedures as a series of reactions of Reference Example 1→Reference Example 2→Reference Example 3→Reference Example 4→Example 1→Example 2.

EXAMPLE 20(1)

8-[2-(benzyloxy)benzyl]-3-isobutyl-1-propyl-1,3,8-triazaspiro[4.5]decane-2,4-dione HPLC retention time (minutes): 3.60; Mass: ESI (Pos., 20V) m/z 464 (M+H)$^+$.

EXAMPLE 20(2)

3-(cyclohexylmethyl)-1-propyl-8-(2,4,6-trimethoxybenzyl)-1,3,8-triazaspiro[4.5]decane-2,4-dione HPLC retention time (minutes): 3.62; Mass: ESI (Pos., 20V) m/z 488 (M+H)$^+$.

EXAMPLE 20(3)

3-{[3-(cyclohexylmethyl)-2,4-dioxo-1-propyl-1,3,8-triazaspiro[4.5]deca-8-yl]methyl}benzonitrile HPLC retention time (minutes): 3.47; Mass: ESI (Pos., 20V) m/z 423 (M+H)$^+$.

EXAMPLE 20(4)

4-[3-(cyclohexylmethyl)-2,4-dioxo-1-propyl-1,3,8-triazaspiro[4.5]deca-8-yl]butanoic acid HPLC retention time (minutes): 3.27; Mass: ESI (Pos., 20V) m/z 394 (M+H)$^+$, 308.

EXAMPLE 20(5)

3-(cyclohexylmethyl)-8-(3-phenylpropyl)-1-propyl-1,3,8-triazaspiro[4.5]decane-2,4-dione HPLC retention time (minutes): 3.62; Mass: ESI (Pos., 20V) m/z 426 (M+H)$^+$.

EXAMPLE 20(6)

3-(cyclohexylmethyl)-8-{[4-(4-hydroxy-4-methylpentyl)cyclohex-3-en-1-yl]methyl}-1-propyl-1,3,8-triazaspiro[4.5]decane-2,4-dione HPLC retention time (minutes): 3.60; Mass: ESI (Pos., 20V) m/z 502 (M+H)$^+$.

EXAMPLE 20(7)

3-(cyclohexylmethyl)-8-(2,3-dihydro-1,4-benzodioxin-6-ylmethyl)-1-propyl-1,3,8-triazaspiro[4.5]decane-2,4-dione HPLC retention time (minutes): 3.53; Mass: ESI (Pos., 20V) m/z 456 (M+H)$^+$.

EXAMPLE 20(8)

3-(cyclohexylmethyl)-1-propyl-8-[2-(2,6,6-trimethylcyclohex-1-en-1-yl)ethyl]-1,3,8-triazaspiro[4.5]decane-2,4-dione HPLC retention time (minutes): 3.89; Mass: ESI (Pos., 20V) m/z 458 (M+H)$^+$.

EXAMPLE 20(9)

3-(cyclohexylmethyl)-8-(2-methoxybenzyl)-1-propyl-1,3,8-triazaspiro[4.5]decane-2,4-dione HPLC retention time (minutes): 3.55; Mass: ESI (Pos., 20V) m/z 428 (M+H)$^+$.

EXAMPLE 20(10)

8-(1,1'-biphenyl-4-ylmethyl)-3-(cyclohexylmethyl)-1-propyl-1,3,8-triazaspiro[4.5]decane-2,4-dione HPLC retention time (minutes): 3.77; Mass: ESI (Pos., 20V) m/z 474 (M+H)$^+$.

EXAMPLE 20(11)

3-(cyclohexylmethyl)-1-propyl-8-(thieno-2-ylmethyl)-1,3,8-triazaspiro[4.5]decane-2,4-dione HPLC retention time (minutes): 3.47; Mass: ESI (Pos., 20V) m/z 404 (M+H)$^+$.

EXAMPLE 20(12)

8-(1,3-benzodioxol-4-ylmethyl)-3-(cyclohexylmethyl)-1-propyl-1,3,8-triazaspiro[4.5]decane-2,4-dione HPLC retention time (minutes): 3.51; Mass: ESI (Pos., 20V) m/z 442 (M+H)$^+$.

EXAMPLE 20(13):

3-(cyclohexylmethyl)-8-[(3,5-dimethyl-1-phenyl-1H-pyrazol-4-yl)methyl]-1-propyl-1,3,8-triazaspiro[4.5]decane-2,4-dione HPLC retention time (minutes): 3.53; Mass: ESI (Pos., 20V) m/z 492 (M+H)$^+$.

EXAMPLE 20(14)

1-butyl-3-isobutyl-8-(quinolin-2-ylmethyl)-1,3,8-triazaspiro[4.5]decane-2,4-dione HPLC retention time (minutes): 3.44; Mass: ESI (Pos., 20V) m/z 423 (M+H)$^+$.

EXAMPLE 20(15)

8-(1-benzofuran-2-ylmethyl)-1-butyl-3-isobutyl-1,3,8-triazaspiro[4.5]decane-2,4-dione HPLC retention time (minutes): 3.49; Mass: ESI (Pos., 20V) m/z 412 (M+H)$^+$.

EXAMPLE 20(16)

1-butyl-3-(cyclohexylmethyl)-8-(2,4,6-trimethoxybenzyl)-1,3,8-triazaspiro[4.5]decane-2,4-dione HPLC retention time (minutes): 3.71; Mass: ESI (Pos., 20V) m/z 502 (M+H)$^+$.

EXAMPLE 20(17)

1-butyl-3-(cyclohexylmethyl)-8-[4-(dimethylamino)benzyl]-1,3,8-triazaspiro[4.5]decane-2,4-dione HPLC retention time (minutes): 3.40; Mass: ESI (Pos., 20V) m/z 455 (M+H)$^+$, 336.

EXAMPLE 20(18)

1-butyl-3-(cyclohexylmethyl)-8-(2-methoxybenzyl)-1,3,8-triazaspiro[4.5]decane-2,4-dione HPLC retention time (minutes): 3.64; Mass: ESI (Pos., 20V) m/z 442 (M+H)$^+$.

EXAMPLE 20(19)

3-benzyl-8-(3-phenylpropyl)-1-propyl-1,3,8-triazaspiro[4.5]decane-2,4-dione

HPLC retention time (minutes): 3.47; Mass: ESI (Pos., 20V) m/z 420 (M+H)$^+$.

EXAMPLE 20(20)

3-benzyl-8-[(3-phenyl-1H-pyrazol-4-yl)methyl]-1-propyl-1,3,8-triazaspiro[4.5]decane-2,4-dione HPLC retention time (minutes): 3.31; Mass: ESI (Pos., 20V) m/z 458 (M+H)$^+$.

EXAMPLE 20(21)

3-benzyl-8-(2-ethylhexyl)-1-propyl-1,3,8-triazaspiro[4.5]decane-2,4-dione

HPLC retention time (minutes): 3.62; Mass: ESI (Pos., 20V) m/z 414 (M+H)$^+$.

EXAMPLE 20(22)

3-benzyl-8-(4-chlorobenzyl)-1-propyl-1,3,8-triazaspiro[4.5]decane-2,4-dione

HPLC retention time (minutes): 3.46; Mass: ESI (Pos., 20V) m/z 428, 426 (M+H)$^+$.

EXAMPLE 20(23)

3-benzyl-8-(4-fluorobenzyl)-1-propyl-1,3,8-triazaspiro[4.5]decane-2,4-dione

HPLC retention time (minutes): 3.38; Mass: ESI (Pos., 20V) m/z 410 (M+H)$^+$.

EXAMPLE 20(24)

3-benzyl-1-butyl-8-{[4-(4-hydroxy-4-methylpentyl) cyclohex-3-en-1-yl]methyl}-1,3,8-triazaspiro[4.5] decane-2,4-dione HPLC retention time (minutes): 3.66; Mass: ESI (Pos., 20V) m/z 510 (M+H)$^+$.

EXAMPLE 20(25)

3-benzyl-1-butyl-8-[(3-phenyl-1H-pyrazol-4-yl)methyl]-1,3,8-triazaspiro[4.5]decane-2,4-dione HPLC retention time (minutes): 3.47; Mass: ESI (Pos., 20V) m/z 472 (M+H)$^+$.

EXAMPLE 20(26)

3-benzyl-1-butyl-8-(2-methoxybenzyl)-1,3,8-triazaspiro[4.5]decane-2,4-dione

HPLC retention time (minutes): 3.58; Mass: ESI (Pos., 20V) m/z 436 (M+H)$^+$.

EXAMPLE 20(27)

3-benzyl-1-butyl-8-[(3,5-dimethyl-1-phenyl-1H-pyrazol-4-yl)methyl]-1,3,8-triazaspiro[4.5]decane-2,4-dione HPLC retention time (minutes): 3.60; Mass: ESI (Pos., 20V) m/z 500 (M+H)$^+$, 203.

EXAMPLE 20(28)

3-benzyl-8-[2-(benzyloxy)ethyl]-1-butyl-1,3,8-triazaspiro[4.5]decane-2,4-dione

HPLC retention time (minutes): 3.62; Mass: ESI (Pos., 20V) m/z 472 (M+Na)$^+$, 450 (M+H)$^+$.

EXAMPLE 20(29)

1-benzyl-3-isobutyl-8-(3-phenoxybenzyl)-1,3,8-triazaspiro[4.5]decane-2,4-dione

HPLC retention time (minutes): 3.80; Mass: ESI (Pos., 20V) m/z 498 (M+H)$^+$.

EXAMPLE 20(30)

1-benzyl-3-isobutyl-8-[3-(4-isopropylphenyl)-2-methylpropyl]-1,3,8-triazaspiro[4.5]decane-2,4-dione HPLC retention time (minutes): 3.93; Mass: ESI (Pos., 20V) m/z 388 (M+H)$^+$.

EXAMPLE 20(31)

1-benzyl-8-{[4-(4-hydroxy-4-methylpentyl)cyclohex-3-en-1-yl]methyl}-3-isobutyl-1,3,8-triazaspiro[4.5]decane-2,4-dione HPLC retention time (minutes): 3.64; Mass: ESI (Pos., 20V) m/z 510 (M+H)$^+$.

EXAMPLE 20(32)

1-benzyl-8-[(3,5-dimethyl-1-phenyl-1H-pyrazol-4-yl)methyl]-3-isobutyl-1,3,8-triazaspiro[4.5]decane-2,4-dione HPLC retention time (minutes): 3.57; Mass: ESI (Pos., 20V) m/z 500 (M+H)$^+$.

EXAMPLE 20(33)

1,3-dibenzyl-8-(3-methylbutyl)-1,3,8-triazaspiro[4.5] decane-2,4-dione

HPLC retention time (minutes): 3.60; Mass: ESI (Pos., 20V) m/z 420 (M+H)$^+$.

EXAMPLE 20(34)

1,3-dibenzyl-8-(cyclopropylmethyl)-1,3,8-triazaspiro[4. 5]decane-2,4-dione

HPLC retention time (minutes): 3.47; Mass: ESI (Pos., 20V) m/z 404 (M+H)$^+$.

EXAMPLE 20(35)

1,3-dibenzyl-8-[3-(methylthio)propyl]-1,3,8-triazaspiro[4.5]decane-2,4-dione

HPLC retention time (minutes): 3.53; Mass: ESI (Pos., 20V) m/z 438 (M+H)$^+$.

EXAMPLE 20(36)

1,3-dibenzyl-8-butyl-1,3,8-triazaspiro[4.5]decane-2,4-dione

HPLC retention time (minutes): 3.53; Mass: ESI (Pos., 20V) m/z 406 (M+H)$^+$.

EXAMPLE 20(37)

4-[(1,3-dibenzyl-2,4-dioxo-1,3,8-triazaspiro[4.5] deca-8-yl)methyl]phenylboronic acid HPLC retention time (minutes): 3.47; Mass: ESI (Pos., 20V) m/z 484 (M+H)$^+$.

EXAMPLE 20(38)

1,3-dibenzyl-8-(5-hydroxypentyl)-1,3,8-triazaspiro [4.5]decane-2,4-dione

HPLC retention time (minutes): 3.40; Mass: ESI (Pos., 20V) m/z 436 (M+H)$^+$, 350.

EXAMPLE 20(39)

1,3-dibenzyl-8-((1R,2S,3R, 5R)-2-hydroxy-4,6,8-trioxaspiro[bicyclo[3.3.0]octane-7,1'-cyclohexane]-3-ylmethyl)-1,3,8-triazaspiro[4.5]decane-2,4-dione HPLC retention time (minutes): 3.69; Mass: ESI (Pos., 20V) m/z 584 (M+Na)$^+$, 562 (M+H)$^+$.

EXAMPLE 20(40)

1,3-dibenzyl-8-(1,3-thiazol-2-ylmethyl)-1,3,8-triazaspiro[4.5]decane-2,4-dione

HPLC retention time (minutes): 3.47; Mass: ESI (Pos., 20V) m/z 469 (M+Na)$^+$, 447 (M+H)$^+$.

EXAMPLE 20(41)

N-{4-[(1,3-dibenzyl-2,4-dioxo-1,3,8-triazaspiro[4.5]deca-8-yl)methyl]phenyl}acetamide HPLC retention time (minutes): 3.47; Mass: ESI (Pos., 20V) m/z 497 (M+H)$^+$.

EXAMPLE 20(42)

1,3-dibenzyl-8-propyl-1,3,8-triazaspiro[4.5]decane-2,4-dione

HPLC retention time (minutes): 3.51; Mass: ESI (Pos., 20V) m/z 392 (M+H)$^+$.

EXAMPLE 20(43)

1,3-dibenzyl-8-[(1,5-dimethyl-3-oxo-2-phenyl-2,3-dihydro-1H-pyrazol-4-yl)methyl]-1,3,8-triazaspiro[4.5]decane-2,4-dione HPLC retention time (minutes): 3.51; Mass: ESI (Pos., 20V) m/z 550 (M+H)$^+$.

EXAMPLE 20(44):

1,3-dibenzyl-8-[(3,5-dimethyl-1-phenyl-1H-pyrazol-4-yl)methyl]-1,3,8-triazaspiro[4.5]decane-2,4-dione HPLC retention time (minutes): 3.66; Mass: ESI (Pos., 20V) m/z 534 (M+H)$^+$.

EXAMPLE 20(45)

1,3-dibenzyl-8-[2-(benzyloxy)ethyl]-1,3,8-triazaspiro[4.5]decane-2,4-dione

HPLC retention time (minutes): 3.73; Mass: ESI (Pos., 20V) m/z 484 (M+H)$^+$.

EXAMPLE 20(46)

3-isobutyl-1-(2-phenylethyl)-8-(2,4,6-trimethoxybenzyl)-1,3,8-triazaspiro[4.5]decane-2,4-dione HPLC retention time (minutes): 3.77; Mass: ESI (Pos., 20V) m/z 510 (M+H)$^+$.

EXAMPLE 20(47)

3-isobutyl-8-(3-methylbutyl)-1-(2-phenylethyl)-1,3,8-triazaspiro[4.5]decane-2,4-dione HPLC retention time (minutes): 3.67; Mass: ESI (Pos., 20V) m/z 400 (M+H)$^+$.

EXAMPLE 20(48)

3-isobutyl-8-[3-(methylthio)propyl]-1-(2-phenylethyl)-1,3,8-triazaspiro[4.5]decane-2,4-dione HPLC retention time (minutes): 3.58; Mass: ESI (Pos., 20V) m/z 418 (M+H)$^+$.

EXAMPLE 20(49)

8-butyl-3-isobutyl-1-(2-phenylethyl)-1,3,8-triazaspiro[4.5]decane-2,4-dione

HPLC retention time (minutes): 3.60; Mass: ESI (Pos., 20V) m/z 386 (M+H)$^+$.

EXAMPLE 20(50)

8-[(2E)-3-($^2$-furyl)prop-2-enyl]-3-isobutyl-1-(2-phenylethyl)-1,3,8-triazaspiro[4.5]decane-2,4-dione HPLC retention time (minutes): 3.69; Mass: ESI (Pos., 20V) m/z 436 (M+H)$^+$.

EXAMPLE 20(51)

8-{[4-(4-hydroxy-4-methylpentyl)cyclohex-3-en-1-yl]methyl}-3-isobutyl-1-(2-phenylethyl)-1,3,8-triazaspiro[4.5]decane-2,4-dione HPLC retention time (minutes): 3.75; Mass: ESI (Pos., 20V) m/z 524 (M+H)$^+$.

EXAMPLE 20(52)

8-(2-furylmethyl)-3-isobutyl-1-(2-phenylethyl)-1,3,8-triazaspiro[4.5]decane-2,4-dione HPLC retention time (minutes): 3.56; Mass: ESI (Pos., 20V) m/z 410 (M+H)$^+$.

EXAMPLE 20(53)

8-[2-(benzyloxy)ethyl]-3-isobutyl-1-(2-phenylethyl)-1,3,8-triazaspiro[4.5]decane-2,4-dione HPLC retention time (minutes): 3.75; Mass: ESI (Pos., 20V) m/z 464 (M+H)$^+$.

EXAMPLE 20(54)

3-(cyclohexylmethyl)-1-(2-phenylethyl)-8-(2,4,6-trimethoxybenzyl)-1,3,8-triazaspiro[4.5]decane-2,4-dione HPLC retention time (minutes): 3.95; Mass: ESI (Pos., 20V) m/z 550 (M+H)$^+$.

EXAMPLE 20(55)

3-(cyclohexylmethyl)-8-(cyclopropylmethyl)-1-(2-phenylethyl)-1,3,8-triazaspiro[4.5]decane-2,4-dione HPLC retention time (minutes): 3.75; Mass: ESI (Pos., 20V) m/z 424 (M+H)$^+$.

EXAMPLE 20(56)

8-butyl-3-(cyclohexylmethyl)-1-(2-phenylethyl)-1,3,8-triazaspiro[4.5]decane-2,4-dione HPLC retention time (minutes): 3.82; Mass: ESI (Pos., 20V) m/z 426 (M+H)$^+$.

EXAMPLE 20(57)

3-(cyclohexylmethyl)-8-(5-hydroxypentyl)-1-(2-phenylethyl)-1,3,8-triazaspiro[4.5]decane-2,4-dione HPLC retention time (minutes): 3.53; Mass: ESI (Pos., 20V) m/z 456 (M+H)$^+$.

EXAMPLE 20(58)

3-(cyclohexylmethyl)-8-{4-[3-(dimethylamino)propoxy]benzyl}-1-(2-phenylethyl)-1,3,8-triazaspiro[4.5]decane-2,4-dione HPLC retention time (minutes): 3.45; Mass: ESI (Pos., 20V) m/z 561 (M+H)$^+$.

EXAMPLE 20(59)

8-[2-(benzyloxy)ethyl]-3-(cyclohexylmethyl)-1-(2-phenylethyl)-1,3,8-triazaspiro[4.5]decane-2,4-dione HPLC retention time (minutes): 3.93; Mass: ESI (Pos., 20V) m/z 526 (M+Na)$^+$, 504 (M+H)$^+$.

EXAMPLE 20(60)

3-benzyl-8-(cyclopropylmethyl)-1-(2-phenylethyl)-1,3,8-triazaspiro[4.5]decane-2,4-dione HPLC retention time (minutes): 3.56; Mass: ESI (Pos., 20V) m/z 418 (M+H)$^+$.

EXAMPLE 20(61)

3-benzyl-8-[3-(methylthio)propyl]-1-(2-phenylethyl)-1,3,8-triazaspiro[4.5]decane-2,4-dione HPLC retention time (minutes): 3.62; Mass: ESI (Pos., 20V) m/z 452 (M+H)$^+$, 418.

EXAMPLE 20(62)

3-benzyl-8-butyl-1-(2-phenylethyl)-1,3,8-triazaspiro[4.5]decane-2,4-dione

HPLC retention time (minutes): 3.62; Mass: ESI (Pos., 20V) m/z 420 (M+H)$^+$.

EXAMPLE 20(63)

3-benzyl-8-(5-hydroxypentyl)-1-(2-phenylethyl)-1,3,8-triazaspiro[4.5]decane-2,4-dione HPLC retention time (minutes): 3.44; Mass: ESI (Pos., 20V) m/z 450 (M+H)$^+$, 364.

EXAMPLE 20(64)

3-benzyl-8-{4-[3-(dimethylamino)propoxy]benzyl}-1-(2-phenylethyl)-1,3,8-triazaspiro[4.5]decane-2,4-dione HPLC retention time (minutes): 3.38; Mass: ESI (Pos., 20V) m/z 555 (M+H)$^+$.

EXAMPLE 20(65)

3-benzyl-1-(2-phenylethyl)-8-propyl-1,3,8-triazaspiro[4.5]decane-2,4-dione

HPLC retention time (minutes): 3.53; Mass: ESI (Pos., 20V) m/z 406 (M+H)$^+$.

EXAMPLE 20(66)

3-benzyl-8-[(1,5-dimethyl-3-oxo-2-phenyl-2,3-dihydro-1H-pyrazol-4-yl)methyl]-1-(2-phenylethyl)-1,3,8-triazaspiro[4.5]decane-2,4-dione HPLC retention time (minutes): 3.53; Mass: ESI (Pos., 20V) m/z 564 (M+H)$^+$.

EXAMPLE 20(67)

3-benzyl-8-[2-(benzyloxy)ethyl]-1-(2-phenylethyl)-1,3,8-triazaspiro[4.5]decane-2,4-dione HPLC retention time (minutes): 3.75; Mass: ESI (Pos., 20V) m/z 520 (M+Na)$^+$, 498 (M+H)$^+$.

EXAMPLE 20(68)

3-(cyclohexylmethyl)-1-phenyl-8-(2,4,6-trimethoxybenzyl)-1,3,8-triazaspiro[4.5]decane-2,4-dione HPLC retention time (minutes): 3.71; Mass: ESI (Pos., 20V) m/z 522 (M+H)$^+$.

EXAMPLE 20(69)

1-(2-phenylethyl)-8-(2,4,6-trimethoxybenzyl)-1,3,8-triazaspiro[4.5]decane-2,4-dione Mass:MALDI-TOF m/z 476 (M+Na)$^+$, 454 (M+H)$^+$; NMR (CD$_3$OD):δ 3.89(s, 6H), 2.98(t, J=7.2 Hz, 2H).

EXAMPLE 20(70)

3-methyl-1-(2-phenylethyl)-8-(2,4,6-trimethoxybenzyl)-1,3,8-triazaspiro[4.5]decane-2,4-dione Mass:MALDI-TOF m/z 468 (M+H)$^+$; NMR (CD$_3$OD):δ 3.90(s, 6H) 2.99(s, 3H).

EXAMPLE 20(71)

3-ethyl-1-(2-phenylethyl)-8-(2,4,6-trimethoxybenzyl)-1,3,8-triazaspiro[4.5]decane-2,4-dione Mass:MALDI-TOF m/z 504 (M+Na)$^+$, 482 (M+H)$^+$; NMR (CD$_3$OD):δ 3.89(s, 6H), 1.21(t, J=7.5 Hz, 3H).

EXAMPLE 20(72)

1-(2-phenylethyl)-3-propyl-8-(2,4,6-trimethoxybenzyl)-1,3,8-triazaspiro[4.5]decane-2,4-dione Mass:MALDI-TOF m/z 518 (M+Na)$^+$, 496 (M+H)$^+$; NMR (CD$_3$OD):δ 3.88(s, 6H), 0.96(t, J=7.5 Hz, 3H).

EXAMPLE 20(73)

3-butyl-1-(2-phenylethyl)-8-(2,4,6-trimethoxybenzyl)-1,3,8-triazaspiro[4.5]decane-2,4-dione Mass:MALDI-TOF m/z 510 (M+H)$^+$; NMR (CD$_3$OD):δ 3.89(s, 6H), 0.96(t, J=7.2 Hz, 3H).

EXAMPLE 20(74)

3-pentyl-1-(2-phenylethyl)-8-(2,4,6-trimethoxybenzyl)-1,3,8-triazaspiro[4.5]decane-2,4-dione Mass:MALDI-TOF m/z 546 (M+Na)$^+$, 524 (M+H)$^+$; NMR (CD$_3$OD):δ 3.89(s, 6H), 0.95(t, J=6.9 Hz, 3H).

EXAMPLE 20(75)

3-[(2E)-but-2-enyl]-1-(2-phenylethyl)-8-(2,4,6-trimethoxybenzyl)-1,3,8-triazaspiro[4.5]decane-2,4-dione Mass:MALDI-TOF m/z 530 (M+Na)$^+$, 508 (M+H)$^+$; NMR (CD$_3$OD):δ 5.47(m, 1H), 3.88(s, 6H).

EXAMPLE 20(76)

3-but-3-enyl-1-(2-phenylethyl)-8-(2,4,6-trimethoxybenzyl)-1,3,8-triazaspiro[4.5]decane-2,4-dione Mass:MALDI-TOF m/z 508 (M+H)$^+$; NMR (CD$_3$OD):δ 5.01(m, 2H), 3.84(s, 6H).

EXAMPLE 20(77)

3-but-3-ynyl-1-(2-phenylethyl)-8-(2,4,6-trimethoxybenzyl)-1,3,8-triazaspiro[4.5]decane-2,4-dione Mass:MALDI-TOF m/z 506 (M+H)$^+$; NMR (CD$_3$OD):δ 3.85(s, 6H), 2.38(m, 1H).

EXAMPLE 20(78)

3-but-2-ynyl-1-(2-phenylethyl)-8-(2,4,6-trimethoxybenzyl)-1,3,8-triazaspiro[4.5]decane-2,4-dione Mass:MALDI-TOF m/z 528 (M+Na)$^+$, 506 (M+H)$^+$; NMR (CD$_3$OD):δ 4.20(m, 2H), 3.89(s, 6H).

EXAMPLE 20(79)

3-isobutyl-8-(3-methoxybenzyl)-1-(2-phenylethyl)-1,3,8-triazaspiro[4.5]decane-2,4-dione Mass:MALDI-TOF m/z 472 (M+Na)$^+$, 450 (M+H)$^+$; NMR (CD$_3$OD):δ 3.79(s, 3H), 0.89(d, J=6.6 Hz, 6H).

EXAMPLE 20(80)

8-(2,4-dimethoxybenzyl)-3-isobutyl-1-(2-phenylethyl)-1,3,8-triazaspiro[4.5]decane-2,4-dione Mass:MALDI-TOF m/z 480 (M+H)$^+$; NMR (CD$_3$OD):δ 3.80(s, 3H), 0.89(d, J=6.6 Hz, 6H).

EXAMPLE 20(81)

8-(2,6-dimethoxybenzyl)-3-isobutyl-1-(2-phenylethyl)-1,3,8-triazaspiro[4.5]decane-2,4-dione Mass:MALDI-TOF m/z 480 (M+H)$^+$; NMR (CD$_3$OD):δ 3.82(s, 6H), 0.90(t, J=6.9 Hz, 6H).

EXAMPLE 21

1-benzyl-1'H-spiro[piperidine-4,2'-quinazolin]-4'(3'H)-one dihydrochloride

To a solution of N-benzyl-4-piperidone (4.6 g) in ethanol (100 mL) were added 2-aminobenzamide (2.2 g) and concentrated hydrochloric acid (1 mL) and the mixture was stirred for 1 day. The appeared material was collected by filtration to give the compound of present invention (3.9 g) having the following physical data.

TLC: Rf 0.43 (chloroform:methanol=10:1); NMR (d$_6$-DMSO):δ 2.07-2.19(m, 4H), 3.05-3.60(m, 4H), 4.28(s, 2H), 6.70(t, J=7.5 Hz, 1H), 6.72-7.01(m, 2H), 7.26(t, J=7.5 Hz, 1H), 7.43-7.48(m, 3H), 7.58-7.66(m, 3H), 7.95(s, 1H).

REFERENCE EXAMPLE 9

[1-(phenylmethyl)-4-piperidinylidene]acetonitrile

Using diethyl (cyanomethyl)phosphonate instead of triethyl phosphonoacetate, the title compound (1.78 g) having the following physical data was obtained by the same procedure of Reference Example 7.

TLC: Rf 0.48 (n-hexane:ethyl acetate=1:3);

REFERENCE EXAMPLE 10

[1-benzyl-4-(butylamino)piperidin-4-yl]acetonitrile

To the compound prepared in Reference Example 9 (731 mg) was added 1-butylamine (212 mg) and the mixture was stirred for 64 hours at 90° C. The reaction mixture was cooled and concentrated to give the title compound (116 mg) having the following physical data.

TLC: Rf 0.54 (chloroform:methanol=10:1);

REFERENCE EXAMPLE 11

4-(2-aminoethyl)-1-benzyl-N-butylpiperidine-4-amine

To an ice-cooled suspension of lithium aluminium hydride (60 mg) in tetrahydrofuran (5 mL) was added the compound prepared in Reference Example 10 (148 mg) under an atmosphere of argon. The mixture was stirred for 2.5 hours at 0° C. and then stirred for 1 hour at room temperature. To the reaction mixture was added 1N aqueous solution of sodium hydroxide (0.1 mL) at 0° C. and the mixture was stirred for 5 minutes at 65° C. After cooling, the reaction mixture was filtered and concentrated to give the title compound (118 mg) having the following physical data.

TLC: Rf 0.50 (chloroform:methanol:28% ammonia water=20:5:1);

REFERENCE EXAMPLE 12

1-benzyl-N-butyl-4-{2-[(cyclohexylmethyl)amino]ethyl}piperidine-4-amine

To a solution of the compound prepared in Reference Example 11 (113 mg) in 1,2-dichloroethane (4 mL) were added cyclohexylaldehyde (44 mg) and sodium triacetoxy borohydride (124 mg), and the mixture was stirred for 2.5 hours at room temperature. To the mixture was added 1N aqueous solution of sodium hydroxide (4 mL). The mixture was extracted with chloroform (30 mL), and the organic layer was washed with water, dried over an anhydrous magnesium sulfate and concentrated to give the title compound having the following physical data.

HPLC retention time (minutes): 2.96; Mass: ESI (Pos., 20V) m/z 386 $(M+H)^+$, 315.

EXAMPLE 22

9-benzyl-1-butyl-3-(cyclohexylmethyl)-1,3,9-triazaspiro[5.5]undecan-2-one

To a solution of the compound prepared in Reference Example 12 in dichloromethane (4 mL) was added N,N-diisopropylethylamine (0.202 mL) and the mixture was cooled to −78° C. To the reaction mixture was added triphosgene (39 mg) and the mixture was stirred for 14 hours at room temperature. To the reaction mixture was added a saturated aqueous solution of sodium bicarbonate (5 mL), the mixture was stirred for 10 minutes at room temperature and then extracted with chloroform (30 mL). The organic layer was dried over an anhydrous magnesium sulfate, concentrated and purified by column chromatography on silica gel (n-hexane:ethyl acetate:triethylamine=100:100:1) to give the compound of the present invention (32 mg) having the following physical data.

TLC: Rf 0.75 (chloroform:methanol=10:1); NMR (CD$_3$OD): δ 0.94(m, 5H), 1.28(m, 5H), 1.50(m, 4H), 1.69(m, 6H), 1.99(m, 2H), 2.08(m, 2H), 2.23(m, 2H), 2.81(m, 2H), 3.12(d, J=7.1 Hz, 2H), 3.23(m, 4H), 3.54(s, 2H), 7.29(m, 5H); Mass: ESI (Pos., 20V) m/z 823 $(2M+H)^+$, 412 $(M+H)^+$.

EXAMPLE 22(1)

tert-butyl{3-[2-oxo-9-(2-phenylethyl)-1-propyl-1,3,9-triazaspiro[5.5]undeca-3-yl]propyl}carbamate Using 1-(2-phenylethyl)-4-piperidone instead of N-benzyl-4-piperidone, using 1-propylamine instead of 1-butylamine, and using tert-butyl (3-oxopropyl)carbamate instead of cyclohexylaldehyde, the compound of the present invention having the following data was obtained by the same procedures as a series of reactions of Reference Example 7→Reference Example 10→Reference Example 11→Reference Example 12→Example 22.

TLC: Rf 0.48 (chloroform:methanol=9:1); NMR (CD$_3$OD):δ 0.88(t, J=7.2 Hz, 3H), 1.18-1.34(m, 2H), 1.43(s, 9H), 1.44-1.72(m, 6H), 2.00-2.20(m, 4H), 2.22-2.36(m, 2H), 2.58-2.64(m, 2H), 2.78-2.88 (m, 2H), 2.90-3.10(m, 4H), 3.16-3.40(m, 4H), 7.16-7.36(m, 5H); Mass: MALDI (Pos.) m/z 473 $(M+H)^+$.

EXAMPLE 23

1-butyl-3-(cyclohexylmethyl)-1,3,9-triazaspiro[5.5]undecan-2-one

To a solution of the compound prepared in Example 22 (27.5 mg) in ethanol was added 20% palladium hydroxide (wet, 5 mg). The mixture was stirred for 2 hours at 50° C. under an atmosphere of hydrogen. After cooling, the reaction mixture was filtered through Celite (trademark) and concentrated to give the compound of the present invention (36 mg) having the following physical data.

TLC: Rf 0.84 (chloroform:methanol:28% ammonia water=20:5:1); HPLC retention time (minutes): 3.20; Mass: ESI (Pos., 20V) m/z 643 $(2M+H)^+$, 322 $(M+H)^+$.

EXAMPLE 24(1) TO 24(2)

Using the compound prepared in Example 23 instead of the compound prepared in Example 1, and using 4-phenoxybenzaldehyde or 3,5-dimethyl-1-phenyl-1H-pyrazole-4-carbaldehyde instead of it, the compounds of the present invention having the following data were obtained by the same procedure of Example 2.

EXAMPLE 24(1)

1-butyl-3-(cyclohexylmethyl)-9-(4-phenoxybenzyl)-1,3,9-triazaspiro[5.5]undecan-2-one TLC: Rf 0.31 (dichloromethane:methanol=30:1); NMR (CDCl$_3$):δ 0.92(m, 5H), 1.20(m, 3H), 1.29(m, 2H), 1.50(m, 4H), 1.67(m, 6H), 1.94(m, 2H), 2.07(m, 4H), 2.79(m, 2H), 3.15(m, 4H), 3.26(m, 2H), 3.48(s, 2H), 6.96(m, 2H), 7.01(m, 2H), 7.10(m, 1H), 7.26(m, 2H), 7.33(m, 2H); Mass: FAB (Pos.) m/z 504 $(M+H)^+$, 183.

EXAMPLE 24(2)

1-butyl-3-(cyclohexylmethyl)-9-[(3,5-dimethyl-1-phenyl-1H-pyrazol-4-yl)methyl]-1,3,9-triazaspiro[5.5]undecan-2-one acetate TLC: Rf 0.25(dichloromethane:methanol=30:1); NMR (CDCl$_3$):δ 0.91(m, 5H), 1.17(m, 3H), 1.31(m, 2H), 1.48(m, 4H), 1.65(m, 6H), 1.94(m, 2H), 2.04(s, 3H), 2.13(m, 4H), 2.28(s, 3H), 2.30(s, 3H), 2.96(m, 2H), 3.15(m, 4H), 3.22(m, 2H), 3.49(s, 2H), 6.60(s, 1H), 7.41(m, 5H); Mass: FAB (Pos.) m/z 506 (M+H)$^+$, 185.

EXAMPLE 25

9-benzyl-1-butyl-1,3,9-triazaspiro[5.5]undecan-2-one

To a solution of the compound prepared in Reference Example 11 (406.5 mg) in dimethylformamide (7 mL) were added carbodiimidazole (331.3 mg) and diisopropylethylamine (0.356 mL). The mixture was stirred for 14 hours at 40° C. under an atmosphere of argon. To the reaction mixture was added a saturated aqueous solution of sodium bicarbonate, and the mixture was extracted with ethyl acetate. The organic layer was washed with a saturated aqueous solution of sodium chloride, dried over anhydrous sodium sulfate and then concentrated. The obtained residue was purified by column chromatography on silica gel (dichloromethane:methanol=20:1) to give the compound of the present invention (207.5 mg) having the following physical data.
TLC: Rf 0.73 (chloroform:methanol=9:1); NMR (CDCl$_3$):δ 0.92(t, J=7.2 Hz, 3H), 1.22-1.40(m, 2H), 1.42-1.70(m, 5H), 1.95(brt, J=6.0 Hz, 2H), 2.00-2.21(m, 3H), 2.70-2.84(m, 2H), 3.16-3.38(m, 4H), 3.52(s, 2H), 4.55(s, 1H), 7.20-7.42(m, 5H); Mass: MALDI-TOF (Pos.) m/z 316 (M+H)+.

EXAMPLE 26

9-benzyl-1-butyl-3-(2-methyl-2-propen-1-yl)-1,3,9-triazaspiro[5.5]undecan-2-one

To a solution of the compound prepared in Example 25 (11.0 mg) in dimethylformamide (0.35 mL) was added sodium hydride (60% in mineral oil, 1.54 mg) at 0° C. under an atmosphere of argon. The mixture was stirred 30 minutes at room temperature. To the reaction mixture was added 3-bromo-2-methyl-1-propene (7.03 μL) and the mixture was stirred at 60° C. for 4 hours. After adding water, the reaction mixture was extracted with ethyl acetate. The organic layer was washed with a saturated aqueous solution of sodium chloride, dried and then concentrated. The obtained residue was purified by column chromatography on silica gel (chloroform:methanol=20:1) to give the compound of the present invention (3.8 mg) having the following physical data.
TLC: Rf 0.43 (chloroform:methanol=9:1); NMR (CDCl$_3$):δ 0.87(t, J=7.2 Hz, 3H), 1.20-1.36(m, 2H), 1.40-1.58(m, 2H), 1.58-1.80(m, 1H), 1.63(s, 3H), 1.91(brt, J=6.0 Hz, 2H), 1.92-2.30(m, 5H), 2.75(m, 2H), 3.03(brt, J=6.6 Hz, 2H), 3.28(m, 2H), 3.48(s, 2H), 3.87(s, 2H), 4.71(brs, 1H), 4.79(brs, 1H), 7.12-7.44(m, 5H); Mass: MALDI-TOF (Pos.) m/z 370 (M+H)$^+$.

EXAMPLE 27

9-benzyl-1-butyl-1,3,9-triazaspiro[5.5]undec-4-en-2-one

To a solution of the compound prepared in. Example 25 (35.8 mg) in toluene (3.4 mL) were added 4-chlorobenzonitrile (15.61 mg) and sodium t-butoxide (16.36 mg) under an atmosphere of argon. To the mixture was added palladium diacetate (25.4 mg) and the mixture was stirred for 2 hours at 55° C. After adding water, the reaction mixture was extracted with ethyl acetate. The organic layer was washed with a saturated aqueous solution of sodium chloride, dried and then concentrated. The obtained residue was purified by column chromatography on silica gel (hexane:ethyl acetate=1:1) to give the compound of the present invention (4.7 mg) having the following physical data.
TLC: Rf 0.41 (chloroform:methanol=9:1); NMR (CD$_3$OD):δ 0.93(t, J=7.2 Hz, 3H), 1.20-1.40(m, 4H), 1.41-1.56(m, 2H), 1.60-1.72(m, 2H), 2.00-2.16(m, 2H), 2.20-2.38 (m, 2H), 2.68-2.88(m, 2H), 3.55(s, 2H), 5.09(d, J=7.8 Hz, 1H), 6.08(d, J=7.8 Hz, 1H), 7.20-7.40(m, 5H); Mass: MALDI-TOF (Pos.) m/z 314 (M+H)$^+$.

EXAMPLE 28

9-benzyl-1,3-dibutyl-1,3,9-triazaspiro[5.5]undecan-2-one

To a solution of the compound prepared in Reference Example 11 (37 mg) in dimethylformamide (3.5 mL) were added butanal (30.2 μL), sodium triacetoxy borohydride (70.7 mg) and acetic acid (0.35 mL), the mixture was stirred for 16 hours at room temperature. To the reaction mixture was added 1N aqueous solution of sodium hydroxide and then it was extracted with dichloromethane. The organic layer was dried and concentrated to give a crude product. To a solution of the crude product in dichloromethane (7 mL) was added triphosgene (49.7 mg) at −78° C. under an atmosphere of argon. The mixture was stirred for 30 minutes, and then stirred for 30 minutes at 0° C. To the reaction mixture were added water and sodium bicarbonate. The mixture was extracted with ethyl acetate. The organic layer was washed with a saturated aqueous solution of sodium chloride, dried and concentrated. The obtained residue was purified by column chromatography on silica gel (hexane:ethyl acetate=3:1→2:1) to give the compound of the present invention (6.0 mg) having the following physical data.
TLC: Rf 0.64 (chloroform:methanol=9:1); NMR (CD$_3$OD):δ 0.79-1.00(m, 3H), 0.93(t, J=7.5 Hz, 3H), 1.22-1.40(m, 8H), 1.42-1.58(m, 5H1), 1.94-2.14(m, 3H), 2.17-2.30(m, 2H), 2.76-2.86(m, 2H), 3.18-3.30(m, 4H), 3.54(s, 2H), 7.20-7.38(m, 5H); Mass: MALDI-TOF (Pos.) m/z 372 (M+H)$^+$.

EXAMPLE 28(1)

9-benzyl-1-butyl-3-cyclohexyl-1,3,9-triazaspiro[5.5]undecan-2-one

Using cyclohexanone instead of butanal, the compound of the present invention having the following data was obtained by the same procedure of Example 28.
TLC: Rf 0.68 (chloroform:methanol=9:1); NMR (CD$_3$OD):δ 0.93(t, J=7.5 Hz, 3H), 1.02-1.20(m, 1H), 1.22-1.70(m, 13H), 1.74-1.84(m, 2H), 1.90-1.98(m, 2H), 2.00-2.14(m, 2H), 2.16-2.28(m, 2H), 2.75-2.88(m, 2H), 3.08-3.18 (m, 2H), 3.20-3.28(m, 2H), 3.53(s, 2H), 4.04-4.20(m, 1H), 7.20-7.40(m, 5H); Mass: ESI (Pos., 20V) m/z 795 (M+H)$^+$, 398 (M+H)$^+$.

REFERENCE EXAMPLE 13 benzyl 4-methylene-1-piperidinecarboxylate

A sodium hydride (13.2 g) was added to an anhydrous dimethylsulfoxide (176 mL) and the mixture was heated for 2 hours at 60° C. After cooling, to a suspension of methyltriphenylphosphonium bromide (110.4 g) in dimethylsulfoxide (120 mL) was added the reaction mixture, and the mixture was stirred for 30 minutes at room temperature. To the reaction mixture was added a solution of benzyl 4-oxo-1-piperidinecarboxylate (60 g) in dimethylsulfoxide (150 mL), the mixture was stirred for 1 hour at 50° C. After cooling, to the mixture was added water (2.5 L) and the mixture was extracted with ethyl acetate (1.5 L). The organic layer was washed with a saturated aqueous solution of ammonium chloride (0.5 L) and a saturated aqueous solution of sodium chloride (0.5 L), dried and then concentrated. The obtained residue was purified by column chromatography on silica gel (n-hexane:ethyl acetate:chloroform=9:1:1) to give the title compound (51.1 g) having the following physical data.

Mass: ESI (Pos.) m/z 232 (M+H)$^+$.

REFERENCE EXAMPLE 14 benzyl 1-oxa-6-azaspiro[2.5]octane-6-carboxylate

To a solution of the compound prepared in Reference Example 13 (51.1 g) in chloroform (450 mL) was added sodium dihydrogen phosphate dodecahydrate (95.0 g) and the mixture was cooled to 0° C. To the reaction mixture was added 70% m-chloroperbenzoic acid (65.5 g) and the mixture was stirred for 3 hours at room temperature. Under ice-cooling, to the reaction mixture was added a saturated aqueous solution of sodium thiosulfate (150 mL) and then extracted with ethyl acetate (1 L). The organic layer was washed with a saturated aqueous solution of sodium bicarbonate (0.5 L) and a saturated aqueous solution of sodium chloride (0.5 L), dried and concentrated to give the title compound (52.3 g) having the following physical data.

Mass: ESI (Pos.) m/z 248 (M+H)$^+$.

REFERENCE EXAMPLE 15 benzyl 4-[(benzylamino)methyl]-4-hydroxy-1-piperidinecarboxylate

To a solution of the compound prepared in Reference Example 14 (4 g (0.16 mol)) in 2-propanol (50 mL) was added benzylamine (0.32 mol), the mixture was stirred for 8 hours at 80° C. The reaction mixture was concentrated and purified by column chromatography on silica gel to give the title compound (5.7 g) having the following physical data.

Mass: ESI (Pos.) m/z 355 (M+H)$^+$.

REFERENCE EXAMPLE 16 benzyl 4-{[benzyl(2-fluorobenzoyl)amino]methyl}-4-hydroxy-1-piperidinecarboxylate To a solution of the compound prepared in Reference Example 15 (10 mmol) in dichloromethane (30 mL) was added pyridine (12 mmol). After cooling under 10° C., to the mixture was added 2-fluorobenzoyl chloride (2.4 g) and the mixture was stirred for 2 hours at room temperature. The reaction mixture was added to a saturated aqueous solution of sodium bicarbonate (60 mL), extracted with ethyl acetate (30 mL) and washed with 1N hydrochloric acid (30 mL). The organic layer was washed with a saturated aqueous solution of sodium chloride (30 mL), dried and concentrated. The residue was purified by column chromatography on silica gel to give the title compound (2.7 g) having the following physical data.

Mass: ESI (Pos.) m/z 477 (M+H)$^+$.

EXAMPLE 29 benzyl 5-oxo-4-phenyl-4,5-dihydro-1'H,3H-spiro[1,4-benzoxazepine-2,4'-piperidine]-1'-carboxylate To a solution of the compound prepared in Reference Example 16 (2.7 g) in N,N-dimethylformamide (30 mL) was added 60% sodium hydride (0.45 g) and the mixture was stirred 2 hours and then stirred for 4 days at room temperature. After ice-cooling, to the reaction mixture was added a saturated aqueous solution of ammonium chloride (60 mL) and the mixture was extracted with ethyl acetate (60 mL). The organic layer was washed with water (60 mL), dried and concentrated. The residue was purified by column chromatography on silica gel to give the compound of the present invention (1.5 g) having the following physical data.

Mass: ESI (Pos.) m/z 457 (M+H)$^+$.

EXAMPLE 29(1) TO 29(5)

Using corresponding amine instead of benzylamine, the compounds of the present invention having the following data were obtained by the same procedures as a series of reactions of Reference Example 15→Reference Example 16→Example 29.

EXAMPLE 29(1)

benzyl 5-oxo-4-(2-phenylethyl)-4,5-dihydro-1'H,3H-spiro[1,4-benzoxazepine-2,4'-piperidine]-1'-carboxylate Mass: ESI (Pos.) m/z 471 (M+H)$^+$.

EXAMPLE 29(2)

benzyl 5-oxo-4-propyl-4,5-dihydro-1'H,3H-spiro[1,4-benzoxazepine-2,4'-piperidine]-1'-carboxylate Mass: ESI (Pos.) m/z 409 (M+H)$^+$.

EXAMPLE 29(3)

benzyl 5-oxo-4-cyclopentyl-4,5-dihydro-1'H,3H-spiro[1,4-benzoxazepine-2,4'-piperidine]-1'-carboxylate Mass: ESI (Pos.) m/z 435 (M+H)$^+$.

EXAMPLE 29(4)

benzyl 5-oxo-4-(cyclohexylmethyl)-4,5-dihydro-1'H,3H-spiro [1,4-benzoxazepine-2,4'-piperidine]-1'-carboxylate Mass: ESI (Pos.) m/z 463 (M+H)$^+$.

EXAMPLE 29(5)

benzyl 4-[3-(dimethylamino)propyl]-5-oxo-4,5-dihydro-1'H,3H-spiro[1,4-benzoxazepine-2,4'-piperidine]-1'-carboxylate Mass: ESI (Pos.) m/z 452 (M+H)$^+$.

EXAMPLE 30

4-benzyl-3,4-dihydro-5H-spiro[1,4-benzoxazepine-2,4'-piperidin]-5-one

To a solution of the compound prepared in Example 29 (300 mg) in methanol (5 mL) was added 20% palladium carbon (wet, 60 mg). The mixture was stirred for 5 hours under an atmosphere of hydrogen. The reaction mixture was filtered and the filtrate was concentrated to give the compound of the present invention (209 mg) having the following physical data.

Mass: ESI (Pos.) m/z 323 (M+H)$^+$.

EXAMPLE 30(1) TO 30(5)

Using the compounds prepared in Example 29(1) to 29(5) instead of the compounds prepared in Example 29, the compounds of the present invention having the following data were obtained by the same procedure of Example 30.

EXAMPLE 30(1)

4-(2-phenylethyl)-3,4-dihydro-5H-spiro[1,4-benzoxazepine-2,4'-piperidin]-5-one

Mass: ESI (Pos.) m/z 337 (M+H)$^+$.

EXAMPLE 30(2)

4-propyl-3,4-dihydro-5H-spiro [1,4-benzoxazepine-2,4'-piperidin]-5-one

Mass: ESI (Pos.) m/z 275 (M+H)$^+$.

EXAMPLE 30(3)

4-cyclopentyl-3,4-dihydro-5H-spiro[1,4-benzoxazepine-2,4'-piperidin]-5-one

Mass: ESI (Pos.) m/z 301 (M+H)$^+$.

EXAMPLE 30(4)

4-(cyclohexylmethyl)-3,4-dihydro-5H-spiro[1,4-benzoxazepine-2,4'-piperidin]-5-one Mass: ESI (Pos.) m/z 329 (M+H)$^+$.

EXAMPLE 30(5)

4-[3-(dimethylamino)propyl]-3,4-dihydro-5H-spiro [1,4-benzoxazepine-2,4'-piperidin]-5-one Mass: ESI (Pos.) m/z 318 (M+H)$^+$.

EXAMPLE 31

4-benzyl-1'-(3-phenylpropyl)-3,4-dihydro-5H-spiro [1,4-benzoxazepine-2,4'-piperidin]-5-one To a solution of the compound prepared in Example 30 (0.01 mmol) in tetrahydrofuran (0.4 mL) were added 3-phenylpropanal (0.02 mmol) and MP-BH(OAc)$_3$ (Argonaut, product number 800415, loading; 2.25 mmol/g) (13.3 mg). The mixture was stirred overnight at 25° C. To the reaction mixture were added tetrahydrofuran (0.4 mL) and PS-NHNH$_2$ (Argonaut, product number 800272, loading; 3.65 mmol/g) (8.2 mg). After stirring overnight, the mixture was filtered and the filtrate was concentrated to give the compound of the present invention having the following physical data.

Mass: ESI (Pos., 20V) m/z 441 (M+H)$^+$, 265; HPLC retention time (minutes): 3.42.

EXAMPLE 31(1) TO 31(11)

Using the compounds prepared in Example 30(1) to 30(5) instead of the compound prepared in Example 31, using corresponding aldehyde instead of 3-phenylpropanal, the compounds of the present invention having the following data were obtained by the same procedure of Example 31.

EXAMPLE 31(1)

4-benzyl-1'-(cyclopentylmethyl)-3,4-dihydro-5H-spiro[1,4-benzoxazepine-2,4'-piperidin]-5-one Mass: ESI (Pos., 20V) m/z 809 (2M+H)$^+$, 405 (M+H)$^+$; HPLC retention time (minutes): 3.31.

EXAMPLE 31(2)

4-benzyl-1'-heptyl-3,4-dihydro-5H-spiro[1,4-benzoxazepine-2,4'-piperidin]-5-one

Mass: ESI (Pos., 20V) m/z 841 (2M+H)$^+$, 421 (M+H)$^+$, 225; HPLC retention time (minutes): 3.51.

EXAMPLE 31(3)

1'-(cyclopentylmethyl)-4-(2-phenylethyl)-3,4-dihydro-5H-spiro[1,4-benzoxazepine-2,4'-piperidin]-5-one Mass: ESI (Pos., 20V) m/z 837 (2M+H)$^+$, 419 (M+H)$^+$; HPLC retention time (minutes): 3.34.

EXAMPLE 31(4)

1'-butyl-4-(2-phenylethyl)-3,4-dihydro-5H-spiro[1,4-benzoxazepine-2,4'-piperidin]-5-one Mass: ESI (Pos., 20V) m/z 785 (2M+H)$^+$, 393 (M+H)$^+$; HPLC retention time (minutes): 3.29.

EXAMPLE 31(5)

4-{[5-oxo-4-(2-phenylethyl)-4,5-dihydro-1'H,3H-spiro[1,4-benzoxazepine-2,4'-5-piperidine]-1'-yl]methyl}benzonitrile Mass: ESI (Pos., 20V) m/z 903 (2M+H)$^+$, 452 (M+H)$^+$; HPLC retention time (minutes): 3.31.

EXAMPLE 31(6)

4-cyclopentyl-1'-[(3,5-dimethyl-1-phenyl-1H-pyrazol-4-yl)methyl]-3,4-dihydro-5H-spiro[1,4-benzoxazepine-2,4'-piperidin]-5-one Mass: ESI (Pos., 20V) m/z 969 (2M+H)$^+$, 485 (M+H)$^+$, 201, 185; HPLC retention time (minutes): 3.29.

EXAMPLE 31(7)

4-cyclopentyl-1'-(4-methoxybenzyl)-3,4-dihydro-5H-spiro[1,4-benzoxazepine-2,4'-piperidin]-5-one Mass: ESI (Pos., 20V) m/z 841 (2M+H)$^+$, 421 (M+H)$^+$; HPLC retention time (minutes): 3.27.

EXAMPLE 31(8)

4-(cyclohexylmethyl)-1'-(3-phenylpropyl)-3,4-dihydro-5H-spiro[1,4-benzoxazepine-2,4'-piperidin]-5-one Mass: ESI (Pos., 20V) m/z 893 (2M+H)$^+$, 447 (M+H)$^+$; HPLC retention time (minutes): 3.51.

EXAMPLE 31(9)

4-(cyclohexylmethyl)-1'-[(3,5-dimethyl-1-phenyl-1H-pyrazol-4-yl)methyl]-3,4-dihydro-5H-spiro[1,4-benzoxazepine-2,4'-piperidin]-5-one Mass: ESI (Pos., 20V) m/z 513 (M+H)$^+$, 201, 185; HPLC retention time (minutes): 3.45.

EXAMPLE 31(10)

1'-heptyl-4-propyl-3,4-dihydro-5H-spiro[1,4-benzoxazepine-2,4'-piperidin]-5-one

Mass: ESI (Pos., 20V) m/z 745 (2M+H)$^+$, 373 (M+H)$^+$; HPLC retention time (minutes): 3.4.

EXAMPLE 31(11)

4-[3-(dimethylamino)propyl]-1'-(3-phenylpropyl)-3,4-dihydro-5H-spiro[1,4-benzoxazepine-2,4'-piperidin]-5-one Mass: ESI (Pos., 20V) m/z 436 (M+H)$^+$, 218; HPLC retention time (minutes): 3.05.

EXAMPLE 32

4-benzyl-1'-(cyclopentylcarbonyl)-3,4-dihydro-5H-spiro[1,4-benzoxazepine-2,4'-piperidin]-5-one To a solution of the compound prepared in Example 30 (0.010 mmol) in dichloroethane (0.7 mL) were added cyclopentanecarbonylchloride (0.020 mmol) and poly(4-vinylpyridine) (2% cross-linked, Aldrich, CAS#9017-40-7) (5.3 mg). The mixture was stirred overnight at 25° C. To the reaction mixture was added PS-trisamine (Argonaut, product number 800229, loading; 4.36 mmol/g) (6.9 mg), and the mixture was stirred overnight at 25° C. The mixture was filtered and the filtrate was concentrated to give the compound of the present invention having the following physical data.

Mass: ESI (Pos., 20V) m/z 837 (2M+H)$^+$, 419 (M+H)$^+$; HPLC retention time (minutes): 3.82.

EXAMPLE 33

4-benzyl-N-cyclopentyl-5-oxo-4,5-dihydro-1H,3H-spiro[1,4-benzoxazepine-2,4'-piperidine]-1'-carboxamide To a solution of the compound prepared in Example 30 (0.010 mmol) in dichloroethane (0.7 mL) was added cyclopentylisocyanate (0.020 mmol), the mixture was stirred overnight at 25° C. To the reaction mixture was added PS-trisamine (Argonaut, product number 800229, loading; 4.36 mmol/g) (6.9 mg). After stirring overnight at 25° C., the mixture was filtered and the filtrate was concentrated to give the compound of the present invention having the following physical data.

Mass: ESI (Pos., 20V) m/z 867 (2M+H)$^+$, 434 (M+H)$^+$; HPLC retention time (minutes): 3.69.

EXAMPLE 34

9-benzyl-1-butyl-3-(cyclohexylmethyl)-2-thia-1,3,9-triazaspiro[5.5]undecane-2,2-dioxide To a solution of the compound prepared in Reference Example 12 (183.8 mg) in anhydrous dichloromethane (6 mL) were added diisopropylethylamine (0.422 mL) and sulfuryl chloride (35.1 μL) at −78° C. under an atmosphere of argon. The mixture was stirred for 1.5 hours at 0° C. To the reaction mixture was added water, and the mixture was extracted with ethyl acetate. The organic layer was washed with a saturated aqueous solution of sodium chloride, dried and then concentrated. The obtained residue was purified by column chromatography on silica gel (hexane:ethyl acetate=3:2) to give the compound of the present invention (0.9 mg) having the following physical data.

TLC: Rf 0.59 (chloroform:methanol=9:1); NMR (CD$_3$OD):δ 0.82-0.98(m, 2H), 0.92(t, J=7.2 Hz, 3H), 1.16-1.38(m, 8H), 1.46-1.60(m, 2H), 1.60-1.92(m, 7H), 1.98-2.11 (m, 2H), 2.16-2.28(m, 2H), 2.70-2.80(m, 2H), 2.88(d, J=7.2 Hz, 2H), 3.04-3.16(m, 2H), 3.41-3.49(m, 2H), 3.52(s, 2H), 7.20-7.40(m, 5H); Mass: MALDI (Pos.) m/z 448 (M+H)$^+$.

REFERENCE EXAMPLE 17

2-(1-benzyl-4-piperidinylidene)ethanol

To a solution of the compound prepared in Reference Example 7 (7.15 g) in anhydrous tetrahydrofuran (50 mL) was added dropwise a solution of diisobutylaluminum hydride in toluene (1.01M, 88 mL) at −78° C. under an atmosphere of argon. The mixture was stirred 3 hours. To the mixture was added methanol and the mixture was stirred for 1 hour. An insoluble material was removed by filtration and the filtrate was concentrated to give the title compound (5.21 g) having the following physical data.

TLC: Rf 0.50(ethyl acetate:methanol:triethylamine=20:2:1); NMR (CDCl$_3$):δ 7.11-7.39(m, 5H), 5.41(t, J=7.1 Hz, 1H), 4.14(d, J=7.1 Hz, 2H), 3.51(s, 2H), 2.40-2.50(m, 4H), 2.28-2.38(m, 2H), 2.21-2.28(m, 2H).

REFERENCE EXAMPLE 18

2-(1-benzyl-4-piperidinylidene)ethyl 2,2,2-trichloroethaneimidate

To a solution of the compound prepared in Reference Example 17 (4.90 g) in anhydrous tetrahydrofuran (60 mL)

was added sodium hydride (60% in oil, 180 mg) at 0° C. under an atmosphere of argon and the mixture was stirred for 15 minutes. To the mixture was added trichloroacetonitrile (2.70 mL) and the mixture was stirred for 2 hours at 0° C. The reaction mixture was concentrated, neutralized with 1N hydrochloric acid and concentrated. The obtained residue was purified by column chromatography on silica gel (hexane:ethyl acetate=3:1) to give the title compound (6.25 g) having the following physical data.

TLC: Rf 0.31 (hexane:ethyl acetate=3:1); NMR (CDCl$_3$): δ 8.25(s, 1H), 7.22-7.36(m, 5H), 5.47(t, J=7.1 Hz, 1H), 4.80(d, J=7.1 Hz, 2H), 3.51(s, 2H), 2.42-2.51(m, 4H), 2.33-2.41(m, 2H), 2.24-2.32(m, 2H).

REFERENCE EXAMPLE 19

N-(1-benzyl-4-vinyl-4-piperidinyl)-2,2,2-trichloroacetamide

A solution of the compound prepared in Reference Example 19 (6.10 g) in xylene (100 mL) was refluxed for 17 hours at 140° C. The reaction mixture was concentrated. The obtained residue was purified by column chromatography on silica gel (hexane:ethyl acetate=4:1→3:1) to give the title compound (1.94 g) having the following physical data.

TLC: Rf 0.60(ethyl acetate); NMR (CDCl$_3$): δ 7.21-7.39 (m, 5H), 6.40(s, 1H), 5.94(dd, J=17.4, 10.8 Hz, 1H), 5.20(d, J=17.4 Hz, 1H), 5.18(d, J=10.8 Hz, 1H), 3.52(s, 2H), 2.66-2.78(m, 2H), 2.11-2.29(m, 4H), 1.84-1.98(m, 2H); Mass: ESI (Pos., 20V) m/z 366, 364, 362 (M+H)$^+$, 200.

REFERENCE EXAMPLE 20

1-benzyl-4-vinyl-4-piperidinamide

To a solution of the compound prepared in Reference Example 19 (170 mg) in methanol (3 mL) was added 5N aqueous solution of sodium hydroxide (3 mL) and the mixture was stirred for 5 hours at 60° C. The reaction mixture was concentrated, added water and extracted with dichloromethane. The organic layer was dried over anhydrous sodium sulfate and then concentrated. The obtained residue was purified by column chromatography on silica gel (ethyl acetate:methanol:triethylamine=20:2:1) to give the title compound (38 mg) having the following physical data.

TLC: Rf 0.26 (chloroform:methanol:28% ammonia water=80:10:1); NMR (CDCl$_3$): δ 7.20-7.39(m, 5H), 5.92(dd, J=17.5, 10.7 Hz, 1H), 5.14(d, J=17.5 Hz, 1H), 5.02(d, J=10.1 Hz, 1H), 3.55(s, 2H), 2.38-2.66(m, 4H), 1.73-1.86(m, 2H), 1.34-1.58(m, 2H).

REFERENCE EXAMPLE 21

1-benzyl-N-butyl-4-vinyl-4-piperidineamine

To a solution of the compound prepared in Reference Example 20 (250 mg) in dichloromethane (6 mL) were added butanal (0.104 mL) and sodium triacetoxy borohydride (292 mg) and the mixture was stirred for 2 hours at 0° C. To the reaction mixture was added 2N aqueous solution of sodium hydroxide and the mixture was extracted with dichloromethane. The organic layer was dried over anhydrous sodium sulfate, concentrated and purified by column chromatography on silica gel (ethyl acetate:methanol:triethylamine=50:5:1) to give the title compound (268 mg) having the following physical data.

TLC: Rf 0.43(ethyl acetate:methanol:triethylamine=20:2:1); NMR (CDCl$_3$): δ 7.20-7.36(m, 5H), 5.64(dd, J=17.7, 10.9 Hz, 1H), 5.14(dd, J=10.9 Hz, 1.3 Hz, 1H), 5.03(dd, J=17.7 Hz, 1.3 Hz, 1H), 3.50(s, 2H), 2.35-2.51(m, 6H), 1.68-1.80(m, 2H), 1.57-1.68(m, 2H), 1.25-1.48(m, 5H), 0.90(t, J=7.1 Hz, 3H).

REFERENCE EXAMPLE 22

N-(1-benzyl-4-vinyl-4-piperidinyl)-N-butyl-N'-(cyclohexylmethyl)urea

To a solution of cyclohexylacetic acid (300 mg) in toluene (5 mL) were added triethylamine (0.287 mL) and diphenylphosphoryl azide (0.498 mL) and the mixture was stirred for 1 hour at room temperature and then stirred for 2 hours at 100° C. The reaction mixture was washed with a saturated aqueous solution of sodium bicarbonate and a saturated aqueous solution of sodium chloride, subsequently, and then dried. To the solution was added the compound prepared in Reference Example 21 (200 mg) and the mixture was stirred for 5 hours at room temperature. The reaction mixture was concentrated. The obtained residue was purified by column chromatography on silica gel (ethyl acetate→ethyl acetate:methanol:triethylamine=100:5:1) to give the title compound (253 mg) having the following physical data.

TLC: Rf 0.67(ethyl acetate:methanol:triethylamine=20:2:1); NMR (CDCl$_3$): δ 7.22-7.33(m, 5H), 6.13(dd, J=17.7, 10.9 Hz, 1H), 5.22(dd, J=10.9, 1.0 Hz, 1H), 5.14(dd, J=17.7, 1.0 Hz, 1H), 4.62-4.70(m, 1H), 3.49(s, 2H), 3.21-3.32(m, 2H), 3.01(t, J=6.6 Hz, 2H), 2.52-2.63(m, 2H), 2.31-2.42(m, 2H), 2.06-2.22(m, 4H), 1.50-1.79(m, 7H), 1.06-1.49(m, 6H), 0.93 (t, J=7.3 Hz, 3H), 0.83-0.94(m, 2H); Mass: ESI (Pos., 20V) m/z 412 (M+H)$^+$, 200.

EXAMPLE 35

8-benzyl-1-butyl-3-(cyclohexylmethyl)-4-methyl-1,3,8-triazaspiro[4.5]decan-2-one To a solution of the compound prepared in Reference Example 22 (20 mg) in N,N-dimethylformamide (0.4 mL) was added sodium hydride (60% in oil, 7.8 mg) at 0° C. under an atmosphere of argon, and the mixture was stirred for 1 hour at 80° C. The reaction mixture was concentrated, added methanol at 0° C. and then concentrated. The obtained residue was purified by column chromatography on silica gel (hexane:ethyl acetate=2:1) to give the compound of the present invention (15.6 mg) having the following physical data.

TLC: Rf 0.52 (hexane:ethyl acetate=1:2) NMR (CDCl$_3$): δ 7.21-7.39(m, 5H), 3.48(s, 2H), 3.42-3.52(m, 1H), 3.32-3.42 (m, 1H), 3.23-3.32(m, 1H), 2.82-2.92(m, 2H), 2.69-2.81(m, 1H), 2.60(dd, J=13.8, 5.6 Hz, 1H), 2.01-2.13(m, 1H), 1.83-1.92(m, 1H), 1.58-1.79(m, 9H), 1.09-1.58(m, 10H), 1.01(d, J=6.2 Hz, 3H), 0.90(t, J=7.1 Hz, 3H); Mass: ESI (Pos., 20V) m/z 823 (2M+H)$^+$, 412 (M+H)$^+$.

EXAMPLE 36

3-(3-aminopropyl)-9-(2-phenylethyl)-1-propyl-1,3,9-triazaspiro[5.5]undecan-2-one To the compound prepared in Example 22(1) (12.0 mg) was added 4N solution of hydrochloric acid in ethyl acetate (2 mL) and the mixture was stirred for 3 days at 40° C. The mixture was raised to 60° C. To the mixture was added methanol (0.1 mL) and then the mixture was stirred for 3 hours and concentrated to give the compound of the present invention (9.3 mg) having the following physical data.

TLC: Rf 0.44 (chloroform:methanol:28% ammonia water=5:1:0.1); NMR (CD$_3$OD):δ 0.91(t, J=7.5 Hz, 3H), 1.26-1.32(m, 2H), 1.48-1.64(m, 4H), 1.84-1.98(m, 4H), 2.16-2.23(m, 2H), 2.30-2.48(m, 2H), 2.84-2.94(m, 2H), 3.02-3.70 (m, 2H), 7.20-7.40(m, 5H); Mass: MALDI (Pos.) m/z 373 (M+H)$^+$.

EXAMPLE 37 phenylmethyl{3-[2-oxo-9-(2-phenylethyl)-1-propyl-1,3,9-triazaspiro[5.5]undeca-3-yl]propyl}carbamate To a solution of the compound prepared in Example 36 (9.3 mg) in water (2.5 mL) were added sodium carbonate (13.22 mg) and benzyloxycarbonyl chloride (0.01782 mL) at 0° C. The mixture was stirred for 30 minutes at room temperature. To the reaction mixture was added water and the mixture was extracted with ethyl acetate. The organic layer was washed with a saturated aqueous solution of sodium chloride, dried and concentrated. The obtained residue was purified by preparative thin layer chromatography on silica gel (chloroform:methanol=9:1) to give the compound of the present invention (6.3 mg) having the following physical data.

TLC: Rf 0.63 (chloroform:methanol=9:1); NMR (CD$_3$OD):δ 0.87(t, J=7.2 Hz, 3H), 1.26-1.36(m, 2H), 1.44-1.62(m, 4H), 1.67(quint, J=6.3 Hz, 2H), 1.94-2.15(m, 4H), 2.20-2.34(m, 2H), 2.56-2.66(m, 2H), 2.76-2.85(m, 2H), 2.88-3.00(m, 2H), 3.10(t, J=6.3 Hz, 2H), 3.15-3.25(m, 2H), 3.26-3.37(m, 2H), 5.05(s, 2H), 7.14-7.40(m, 10H); Mass: MALDI (Pos.) m/z 507 (M+H)$^+$.

REFERENCE EXAMPLE 23 tert-butyl 4-(2-ethoxy-2-oxoethylidene)-1-piperidinecarboxylate

Using N-(tert-butoxycarbonyl)-4-piperidone instead of N-benzyl-4-piperidone, the compound of the present invention having the following data was obtained by the same procedure of Reference Example 7.

TLC: Rf 0.26 (hexane:ethyl acetate=1:1); NMR (CDCl$_3$):δ 5.71(s, 1H), 4.16(q, J=7.1 Hz, 2H), 3.41-3.57(m, 4H), 2.88-2.99(m, 2H), 2.23-2.33(m, 2H), 1.47(s, 9H), 1.28(t, J=7.1 Hz, 3H).

REFERENCE EXAMPLE 24 tert-butyl 4-(2-hydroxyethylidene)-1-piperidinecarboxylate

To a solution of the compound prepared in Reference Example 23 (24.4 g) in anhydrous tetrahydrofuran (250 mL) was added dropwise diisobutylaluminum hydride (1.01M solution in hexane, 224 mL) at −78° C. under an atmosphere of argon. The mixture was stirred for 2 hours. The reaction mixture was poured into ice-cooled 1N hydrochloric acid and then extracted with dichloromethane. The organic layer was dried and concentrated to give the title compound (19.5 g) having the following physical data.

TLC: Rf 0.25 (hexane:ethyl acetate=1:1); NMR (CDCl$_3$):δ 5.49(t, J=7.0 Hz, 1H), 4.18(d, J=7.0 Hz, 2H), 3.37-3.49(m, 4H), 2.23-2.31(m, 2H), 2.15-2.22(m, 2H), 1.47(s, 9H).

REFERENCE EXAMPLE 25 tert-butyl 4-{2-[(2,2,2-trichloroethanimidoyl)oxy]ethylidene}-1-piperidinecarboxylate To a solution of the compound prepared in Reference Example 24 (19.5 g) in tetrahydrofuran (200 mL) was added sodium hydride (60% in oil, 377 mg) at 0° C. under an atmosphere of argon. The mixture was stirred for 30 minutes. To the mixture was added trichloroacetonitrile (9.03 mL) and the mixture was stirred for 2 hours at 0° C. The reaction mixture was neutralized with 1N hydrochloric acid and then extracted with ethyl acetate. The organic layer was washed with a saturated aqueous solution of sodium chloride, dried and then concentrated. The obtained residue was purified by column chromatography on silica gel (hexane:ethyl acetate=10:1) to give the title compound (25.6 g) having the following physical data.

TLC: Rf 0.60 (hexane:ethyl acetate=3:1); NMR (CDCl$_3$):δ 8.28(s, 1H), 5.57(t, J=7.0 Hz, 1H), 4.82(d, J=7.0 Hz, 2H), 3.39-3.49(m, 4H), 2.28-2.36(m, 2H), 2.18-2.26(m, 2H), 1.47 (s, 9H).

REFERENCE EXAMPLE 26 tert-butyl 4-[(trichloroacetyl)amino]-4-vinyl-1-piperidinecarboxylate

A solution of the compound prepared in Reference Example 25 (5.20 g) in xylene (100 mL) was refluxed at 130° C. for 1 day. The reaction mixture was concentrated and the obtained residue was purified by column chromatography on silica gel (hexane:ethyl acetate=6:1) to give the title compound (4.77 g) having the following physical data.

TLC: Rf 0.54 (hexane:ethyl acetate=3:1); NMR (CDCl$_3$):δ 6.46(s, 1H), 5.94(dd, J=17.4 Hz, 10.8 Hz, 1H), 5.24(d, J=10.8 Hz, 1H), 5.25(d, J=17.4 Hz, 1H), 3.73-3.91(m, 2H), 3.07-3.21(m, 2H), 2.10-2.26(m, 2H), 1.74-1.88(m, 2H), 1.42-1.50 (m, 9H).

REFERENCE EXAMPLE 27 tert-butyl 4-amino-4-vinyl-1-piperidinecarboxylate

To a solution of the compound prepared in Reference Example 26 (500 mg) in methanol (5 mL) was added 5N aqueous solution of sodium hydroxide (5 mL) and the mixture was stirred for 7 hours at 60° C. The reaction mixture was concentrated, added water and then extracted with dichloromethane. The organic layer was dried over anhydrous sodium sulfate and then concentrated. The obtained residue was purified by column chromatography on silica gel (ethyl acetate:methanol:triethylamine=100:10:1) to give the title compound (282 mg) having the following physical data.

TLC: Rf 0.48(ethyl acetate:methanol:triethylamine=20:2: 1); NMR (CDCl$_3$):δ 5.90(dd, J=17.5, 10.7 Hz, 1H), 5.14(d, J=17.5 Hz, 1H), 5.05(d, J=10.7 Hz, 1H), 3.51-3.65(m, 2H), 3.33-3.44(m, 2H), 1.59-1.72(m, 2H), 1.46(s, 9H), 1.21-1.44 (m, 2H).

REFERENCE EXAMPLE 28 tert-butyl 4-(butylamino)-4-vinyl-1-piperidinecarboxylate

To a solution of the compound prepared in Reference Example 27 (2.23 g) in dichloromethane (40 mL) was added butanal (0.933 mL) and the mixture was stirred 2 hours at room temperature. To the mixture was added sodium triacetoxy borohydride (2.50 g) at 0° C. and the mixture was stirred for 2 hours at room temperature. The reaction mixture was made alkaline with addition of 1N aqueous solution of sodium hydroxide, extracted with dichloromethane, dried over anhydrous sodium sulfate, and then concentrated. The obtained residue was purified by column chromatography on silica gel (ethyl acetate:methanol=10:1) to give the title compound (2.60 g) having the following physical data.
TLC: Rf0.36(ethyl acetate:methanol=10:1); NMR (CDCl$_3$):δ 5.62(dd, J=17.7, 10.9 Hz, 1H), 5.19(d, J=10.9 Hz, 1H), 5.03(d, J=17.7 Hz, 1H), 3.35-3.53(m, 4H), 2.37-2.45(m, 2H), 1.68-1.79(m, 1H), 1.49-1.67(m, 4H), 1.45(s, 9H), 1.26-1.44(m, 2H), 0.85-1.00(m, 2H), 0.90(t, J=7.1 Hz, 3H).

REFERENCE EXAMPLE 29 tert-butyl 4-(butyl{[(cyclohexylmethyl)amino]carbonyl}amino)-4-vinyl-1-piperidinecarboxylate To a cyclohexylisocyanate (0.35M solution in toluene, 10.1 mL) was added the compound prepared in Reference Example 28 (500 mg) and the mixture was stirred for 2 hours at room temperature. The reaction mixture was concentrated and the obtained residue was purified by column chromatography on silica gel (hexane:ethyl acetate=10:1→4:1) to give the title compound (615 mg) having the following physical data.
TLC: Rf 0.24 (hexane:ethyl acetate=3:1); NMR (CDCl$_3$):δ 6.14(dd, J=17.8, 10.8 Hz, 1H, 5.25(dd, J=10.8 Hz, 0.7 Hz, 1H), 5.16(dd, J=17.8 Hz, 0.7 Hz, 1H), 4.60-4.67(m, 1H), 3.55-3.69(m, 2H), 3.15-3.31(m, 4H), 3.03(t, J=5.7 Hz, 2H), 1.98-2.18(m, 2H), 1.62-1.77(m, 4H), 1.48-1.62(m, 2H), 1.45 (s, 9H), 1.11-1.37(m, 9H), 0.94(t, J=7.1 Hz, 3H), 0.81-0.92 (m, 2H).

REFERENCE EXAMPLE 30 tert-butyl 4-[{[allyl(cyclohexylmethyl)amino]carbonyl}(butyl)amino]-4-vinyl-1-piperidinecarboxylate To a solution of the compound prepared in Reference Example 29 (500 mg) in N,N-dimethylformamide (10 mL) were added allyl bromide (1.02 mL) and sodium hydride (60% in oil, 238 mg) under an atmosphere of argon and the mixture was stirred for 2 hours at 50° C. After adding water at 0° C., the mixture was concentrated. To the residue was added water and the mixture was extracted with dichloromethane. The organic layer was dried and concentrated. The obtained residue was purified by column chromatography on silica gel (hexane:ethyl acetate=7:1) to give the title compound (500 mg) having the following physical data.
TLC: Rf0.68 (hexane:ethyl acetate=3:1); NMR (CDCl$_3$):δ 6.31(dd, J=17.9, 11.0 Hz, 1H), 5.66-5.83(m, 1H), 4.99-5.28 (m, 4H), 3.91-4.08(m, 2H), 3.24-3.49(m, 4H), 2.97-3.18(m, 2H), 2.86-2.96(m, 2H), 1.96-2.11(m, 2H), 1.58-1.75(m, 8H), 1.45(s, 9H), 1.38-1.45(m, 1H), 1.09-1.30(m, 6H), 0.82-0.97 (m, 2H), 0.86(t, J=7.2 Hz, 3H).

EXAMPLE 38 tert-butyl 7-butyl-9-(cyclohexylmethyl)-8-oxo-3,7,9-triazaspiro[5.6]dodec-11-ene-3-carboxylate To a solution of the compound prepared in Reference Example 30 (1.07 g) in dichloromethane (232 mL) was added Grubbs' catalyst (benzylidene[1,3-bis(mesitylene)-2-imidazolidinylidene]tricyclohexylphosphine ruthenium(IV) dichloride, 787 mg) under an atmosphere of argon, and the mixture was stirred for 16 hours at room temperature. The reaction mixture was concentrated. The obtained residue was purified by column chromatography on silica gel (hexane:ethyl acetate=10:1→6:1) to give the compound of the present invention (115 mg) having the following physical data.
TLC: Rf 0.36 (hexane:ethyl acetate=3:1); NMR (CDCl$_3$):δ 5.95(d, J=11.1 Hz, 1H), 5.78-5.89(m, 1H), 3.50(t, J=7.3 Hz, 2H), 3.21(d, J=7.3 Hz, 2H), 3.10-3.18(m, 4H), 2.97-3.10(m, 2H), 1.92-2.08(m, 2H), 1.52-1.80(m, 9H), 1.46(s, 9H), 1.09-1.41(m, 6H), 0.92-1.05(m, 2H), 0.88(t, J=7.3 Hz, 3H); Mass: ESI (Pos., 20V) m/z 434 (M+H)$^+$, 378.

EXAMPLE 39

7-butyl-9-(cyclohexylmethyl)-3,7,9-triazaspiro[5.6]dodec-11-en-8-one

To a solution of the compound prepared in Example 38 (108 mg) in ethyl acetate (1.0 mL) was added 4N hydrochloric acid in ethyl acetate (3.0 mL) and the mixture was stirred for 2 hours at 0° C. The reaction mixture was concentrated. To the obtained residue were added dichloromethane and 1N aqueous solution of sodium hydroxide. The mixture was extracted with dichloromethane. The organic layer was dried and concentrated to give the compound of the present invention (83 mg) having the following physical data.
TLC: Rf 0.38 (chloroform:methanol:28% ammonia water=80:10:1); NMR (CDCl$_3$):δ 6.03(d, J=11.0 Hz, 1H), 5.75-5.84(m, 1H), 3.71(dd, J=5.1, 1.7 Hz, 2H), 3.50(t, J=7.3 Hz, 2H), 3.13(d, J=7.0 Hz, 2H), 2.97-3.07(m, 2H), 2.80-2.91 (m, 2H), 1.94-2.07(m, 2H), 1.83-1.95(m, 2H), 1.53-1.81(m, 8H), 1.09-1.52(m, 5H), 0.89-1.05(m, 2H), 0.89(t, J=7.2 Hz, 3H); Mass: ESI (Pos., 20V) m/z 334 (M+H)$^+$, 235.

EXAMPLE 40

7-butyl-9-(cyclohexylmethyl)-3,7,9-triazaspiro[5.6]dodecan-8-one

To a solution of the compound prepared in Example 39 (25 mg) in methanol (1.0 mL) was added 10% palladium on carbon (wet, 5.0 mg) and the mixture was stirred for 12 hours at room temperature under an atmosphere of hydrogen. The catalyst was removed by filtration using Celite (trademark). The filtrate was concentrated to give the compound of the present invention (25 mg) having the following physical data.
TLC: Rf 0.29 (chloroform:methanol:28% ammonia water=80:10:1); NMR (CDCl$_3$):δ 3.50(t, J=7.3 Hz, 2H), 3.25-3.36(m, 2H), 3.21(d, J=7.1 Hz, 2H), 3.06-3.17(m, 2H), 2.79-2.93(m, 2H), 1.96-2.14(m, 4H), 1.40-1.88(m, 10H), 1.07-1.40(m, 7H), 0.91-1.06(m, 2H), 0.91(t, J=7.0 Hz, 3H); Mass: ESI (Pos., 20V) m/z 336 (M+H)$^+$.

EXAMPLE 41

3-benzyl-7-butyl-9-(cyclohexylmethyl)-3,7,9-triazaspiro[5.6]dodecan-8-one

To a solution of the compound prepared in Example 40 (22 mg) in dichloromethane (0.5 mL) was added benzaldehyde (0.0133 mL) and the mixture was stirred for 10 minutes at room temperature. To the mixture was added sodium triacetoxy borohydride (28 mg) and the mixture was stirred for 4 hours. The reaction mixture was made alkaline with addition of 1N aqueous solution of sodium hydroxide and then extracted with dichloromethane. The organic layer was dried and concentrated. The obtained residue was purified by column chromatography on silica gel (hexane:ethyl acetate=1:2→ethyl acetate:methanol=30:1) to give the compound of the present invention (7.8 mg) having the following physical data.

TLC: Rf 0.37(ethyl acetate:methanol=10:1); NMR (CDCl$_3$):δ 7.18-7.35(m, 5H), 3.50(s, 2H), 3.20-3.37(m, 2H), 3.04-3.18(m, 4H), 2.67-2.81(m, 2H), 2.02-2.20(m, 4H), 1.49-1.88(m, 10H), 1.10-1.50(m, 9H), 0.87-1.04(m, 2H), 0.88(t, J=7.0 Hz, 3H); Mass: ESI (Pos., 20V) m/z 426 (M+H)$^+$.

EXAMPLE 41(1)

3-benzyl-7-butyl-9-(cyclohexylmethyl)-3,7,9-triazaspiro[5.6]dodec-11-en-8-one Using the compound prepared in Example 39 instead of the compound prepared in Example 40, the compound of the present invention having the following data was obtained by the same procedure of Example 41.

TLC: Rf 0.56(ethyl acetate:methanol=10:1); NMR (CDCl$_3$):δ 7.20-7.36(m, 5H), 5.94(d, J=11.2 Hz, 1H), 5.67-5.78(m, 1H), 3.68(dd, J=4.9, 1.5 Hz, 2H), 3.51(s, 2H), 3.21(t, J=7.0 Hz, 2H), 3.11(d, J=7.0 Hz, 2H), 2.65-2.76(m, 2H), 2.22-2.36(m, 2H), 2.08-2.21(m, 2H), 1.55-1.82(m, 8H), 1.37-1.50(m, 2H), 1.07-1.36(m, 5H), 0.83-1.00(m, 2H), 0.88(t, J=7.3 Hz, 3H); Mass: ESI (Pos., 20V) m/z 424 (M+H)$^+$.

REFERENCE EXAMPLE 31 tert-butyl 4-[butyl(2-isobutylacryloyl)amino]-4-vinyl-1-piperidinecarboxylate To a solution of the compound prepared in Reference Example 28 (85 mg) in dichloromethane (2.0 mL) were added triethylamine (0.070 mL) and 2-chlorocarbonyl-4-methyl-1-pentene (67 mg) at 0° C. and the mixture was stirred for 3 hours at 0° C. To the mixture was added methanol (0.10 mL) and then the mixture was concentrated. The obtained residue was purified by column chromatography on silica gel (hexane:ethyl acetate=6:1) to give the title compound (92 mg) having the following physical data.

TLC: Rf 0.50 (hexane:ethyl acetate=3:1); NMR (CDCl$_3$):δ 6.31(dd, J=17.8, 11.0 Hz, 1H), 5.01-5.22(m, 4H), 3.56-3.75 (m, 2H), 3.15-3.36(m, 4H), 2.09-2.20(m, 4H), 2.09(d, J=7.1 Hz, 2H1), 1.71-1.87(m, 1H), 1.47-1.59(m, 2H), 1.46(s, 9H), 1.12-1.30(m, 2H), 0.93(d, J=6.6 Hz, 6H), 0.88(t, J=7.3 Hz, 3H).

EXAMPLE 42 tert-butyl 1-butyl-3-isobutyl-2-oxo-1,8-diazaspiro[4.5]dec-3-ene-8-carboxylate To a solution of the compound prepared in Reference Example 31 (63 mg) in toluene (6.4 mL) was added Grubbs' catalyst (benzylidene[1,3-bis(mesitylene)-2-imidazolidinylidene]tricyclohexylphosphine ruthenium(IV) dichloride, 68 mg) and the mixture was stirred for 4 hours at 80° C. After cooling the reaction mixture to room temperature, the mixture was concentrated. The obtained residue was purified by column chromatography on silica gel (hexane:ethyl acetate=6:1) to give the title compound (56 mg) having the following physical data.

TLC: Rf 0.31 (hexane:ethyl acetate=3:1); NMR (CDCl$_3$):δ 7.01(s, 1H), 4.18-4.29(m, 2H), 3.17-3.28(m, 2H), 2.87-3.01 (m, 2H), 2.17(dd, J=7.1, 1.2 Hz, 2H), 1.83-2.04(m, 4H), 1.52-1.66(m, 2H), 1.49(s, 9H), 1.25-1.40(m, 3H), 0.93(t, J=7.3 Hz, 3H), 0.91(d, J=6.6 Hz, 6H).

EXAMPLE 43

1-butyl-3-isobutyl-1,8-diazaspiro[4.5]dec-3-en-2-one hydrochloride

Using the compound prepared in Example 42 instead of the compound prepared in Example 38, the compound of the present invention having the following data was obtained by the same procedure of Example 39.

TLC: Rf 0.35 (chloroform:methanol:28% ammonia water=80:10:1); NMR (CDCl$_3$):δ 6.98(s, 1H), 3.41-3.54(m, 2H), 3.25-3.34(m, 2H), 2.98-3.14(m, 2H), 2.34-2.51(m, 2H), 2.17(dd, J=7.1, 1.1 Hz, 2H), 1.85-2.01(m, 1H), 1.55-1.69(m, 2H), 1.41-1.52(m, 2H), 1.30-1.41(m, 2H), 0.93(t, J=7.2 Hz, 3H), 0.91(d, J=7.0 Hz, 6H).

EXAMPLE 44

8-benzyl-1-butyl-3-isobutyl-1,8-diazaspiro[4.5]dec-3-en-2-one

Using the compound prepared in Example 43 instead of the compound prepared in Example 40, the compound of the present invention having the following data was obtained by the same procedure of Example 41.

TLC: Rf 0.43 (chloroform:methanol=10:1); NMR (CDCl$_3$):δ 7.23-7.41(m, 5H), 7.00(s, 1H), 3.59(s, 2H), 3.20-3.30(m, 2H), 2.89-3.01(m, 2H), 2.17-2.37(m, 4H), 2.14(dd, J=7.1, 1.2 Hz, 2H), 1.84-2.01(m, 1H), 1.53-1.65(m, 2H), 1.23-1.41(m, 4H), 0.92(t, J=7.2 Hz, 3H), 0.90(d, J=6.6 Hz, 6).

BIOLOGICAL EXAMPLE

The fact that the compound of the present invention represented by formula (1) has CCR5 antagonism or CCR2 antagonism was demonstrated, for example, by the following experiment. The total operation was based on the basic genetic engineering to prepare gene-highly expressing cells, and the ordinary methods were utilized. Also, in the assaying method of the present invention, in order to evaluate the compound of the present invention, assaying accuracy and/or assaying sensitivity was improved as described below. The detailed experimental methods are shown below.

Test method:

(1) Isolation of Human CCR5 Gene

Human placental cDNA was prepared using Marathon cDNA amplification kit (Clontech). PCR primers hCCR5Xbal-F1:
5'-AGCTAGTCTAGATCCGTTCCCCTACAA-GAAACTCTCC-3'(SEQ ID NO:1) and hCCR5Xbal-R1:
5'-AGCTAGTCTAGAGTGCACAACTCT-GACTGGGTCACCA-3'(SEQ ID NO:2) were designed based on the sequence of GenBank U54994.

Using the human placental cDNA as the template and using Ex Taq (Takara), PCR reaction (2 minutes at 95° C.→(30 seconds at 95° C., 45 seconds at 60° C., 1 minute at 72° C.)×35 times) was carried out. The thus amplified PCR product was subjected to a 1% agarose gel electrophoresis, purified using QIAquick Gel Extraction Kit (QUIAGEN) and then digested with a restriction enzyme XbaI. The digested fragments were ligated to an expression vector pEF-BOS-bsr using DNA Ligation Kit Ver. 2 (Takara) and transformed into Escherichia coli DH5α. By preparing the resulting plasmid pEF-BOS-bsr/hCCR5, its DNA sequence was verified.

(2) Culturing of CHO Cell

CHO-dhfr(−) was cultured using Ham's F-12 (containing fetal bovine serum (10%), penicillin (50 U/mL) and streptomycin (50 mg/mL)). Also, the transduced cell was cultured by adding blasticidin (5 mg/mL) to the above medium.

(3) Transduction into CHO Cell

The plasmid pEF-BOS-bsr/hCCR5 was transduced into the CHO-dhfr(−) cell using DMRIE-C reagent (Gibco BRL). After 48 hours, the medium was replaced with a medium containing 5 mg/ml of blasticidin to carry out the selection, thereby establishing a stably over-expressing cell.

(4) Inhibition Test on the Binding of RANTES to CCR5 (Activity of RANTES to Induce Transient Increase of Ca ion).

The thus established human CCR5 stably over-expressing CHO cell (CCR5/CHO cell) was suspended in Ham's F-12 medium containing FBS (10%) and seeded at a density of 3.0×10$^6$ cells/well into a 96 well plate. One day after culturing at 37° C., the culture supernatant was discarded, and Ham's F-12 medium (containing Fura-2AM (5 μM), Probenecid (2.5 mM) and HEPES (20 mM; pH 7.4)) was dispensed in 80 μl/well portions to carry out 1 hour of incubation at 37° C. under shaded condition. After washing twice with 1×Hanks/HEPES (20 mM; pH 7.4) solution, the same solution was dispensed in 100 μl/well portions. Each of the test compounds was added to the thus Fura-2AM-incorporated CCR5/CHO cell, and 3 minutes thereafter, a recombinant human RANTES (PeproTach) diluted with 1×Hanks/HEPES (20 mM; pH 7.4) solution was added thereto to a final concentration of 10 nM. Transient increase in the intracellular Ca$^{2+}$ concentration induced by the human RANTES was measured using a Ca$^{2+}$ detector for 96 well use (Hamamatsu Photonics), and inhibition ratio (%) of the test compound was calculated by the following calculation formula.

Inhibition ratio=$(Ec-Ea)/Ec$×100

Ec: measured value of Ca$^2$+transient increase by RANTES
Ea: measured value of Ca$^2$+transient increase by RANTES when a test compound was added.

As a result, the compounds of the present invention showed an inhibition ratio of 50% or more at 10 μM.

(5) Inhibition test on the binding of MCP-1 to CCR2 (activity of MCP-1 to induce transient increase of Ca ion).

Human CCR2-expressing cells, for example, human monocyte cell line THP-1 (ATCC No. TIB-202), were suspended in RPMI1640 medium containing FBS (10%), Fura2-AM (5 μM), Probenecid (2.5 mM) and HEPES (20 mM; pH 7.4) to give a density of 5.0×10$^6$ cells/ml and incubated at 37° C. for 30 minutes under shading. Then, 4-fold to 8-fold 1×Hanks/HEPES (20 mM; pH 7.4)/Probenecid (2.5 mM) was added thereto, followed by further incubation at 37° C. for 30 minutes under shading. After the cells were washed with 1×Hanks/HEPES (20 mM; pH 7.4)/Probenecid (2.5 mM) solution, the cells were suspended again by the same solution to give a density of 2.0×10$^6$ cells/ml and added to a 96-well plate at 100 μl/well. Each of the test compounds was added, and 3 minutes thereafter, a recombinant human MCP-1 (PeproTach) diluted with 1×Hanks/HEPES (20 mM; pH 7.4)/Probenecid (2.5 mM) was added thereto to a final concentration of 30 nM. Transient increase in the intracellular Ca$^{2+}$ concentration induced by the human MCP-1 was measured using a Ca$^{2+}$ detector for 96 well use (Hamamatsu Photonics), and inhibition ratio (%) of the test compound was calculated by the following calculation formula.

Inhibition ratio=$(Ec-Ea)/Ec$×100

Ec: measured value of Ca$^{2+}$ transient increase by MCP-1
Ea: measured value of Ca$^{2+}$ transient increase by MCP-1 when a test compound was added.

As a result, the compounds of the present invention inhibited binding of MCP-1 and CCR2. For example, the compound of Example 37 showed an inhibition ratio of 50% or more at 10 μM.

FORMULATION EXAMPLE 1

The following components were admixed in a conventional manner, punched out to give 100,000 tablets each containing 50 mg of active ingredient:

1-butyl-3-isobutyl-1,3,8-triazaspiro[4.5]decane-2,4-dione (5.0 kg); calcium carboxymethyl cellulose (disintegrant) (0.2 kg); magnesium stearate (lubricant) (0.1 kg); microcrystalline cellulose (4.7 kg)

FORMULATION EXAMPLE 2

The following components were admixed in a conventional technique. The solution was sterilized in a conventional technique, filled in ampoules 5 mL each and freeze-dried over in a conventional technique to give 100,000 ampoules each containing 20 mg of active ingredient:

1-butyl-3-isobutyl-1,3,8-triazaspiro[4.5]decane-2,4-dione (2.0 kg); mannitol (20 kg); distilled water (500 L).

INDUSTRIAL APPLICABILITY

The compounds of the present invention represented by formula (I), salts thereof, N-oxides thereof, quaternary ammonium salts thereof or solvates salts, or prodrugs thereof are safe and low-toxic, so that they can be used as pharmaceutical bulks. Also, they have chemokine antagonistic action, so that they are useful for prevention and/or treatment

What is claimed is:

1. A spiro-piperidine compound represented by formula (I):

wherein $R^1$ represents hydrogen, an aliphatic hydrocarbon group which may have a substituent(s) or a cyclic group which may have a substituent(s); and ring A represents a tetrahydropyrimidin-2-(1H)-one group represented by the following formula which may have a substituent(s), in which 2,5-diketopiperazine having a spiro bond at the 3-position is excluded,

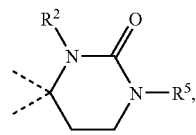

wherein $R^2$ represents hydrogen, an aliphatic hydrocarbon group which may have a substituent(s) in which the aliphatic hydrocarbon group is selected from the group consisting of ethyl, propyl, isopropyl, butyl, isobutyl, sec-butyl, tert-butyl, pentyl, hexyl, heptyl, octyl, C2-8 alkenyl and C2-8 alkynyl, a hydroxyl group which may be protected, carboxy which may be protected, carbamoyl which may be protected, or a cyclic group which may have a substituent(s) and, $R^5$ represents hydrogen, an aliphatic hydrocarbon group which may have a substituent(s), hydroxyl which may be protected, carboxy which may be protected, or a cyclic group which may have a substituent(s), a salt thereof or a quaternary ammonium salt thereof, wherein the cyclic group of $R^1$, $R^2$ and $R^5$ is selected from the group consisting of cyclopropane, benzene, cyclohexane, cyclohexene, thiophene, pyrazole, isothiazole, thiazole, imidazole, furan, dihydropyrazole, quinoline, benzodioxane, dioxaindane, benzofuran, pyridine, tetrahydropyran, triazole, pyrrole, oxazole, isoxazole, and oxadiazole.

2. The spiro-piperidine compound according to claim 1, wherein R1 is a C1-10 aliphatic hydrocarbon group which may have a substituent(s), a salt thereof or a quaternary ammonium salt thereof.

3. A spiro-piperidine compound represented by formula (I):

wherein $R^1$ is a 5- to 10-membered monocyclic or bicyclic cyclic group which may have a substituent(s), and ring A represents a tetrahydropyrimidin-2-(1H)-one group which may have a substituent(s), in which 2,5-diketopiperazine having a spiro bond at the 3-position is excluded, a salt thereof or a quaternary ammonium salt thereof, wherein the 5- to 10-memebered monocyclic or bicyclic cyclic group is selected from the group consisting of benzene, cyclohexane, cyclohexene, thiophene, pyrazole, isothiazole, thiazole, imidazole, furan, dihydropyrazole, quinoline, benzodioxane, dioxaindane, benzofuran, pyridine, tetrahydropyran, triazole, pyrrole, oxazole, isoxazole, and oxadiazole.

4. The spiro-piperidine compound according to claim 1, wherein $R^1$ is alkyl having from 1 to 6 carbon atoms substituted with a 3- to 10-membered monocyclic or bicyclic cyclic group which may have a substituent(s), a salt thereof or a quaternary ammonium salt thereof, wherein the 3- to 10-membered monocyclic or bicyclic cyclic group is selected from the group consisting of C3-6 cycloalkyl, C4-6 cycloalkenyl, benzene, pyrazole, thiazole, furan, thiophene, quinoline, benzodioxane, dioxaindane, benzofuran, imidazole, isothiazole, dihydropyrazole, pyridine, tetrahydropyran, triazole, pyrrole, oxazole, isoxazole, and oxadiazole.

5. A pharmaceutical composition which comprises the spiro-piperidine compound according to claim 1, a salt thereof or a quaternary ammonium salt thereof, and a pharmaceutically acceptable carrier or diluent.

6. The spiro-piperidine compound according to claim 1, wherein $R^2$ is an aliphatic hydrocarbon group which may have a substituent(s) in which the aliphatic hydrocarbon group is selected from the group consisting of ethyl, propyl, isopropyl, butyl, isobutyl, sec-butyl, tert-butyl, pentyl, hexyl, heptyl, octyl, C2-8 alkenyl and C2-8 alkynyl.

* * * * *

UNITED STATES PATENT AND TRADEMARK OFFICE
CERTIFICATE OF CORRECTION

PATENT NO. : 7,498,323 B2
APPLICATION NO. : 10/553596
DATED : March 3, 2009
INVENTOR(S) : Rena Nishizawa et al.

It is certified that error appears in the above-identified patent and that said Letters Patent is hereby corrected as shown below:

On the Title page
Item (73) Assignee:
delete "Ono Pharmaceuticals Co., Ltd."
and insert --Ono Pharmaceutical Co., Ltd.--

Signed and Sealed this

Thirtieth Day of June, 2009

JOHN DOLL
*Acting Director of the United States Patent and Trademark Office*